US011135325B2

(12) United States Patent
Osinski et al.

(10) Patent No.: US 11,135,325 B2
(45) Date of Patent: Oct. 5, 2021

(54) METHODS AND COMPOSITIONS FOR ANTIMICROBIAL TREATMENT

(71) Applicants: Marek A. Osinski, Albuquerque, NM (US); Hugh D. C. Smyth, Austin, TX (US); Leisha Marie Armijo, Albuquerque, NM (US); Hennaka Mudiyanselage Herath Nihal Bandara, Herston (AU)

(72) Inventors: Marek A. Osinski, Albuquerque, NM (US); Hugh D. C. Smyth, Austin, TX (US); Leisha Marie Armijo, Albuquerque, NM (US); Hennaka Mudiyanselage Herath Nihal Bandara, Herston (AU)

(*) Notice: Subject to any disclaimer, the term of this patent is extended or adjusted under 35 U.S.C. 154(b) by 0 days.

(21) Appl. No.: 15/549,974

(22) PCT Filed: Feb. 9, 2016

(86) PCT No.: PCT/US2016/017163
§ 371 (c)(1),
(2) Date: Aug. 9, 2017

(87) PCT Pub. No.: WO2016/130554
PCT Pub. Date: Aug. 18, 2016

(65) Prior Publication Data
US 2018/0021463 A1 Jan. 25, 2018

Related U.S. Application Data

(60) Provisional application No. 62/113,838, filed on Feb. 9, 2015.

(51) Int. Cl.
| | |
|---|---|
| A61L 2/02 | (2006.01) |
| A01N 25/26 | (2006.01) |
| A61K 33/26 | (2006.01) |
| A61K 41/00 | (2020.01) |
| A61L 2/238 | (2006.01) |
| A61L 29/10 | (2006.01) |
| A61L 31/08 | (2006.01) |

(52) U.S. Cl.
CPC .............. *A61L 2/02* (2013.01); *A01N 25/26* (2013.01); *A61K 33/26* (2013.01); *A61K 41/00* (2013.01); *A61L 2/238* (2013.01); *A61L 29/106* (2013.01); *A61L 31/088* (2013.01)

(58) Field of Classification Search
CPC .......... A61L 2/02; A61L 2/238; A61L 29/106; A61L 31/088; A01N 25/26; A61K 41/00; A61K 33/26
See application file for complete search history.

(56) References Cited

U.S. PATENT DOCUMENTS

| | | | | |
|---|---|---|---|---|
| 2004/0193039 | A1* | 9/2004 | Weber | A61M 25/0009 600/411 |
| 2009/0226521 | A1* | 9/2009 | Smyth | A61K 47/6921 424/484 |
| 2010/0233245 | A1 | 9/2010 | Narayana | |
| 2010/0286791 | A1* | 11/2010 | Goldsmith | A61B 17/0057 623/23.7 |
| 2011/0171123 | A1* | 7/2011 | Shirtliff | A61K 49/1875 424/1.11 |
| 2013/0129630 | A1* | 5/2013 | Haik | A61K 41/0052 424/9.3 |
| 2013/0224125 | A1* | 8/2013 | Kolazi | A61K 8/463 424/52 |
| 2014/0093550 | A1 | 4/2014 | Mcnealy et al. | |
| 2014/0234429 | A1* | 8/2014 | Mahmoudi | A61K 9/14 424/490 |

FOREIGN PATENT DOCUMENTS

WO WO-2016130554 A1 8/2016

OTHER PUBLICATIONS

"International Application Serial No. PCT/US2016/017163, International Preliminary Report on Patentability dated Aug. 24, 2017", 9 pgs.
"International Application Serial No. PCT/US2016/017163, International Search Report dated May 18, 2016", 4 pgs.
"International Application Serial No. PCT/US2016/017163, Written Opinion dated May 18, 2016", 7 pgs.
Armijo, Leisha, et al., "Delivery of Tobramycin Coupied to iron Oxide Nanoparticles Across the Biofilm of Mucoidal Pseudomonas Aeruginosa and Investigation of its Efficacy", Proceedings of SPIE, Colloidal Nanoparticles for Biomedical Applications IX, Article 895501, (Apr. 8, 2014), 13 pgs.
Armijo, Leisha, et al., "Iron Oxide Nanocrystals for Magnetic Hyperthermia Applications", nanomaterials, 2, (2012), 134-146.
Armijo, Leisha M., et al., "Multifunctional Superparamagnetic Nanoparticles for Enhanced Drug Transport in Cyctic Fibrosis", Proc. of SPIE, vol. 8548, (2012), 1-12.
Bandara, H, et al., "Bacterial lipopolysaccharides variably modulate in vitro biofilm formation of *Candida* species", Journal of Medical Microbiology, 59, (2010), 1225-1234.
Bandara, H, et al., "Pseudomanas aeruginosa inhibits in-vitro Candida biofilm development", BMC Microbiology. 10:125, [Online]. Retrieved from the Internet: <URL: http://www.biomedcentral.com/1471-2180/10/125>, (2010), 9 pgs.

(Continued)

Primary Examiner — Genevieve S Alley
(74) Attorney, Agent, or Firm — Schwegman Lundberg & Woessner, P.A.

(57) ABSTRACT

Various embodiments disclosed relate to methods and compositions for antimicrobial treatment. In various embodiments, the present invention provides a method of antimicrobial treatment. The method includes at least one of exposing at least one microbe to a magnetic field, and contacting the at least one microbe with at least one nanoparticle including iron.

14 Claims, 20 Drawing Sheets
(2 of 20 Drawing Sheet(s) Filed in Color)

(56) References Cited

OTHER PUBLICATIONS

Bao, Yuping, et al., "Preparation of functionalized and gold-coated cobalt nanocrystals for biomedical applications", Journal of Magnetism and Magnetic Materials 293, (2005), 15-19.
Benson, Dianna E., et al., "Magnetic Field Enhancement of Antibiotic Activity in Biofilm Forming Pseudomonas aeruginosa", ASAIO Journal, (1994), M371-M376.
Bronstein, Lyudmila M., et al., "Influence of Iron Oleate Complex Structure on Iron Oxide Nanoparticle Formation", Chem. Mater. 19, (2007), 3624-3632.
Chem, Tong, et al., "Carboxymethyl Chitosan-Functionalized Magnetic Nanoparticles for Disruption of Biofilms of *Staphylococcus aureus* and *Escherichia coli*", Ind. Eng. Chem. Res. 51, (2012), 13164-13172.
Connolly, J., et al., "Silica Coating of Cobalt Nanoparticles Increases Their Magnetic and Chemical Stability for Biomedical Applications", European Cells and Materials, vol. 3, Suppl. 2, (2002), 106-109.
Cotar, Ani Ioana, et al., "Nanotechnological Solution for Improving the Antibiotic Efficiency Against Biofilms Developed by Gram-Negative Bacterial Strains", Open Access Journal—Letters in Applied NanoBioScience, vol. 2, Issue 1, (2013), 97-104.
Cui, Yan, et al., "The molecular mechanism of action of bactericidal gold nanoparticles *Escherichia coli*", Biomaterials 33, (2012), 2327-2333.
D'Angelo, Ivana, et al., "Improving the efficacy of inhaled drugs in cystic fibrosis: Challenges and emerging drug deliver strategies", Advanced Drug Delivery Reviews 75 (2014), 92-111.
Disegi, John A., et al., "Cobalt-Base Alloys for Biomedical Applications", ASTM STP 1365, (Oct. 1999), 5 pgs.
Durmus, Naside G., et al., "Eradicatting Antibiotic-Resistant Biofilms with Silver-Conjugated Superparamagnetic Iron Oxide Nanoparticles", Advanced Healthcare Materials 2, (2013), 165-171.
Fabrega, Julia, et al., "Interactions of Silver Nanoparticles with Pseudomonas putida Biofilms", Environ. Sci. Technnol. 43, (2009), 9004-9009.
Gao, Weimin, et al., "Effects of a Strong Static Magnetic Field on Bacterium Shewanella oneidensis: An Assessment by Using Whole Genome Microarray", Bioelectromagnetics 26, (2005), 558-563.
Grosman, Zdenek, et al., "Effects of Static Magnetic Field on Some Pathogenic Microorganisms", Acta Univ. Palacki. Olomuc. Fac Med., vol. 134, (1992), 4 pgs.
Gunawan, Poernomo, et al., "Hollow Fiber Membrane Decorated with Ag/MWNTs: Toward Effective Water Disinfection and Biofouling Control", American Chemical Society, vol. 5, No. 12, (2011), 10033-10040.
Gupta, Ajay K., et al., "Synthesis and surface engineering of iron oxide nanoparticles for biomedical applications", Biomaterials 26, (2005), 3995-4021.
Hassett, Daniel J., et al., "Anaerobic metabolism and quorum sensing by Pseudomonas aeruginosa biofilms in chronically infected cystic fibrosis airways: rethinking antibiotic treatment strategies and drug targets", Advanced Drug Delivery Reviews 54, (2002), 1425-1443.
Hermanson, Greg T., "Bioconjugate Techniques", Front cover illustration and table of contents for book., (1996), 1-14.
Hu, Wenbing, et al., "Graphene-Based Antibacterial Paper", vol. 4, No. 7, [Online]. Retrieved from the Internet: <URL: www.acsano.org, (2010), 4317-4323.
Johannsen, M. et al., "Morbidity and quality of life during thermotherapy using magnetic nanoparticles in locally recurrent prostate cancer: Results of a prospective phase I trial", Int. J. Hyperthermia 23 (3), (May 2007), 315-323.
Khoury, Antoine E., et al., "Prevention and Control of Bacterial Infections Associated with Medical Devices", ASAIO Journal, (1992), M174-M178.
Kohno, Masahiro, et al., "Effect of static magnetic fields on bacteria: *Streptococcus mutans*, *Staphylococcus aureus*, and *Escherichia coli*", Pathophysiology 7, (2000), 143-148.
Laszio, Janos, et al., "Static Magnetic Field Exposure Fails to Affect the Viability of Different Bacteria Strains", Bioelectromagnetics 31, (2010), 220-225.
Lee, Daeyeon, "Antibacterial Properties of Ag Nanoparticle Loaded Multilayers and Formation of Magnetically Directed Antibacterial Microparticles", Langmuir 21, (2005), 9651-9659.
Liu, Shaobin, et al., "Sharper and Faster "Nano Darts" Kill More Bacteria: A Study of Antibacterial Activity of Individually Dispersed Pristine Single-Walled Carbon Nanotube", [Online]. Retrieved from the Internet: <URL: www.acsnano.org, vol. 3, No. 12, (2009), 3891-3902.
Liu, Yan, et al., "Magnetic field effect on singlet oxygen production in a biochemical system", Chem.. Commun., (2005), 174-176.
Makhluf, Shirly, et al., "Microwave-Assisted Synthesis of Nanocrystalline MgO and Its Use as a Bacteriocide", Advanced Functional Materials 15, (2005), 1708-1715.
Martin, Gail, "Development of an orally relevant biofilem disinfection model (Submitted in fulfilment of the conditionings governing candidate for the degree of Doctor of Philosophy)", University College, London, (Sep. 2011), 317 pgs.
McGill, Shayna L., et al., "Enhanced drug transport through alginate biofilms using magnetic nanoparticles", Proc. of SPIE, vol. 7189, (2009), 718918-1 to 718918-8.
McGill, Shayna L., et al., "Magnetically Responsive Nanoparticles for Drug Delivery Applications Using Low Magnetic Field Strengths", IEEE Transactions on Nanobioscience, vol. 8, No. 1, (Mar. 2009), 33-42.
McLeod, et al., "A biofilm growth protocol and the design of a magnetic field exposure setup to be used in the study of magnetic fields as a means of controlling bacterial biofilms", Bioelectromagnetics, vol. 31 , pp. 56-63, See Abstract, (2010), 56-63.
Park, Hongsuk, et al., "Inactivation of Pseudomonas aeruginosa PA01 biofilms by hyperthermia using superpararnegnetic nanoparticles", Journal of Microbiological Methods 84, (Oct. 30, 2010), 41-45.
Park, Jongnam, et al., "Ultra-large-scale syntheses of monodisperse nanocrystals", Nature Materials, vol. 3, Letters, (Dec. 2004), 891-895.
Piatti, Elena, et al., "Antibacterial effect of a magnetic field on Serratia marcescens and related virulence to Hordeum vulgare and Rubus fruticosus callus cells", Comparative Biochemistry and Physiology Part B 132, (2002), 359-365.
Potenza, Lucia, et al., "Effects of a static magnetic field on cell growth and gene expression in *Escherichia coli*", Mutation Research 561, (2004), 53-62.
Qiang, You, et al., "Iron / iron oxide core-shell nanoclusters for biomedical applications", Journal of Nanoparticle Research 8, (2006), 489-496.
Radovic-Moreno, Aleksandar F., et al., "Surface Charge-Switching Polymeric Nanoparticles for Bacterial Cell Wall-Targeted Delivery of Antibiotics", ACSNANO vol. 6, No. 5 (2012), 4279-4287.
Raghupathi, Krishna R., et al., "Size-Dependent Bacterial Growth Inhibition and Mechanism of Antibacterial Activity of Zinc Oxide Nanoparticles", Langmuir 27, (2011), 4020-4028.
Rodriguez, Diana, et al., "Control of planktonic bacterial cells and biofilms through magnetic hyperthermia", IEEE Transactions on Magnetics (impact Factor 1:21), (2013), 2 pgs.
Samarbaf-Zadeh, A. R., et al., The Effect of Static Electromagnetic Field on Cephalothin-Resistant Pseudornon as Aeroginose, Jundishapur Journal of Natural Pharmaceutical Products, vol. 1, (2006), 13-17.
Shrivastava, Siddhartha, et al., "Characterization of enhanced antibacterial effects of novel silver nanoparticles", Nanotechnology 18, (2007), 1-9.
Taylor, Eric N., et al., "The use of superparamagnetic nanoparticles for prosthetic biofilm prevention", International Journal of Nanomedicine 4, (2009), 145-152.
Armijo, Leisha M., et al., "Delivery of antibiotics coupled to iron oxide nanoparticles across the biofilm of mucoid Pseudonomas aeruginosa and investigation of their efficacy", Proc. of SPIE vol. 8955, (2014), 12 pgs.

(56) References Cited

OTHER PUBLICATIONS

Liu, Yuan, et al., "Topical ferumoxytol nanoparticles disrupt biofilms and prevent tooth decay in vivo via intrinsic catalytic activity", Nature Communications 9, Article No. 2920, (2018), 12 pgs.

* cited by examiner

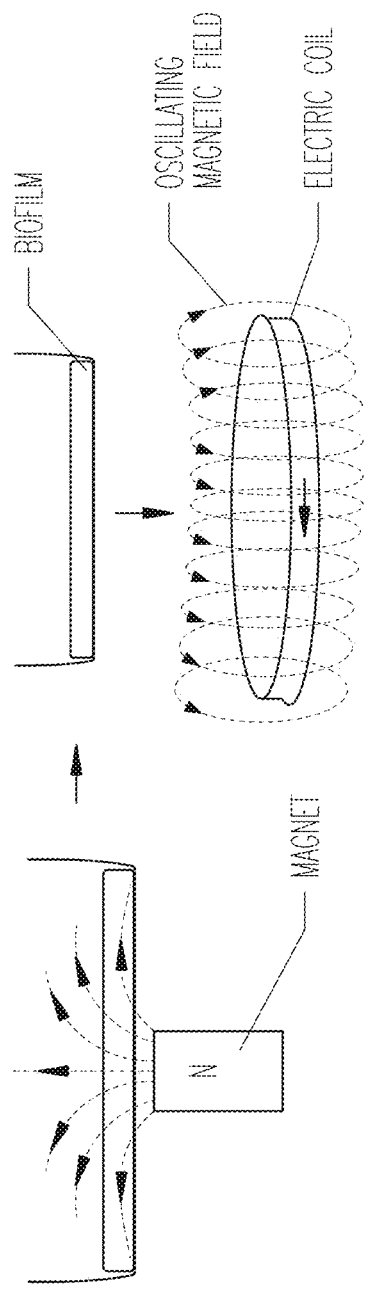

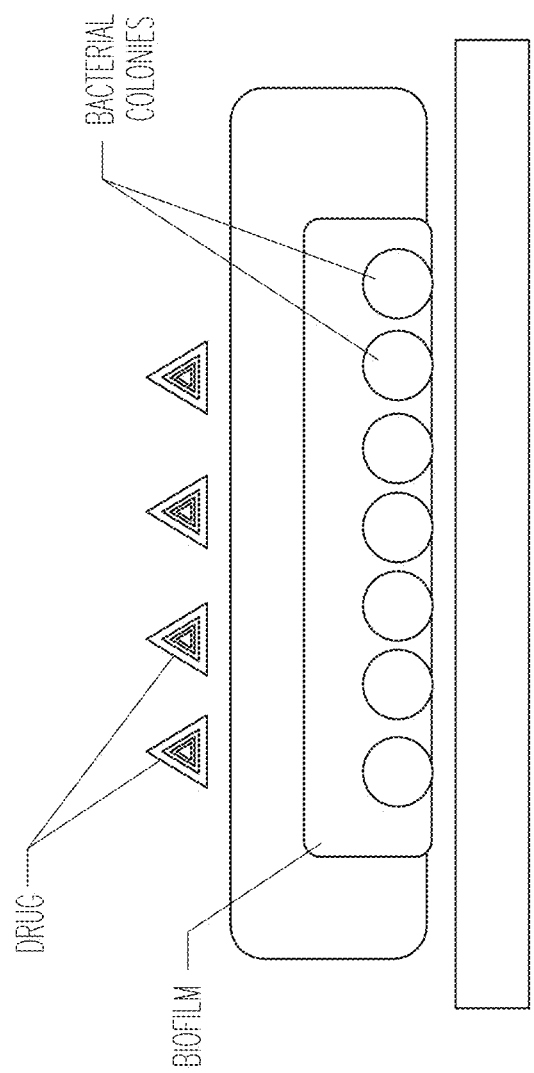

METHODS AND COMPOSITIONS FOR ANTIMICROBIAL TREATMENT

CROSS-REFERENCE TO RELATED APPLICATION

This application is a U.S. National Stage Filing under 35 U.S.C. § 371 of International Patent Application Serial No. PCT/US2016/017163, filed Feb. 9, 2016, and published on Aug. 18, 2016 as WO/2016/130554, which claims the benefit of priority to U.S. Provisional Patent Application Ser. No. 62/113,838 filed Feb. 9, 2015, the disclosure of each of which are is incorporated herein in their its entirety by reference.

STATEMENT OF GOVERNMENT SUPPORT

This invention was made with Government support under grant 1R21HL092812-01 A1 awarded by the NIH. The U.S. Government has certain rights in this invention.

BACKGROUND

In nature, most microorganisms prefer a communal lifestyle of growth rather than surviving as solitary cells or single species. These microbial communities are termed biofilms. Biofilms are a complex functional community of one or more species of microbes encased in an extracellular polymeric network and attached to one another or to a solid surface. These communities are hierarchically arranged and three dimensionally organized communities in order to gain ecological advantages compared to their planktonic counterparts for better survival. These include protection from the environment, nutritional availability and metabolic cooperation, acquisition of new genetic traits and antimicrobial resistance. According to NIH statistics, biofilms are responsible for over 80% of all microbial infections in the body. These include, chronic wound infections, chronic lung infections associated with cystic fibrosis, chronic osteomyelitis, otitis media, chronic rhinosinusitis, endocarditis, urinary tract infections, dental and periodontal infections, chronic eye infections, gastrointestinal tract infections, as well as the infections associated with medical device such as ventilator and tracheal tubing, prosthetic joints, heart valves, cardiac pacemakers, internal fixations, vascular grafts, stents, and catheters.

Gram positive pathogens such as *Staphylococcus epidermidis, Staphylococcus aureus, Streptococcus* spp, Gram negative bacteria such as *Pseudomonas aeruginosa*, Enterobacteriaceae, and fungi such as *Candida* spp are frequently associated with biofilm associated infections. In USA, *P. aeruginosa* is the most isolated hospital pathogen and the second commonest cause for ventilator associated pneumonia. Moreover, *P. aeruginosa* biofilms cause lung infections 95% of adult CF patients, chronic would infections, catheter associated urinary tract infections, chronic otitis media, rhinosinusitis and contact lens associated keratitis.

Due to slow growth rate, altered microbial metabolism, phenotypic changes, oxygen gradient and pH differences, extracellular biofilm substances and persister cells, complete eradication of *P. aeruginosa* biofilms with conventional antibiotics is virtually impossible. Many in vitro and in vivo studies have been conducted in preventing and eliminating *P. aeruginosa* biofilms. However, due to high antimicrobial resistance, it is generally accepted that biofilm control can be more efficient when antibiotic is combined with another antibiofilm agent. For example, established *P. aeruginosa* biofilms in CF lungs are treated with intensive antibiotic treatment (nebulized tobramycin) and DNAases (to disrupt eDNA/Extracellular DNA in biofilm matrices). In addition, new treatment modalities have constantly been sought. Early investigations explored the possibility of using electromagnetic fields in eliminating *P. aeruginosa* biofilms. Furthermore, many other pathogens such as *Escherichia coli, Staphylococcus aureus, Streptococcus mutans, rubus fruticosus, Shewanella oneidensis, Saccharomyces cerevisiae, Bacillus circulans, Micrococcus luteus, Pseudomonas fluorescens, Salmonella enteritidis, Serratia marcescens* has been exposed to magnetic fields to investigate possible antibacterial effects. However, most results observed in these studies were not favorable. In addition, magnetic fields have been experimented in variety of fields, for example, there are several reports on usage of magnetic fields in agricultural microbiology as a disinfectant as well as to improve the productivity of beneficial bacteria.

Despite its official classification as an "opportunistic pathogen," *Pseudomonas aeruginosa* remains a major worldwide public health problem due to its veracity in the environment, its ability to colonize virtually any and all regions of the body, and its overall vitality which has allowed it to adapt to a wide range of environmental conditions. With a shocking mortality rate of 50% of higher, *P. aerignosa* is the number one etiology presenting in hospital acquired (nosocomial) infections. This gram negative species is a member of the class Gammaproteobacteria and the family of Pseudomonadaceae. Responsible for the morbidity and mortality of oncology and cystic fibrosis (CF) patients, *P. aeruginosa* is also prevalent in the well as burn unit and the ICU. Infecting up to two-thirds of ICU patients with nosocomial pneumonia. In CF, *P. aeruginosa* complicates more than 90% of respiratory failure cases. *P. aeruginosa* has inherent as well as acquired resistance to many drug classes. In addition, it possesses the ability to quickly alter its genetics to impart resistance to the presence of new, unrecognized treatments. *P. aeruginosa* is able to grow with limited nutrients; it can use acetate and citrate as sole carbon sources, may thrive without oxygen (if $NO_3$ is available as an electron acceptor for cellular respiration), and is so hardy that it can actually colonize deionized water.

The switch from planktonic to the biofilm mode is initiated under low oxygen, low nutrient conditions, or in response to the presence of antibiotics, antibodies, bacteriophages, or other stressors. Bacterial cells release chemical signals which trigger the switch in neighboring populations. Planktonic cells undergo the phenotypic switch by means of gene regulation. In order to form a biofilm, planktonic cells first adhere to a surface via Van der Waals forces; weak non-covalent interactions, or by using flagella or cilia as an anchor. After that, quorum sensing is used to recruit other bacterial cells; an inducer binds the bacterial QS receptor promoting transcription and translation of the genes necessary for cell aggregation and subsequently biofilm production. Once a colony is established, the anchor cells begin to produce exopolysacchride which forms a protective layer around the bacterial colonies. N-Acyl homoserine lactones are signaling molecules, called auto-inducers (AI's) used in QS. It is interesting to note that compounds with similar structures may be of interest for blocking QS (receptor antagonists), and thus, inhibiting biofilm formation.

Formation of a biofilm results in slower growth combined with bacterial production of extracellular polysaccharides (EPS) which form a physical barrier with limits the ability of antibiotic drugs to interact with the bacteria. The EPS layer is composed of several different polymers, but mostly consisting of a slimy anionic co-block polymer which forms a viscous gum when in the presence of water, hence the term, "mucoidal." Alginate or alginic acid is a linear copolymer consisting of homopolymeric blocks of (1-4)-linked β-D-mannuronate (M) and its C-5 epimer α-L-guluronate (G) residues. The M and G residues are covalently linked together in different sequences or blocks. The monomers may be homopolymeric, in blocks of consecutive G-residues, consecutive M-residues or alternating M and G-residues (co-block).

Bacterial biofilm infections pose a significant public health problem since they allow bacteria to colonize inert objects such as indwelling catheters, orthodontic wires, stents, surgical sutures, and respirator tubes. In addition biofilms increase veracity of infections in burns, open wounds, cystic fibrosis (CF) lungs, and virtually every imaginable organ system. The bacterial production of extracellular biofilms significantly reduces the efficacy of therapeutics, foremost, due to the physical barrier to drug diffusion.

In addition, with regards to the more than 20 genes that are differentially expressed in tobramycin treated biofilms, simple existence in a biofilm induces moderate resistance to all antibiotic drugs. For example, it was recently discovered that certain periplasmic glucans encoded in for by the genome, interact physically with tobramycin suggesting that these glucose polymers may prevent antibiotics from reaching their sites of action by requisitioning the antimicrobial agents in the periplasm. These results demonstrate the fact that biofilms do not solely inhibit drug activity by serving as a physical barrier to treatments. This speaks to the tremendous complexity of the resistance mechanisms available to this particular species.

SUMMARY OF THE INVENTION

In various embodiments, the present invention provides a method of antimicrobial treatment. The method includes at least one of exposing at least one microbe to a magnetic field, and contacting the at least one microbe with at least one nanoparticle including iron.

In various embodiments, the present invention provides a method of antimicrobial treatment. The method includes exposing at least one microbe to an oscillating magnetic field. The method also includes contacting the at least one microbe with at least one nanoparticle including $Fe_3O_4$.

In various embodiments, the present invention provides a composition for antimicrobial treatment. The composition includes at least one nanoparticle including iron.

BRIEF DESCRIPTION OF THE FIGURES

The patent or application file contains at least one drawing executed in color. Copies of this patent or patent application publication with color drawing(s) will be provided by the Office upon request and payment of the necessary fee.

The drawings illustrate generally, by way of example, but not by way of limitation, various embodiments discussed in the present document.

FIGS. 2A-2D illustrate methods of biofilm exposure to magnetic fields, in accordance with various embodiments.

FIG. 8 illustrates biofilm colonies on infected tissue with viscous mucus layer characteristic of an infection in cystic fibrosis respiratory tract, showing inability of the drug to penetrate the barriers.

DETAILED DESCRIPTION OF THE INVENTION

Figure 1:
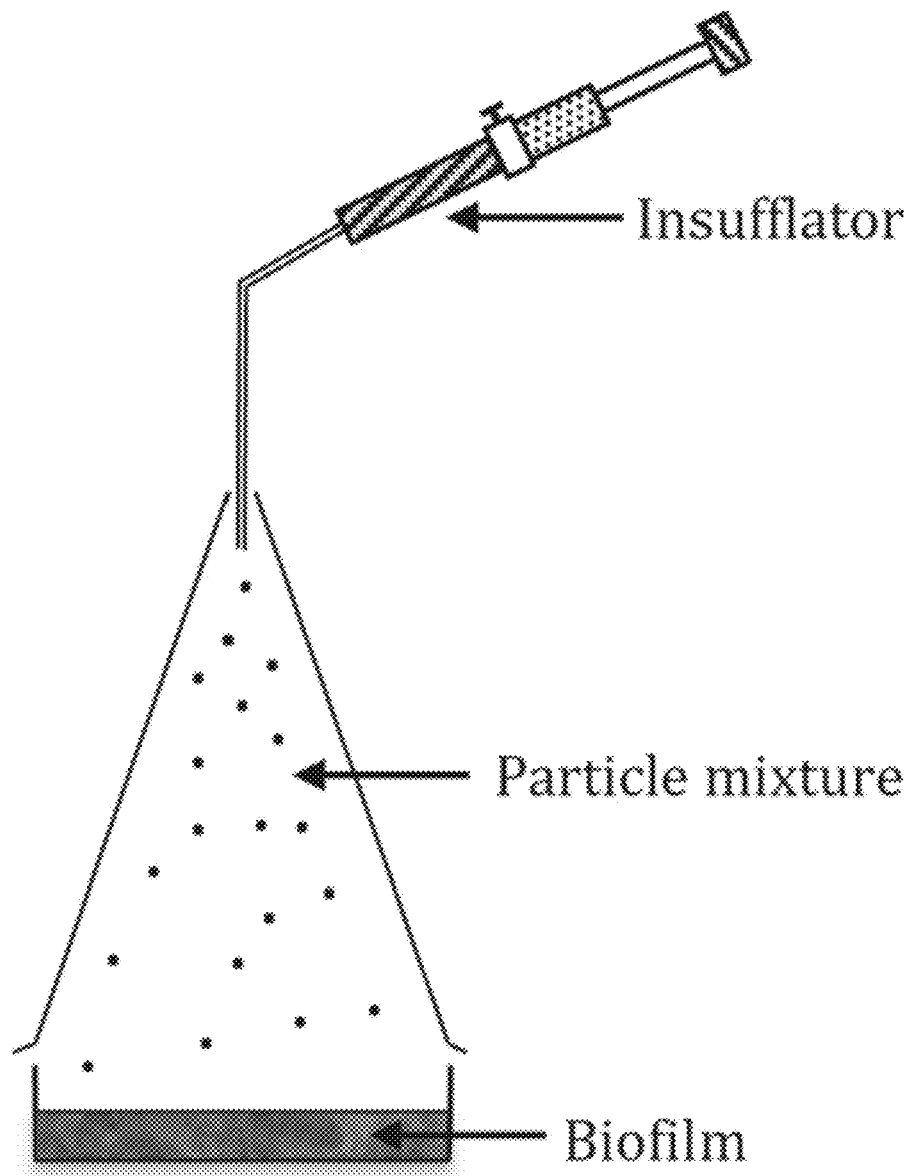
FIG. 1 illustrates a method of biofilm treatment with different particles, in accordance with various embodiments.

Reference will now be made in detail to certain embodiments of the disclosed subject matter, examples of which are illustrated in part in the accompanying drawings. While the disclosed subject matter will be described in conjunction with the enumerated claims, it will be understood that the exemplified subject matter is not intended to limit the claims to the disclosed subject matter.

Values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

In this document, the terms "a," "an," or "the" are used to include one or more than one unless the context clearly dictates otherwise. The term "or" is used to refer to a nonexclusive "or" unless otherwise indicated. The statement "at least one of A and B" has the same meaning as "A, B, or A and B." In addition, it is to be understood that the phraseology or terminology employed herein, and not otherwise defined, is for the purpose of description only and not of limitation. Any use of section headings is intended to aid reading of the document and is not to be interpreted as limiting; information that is relevant to a section heading may occur within or outside of that particular section. All publications, patents, and patent documents referred to in this document are incorporated by reference herein in their entirety, as though individually incorporated by reference. In the event of inconsistent usages between this document and those documents so incorporated by reference, the usage in the incorporated reference should be considered supplementary to that of this document; for irreconcilable inconsistencies, the usage in this document controls.

In the methods of manufacturing described herein, the acts can be carried out in any order without departing from the principles of the invention, except when a temporal or operational sequence is explicitly recited. Furthermore, specified acts can be carried out concurrently unless explicit claim language recites that they be carried out separately. For example, a claimed act of doing X and a claimed act of doing Y can be conducted simultaneously within a single operation, and the resulting process will fall within the literal scope of the claimed process.

The term "about" as used herein can allow for a degree of variability in a value or range, for example, within 10%, within 5%, or within 1% of a stated value or of a stated limit of a range, and includes the exact stated value or range.

The term "substantially" as used herein refers to a majority of, or mostly, as in at least about 50%, 60%, 70%, 80%, 90%, 95%, 96%, 97%, 98%, 99%, 99.5%, 99.9%, 99.99%, or at least about 99.999% or more, or 100%.

The term "organic group" as used herein refers to any carbon-containing functional group. Examples can include an oxygen-containing group such as an alkoxy group, aryloxy group, aralkyloxy group, oxo(carbonyl) group; a carboxyl group including a carboxylic acid, carboxylate, and a carboxylate ester; a sulfur-containing group such as an alkyl and aryl sulfide group; and other heteroatom-containing groups. Non-limiting examples of organic groups include OR, OOR, OC(O)N(R)$_2$, CN, CF$_3$, OCF$_3$, R, C(O), methylenedioxy, ethylenedioxy, N(R)$_2$, SR, SOR, SO$_2$R, SO$_2$N(R)$_2$, SO$_3$R, C(O)R, C(O)C(O)R, C(O)CH$_2$C(O)R, C(S)R, C(O)OR, OC(O)R, C(O)N(R)$_2$, OC(O)N(R)$_2$, C(S)N(R)$_2$, (CH$_2$)$_{0-2}$N(R)C(O)R, (CH$_2$)$_{0-2}$N(R)N(R)$_2$, N(R)N(R)C(O)R, N(R)N(R)C(O)OR, N(R)N(R)CON(R)$_2$, N(R)SO$_2$R, N(R)SO$_2$N(R)$_2$, N(R)C(O)OR, N(R)C(O)R, N(R)C(S)R, N(R)C(O)N(R)$_2$, N(R)C(S)N(R)$_2$, N(COR)COR, N(OR)R, C(=NH)N(R)$_2$, C(O)N(OR)R, C(=NOR)R, and substituted or unsubstituted (C$_1$-C$_{100}$)hydrocarbyl, wherein R can be hydrogen (in examples that include other carbon atoms) or a carbon-based moiety, and wherein the carbon-based moiety can be substituted or unsubstituted.

The term "substituted" as used herein in conjunction with a molecule or an organic group as defined herein refers to the state in which one or more hydrogen atoms contained therein are replaced by one or more non-hydrogen atoms. The term "functional group" or "substituent" as used herein refers to a group that can be or is substituted onto a molecule or onto an organic group. Examples of substituents or functional groups include, but are not limited to, a halogen (e.g., F, Cl, Br, and I); an oxygen atom in groups such as hydroxy groups, alkoxy groups, aryloxy groups, aralkyloxy groups, oxo(carbonyl) groups, carboxyl groups including carboxylic acids, carboxylates, and carboxylate esters; a sulfur atom in groups such as thiol groups, alkyl and aryl sulfide groups, sulfoxide groups, sulfone groups, sulfonyl groups, and sulfonamide groups; a nitrogen atom in groups such as amines, hydroxyamines, nitriles, nitro groups, N-oxides, hydrazides, azides, and enamines; and other heteroatoms in various other groups. Non-limiting examples of substituents that can be bonded to a substituted carbon (or other) atom include F, Cl Br, I, OR, OC(O)N(R)$_2$, CN, NO, NO$_2$, ONO$_2$, azido, CF$_3$, OCF$_3$, R, O (oxo), S (thiono), C(O), S(O), methylenedioxy, ethylenedioxy, N(R)$_2$, SR, SOR, SO$_2$R, SO$_2$N(R)$_2$, SO$_3$R, C(O)R, C(O)C(O)R, C(O)CH$_2$C(O)R, C(S)R, C(O)OR, OC(O)R, C(O)N(R)$_2$, OC(O)N(R)$_2$, C(S)N(R)$_2$, (CH$_2$)$_{0-2}$N(R)C(O)R, (CH$_2$)$_{0-2}$N(R)N(R)$_2$, N(R)N(R)C(O)R, N(R)N(R)C(O)OR, N(R)N(R)CON(R)$_2$, N(R)SO$_2$R, N(R)SO$_2$N(R)$_2$, N(R)C(O)OR, N(R)C(O)R, N(R)C(S)R, N(R)C(O)N(R)$_2$, N(R)C(S)N(R)$_2$, N(COR)COR, N(OR)R, C(=NH)N(R)$_2$, C(O)N(OR)R, and C(=NOR)R, wherein R can be hydrogen or a carbon-based moiety; for example, R can be hydrogen, (C$_1$-C$_{100}$)hydrocarbyl, alkyl, acyl, cycloalkyl, aryl, aralkyl, heterocyclyl, heteroaryl, or heteroarylalkyl; or wherein two R groups bonded to a nitrogen atom or to adjacent nitrogen atoms can together with the nitrogen atom or atoms form a heterocyclyl.

The term "alkyl" as used herein refers to straight chain and branched alkyl groups and cycloalkyl groups having from 1 to 40 carbon atoms, 1 to about 20 carbon atoms, 1 to 12 carbons or, in some embodiments, from 1 to 8 carbon atoms. Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, t-butyl, neopentyl, isopentyl, and 2,2-dimethylpropyl groups. As used herein, the term "alkyl" encompasses n-alkyl, isoalkyl, and anteisoalkyl groups as well as other branched chain forms of alkyl. Representative substituted alkyl groups can be substituted one or more times with any of the groups listed herein, for example, amino, hydroxy, cyano, carboxy, nitro, thio, alkoxy, and halogen groups.

The term "alkenyl" as used herein refers to straight and branched chain and cyclic alkyl groups as defined herein, except that at least one double bond exists between two carbon atoms. Thus, alkenyl groups have from 2 to 40 carbon atoms, or 2 to about 20 carbon atoms, or 2 to 12 carbon atoms or, in some embodiments, from 2 to 8 carbon atoms. Examples include, but are not limited to vinyl, —CH=CH(CH$_3$), —CH=C(CH$_3$)$_2$, —C(CH$_3$)=CH$_2$, —C(CH$_3$)=CH(CH$_3$), —C(CH$_2$CH$_3$)=CH$_2$, cyclohexenyl, cyclopentenyl, cyclohexadienyl, butadienyl, pentadienyl, and hexadienyl among others.

The term "acyl" as used herein refers to a group containing a carbonyl moiety wherein the group is bonded via the carbonyl carbon atom. The carbonyl carbon atom is also bonded to another carbon atom, which can be part of an alkyl, aryl, aralkyl cycloalkyl, cycloalkylalkyl, heterocyclyl, heterocyclylalkyl, heteroaryl, heteroarylalkyl group or the like. In the special case wherein the carbonyl carbon atom is bonded to a hydrogen, the group is a "formyl" group, an acyl group as the term is defined herein. An acyl group can include 0 to about 12-20 or 12-40 additional carbon atoms bonded to the carbonyl group. An acyl group can include double or triple bonds within the meaning herein. An acryloyl group is an example of an acyl group. An acyl group can also include heteroatoms within the meaning herein. A nicotinoyl group (pyridyl-3-carbonyl) is an example of an acyl group within the meaning herein. Other examples include acetyl, benzoyl, phenylacetyl, pyridylacetyl, cinnamoyl, and acryloyl groups and the like. When the group containing the carbon atom that is bonded to the carbonyl carbon atom contains a halogen, the group is termed a "haloacyl" group. An example is a trifluoroacetyl group.

The term "aryl" as used herein refers to cyclic aromatic hydrocarbons that do not contain heteroatoms in the ring. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain about 6 to about 14 carbons in the ring portions of the groups. Aryl groups can be unsubstituted or substituted, as defined herein. Representative substituted aryl groups can be mono-substituted or substituted more than once, such as, but not limited to, 2-, 3-, 4-, 5-, or 6-substituted phenyl or 2-8 substituted naphthyl groups, which can be substituted with carbon or non-carbon groups such as those listed herein.

The term "alkoxy" as used herein refers to an oxygen atom connected to an alkyl group, including a cycloalkyl group, as are defined herein. Examples of linear alkoxy groups include but are not limited to methoxy, ethoxy, propoxy, butoxy, pentyloxy, hexyloxy, and the like. Examples of branched alkoxy include but are not limited to isopropoxy, sec-butoxy, tert-butoxy, isopentyloxy, isohexyloxy, and the like. Examples of cyclic alkoxy include but are not limited to cyclopropyloxy, cyclobutyloxy, cyclopentyloxy, cyclohexyloxy, and the like. An alkoxy group can include one to about 12-20 or about 12-40 carbon atoms bonded to the oxygen atom, and can further include double or triple bonds, and can also include heteroatoms. For example, an allyloxy group is an alkoxy group within the meaning herein. A methoxyethoxy group is also an alkoxy group within the meaning herein, as is a methylenedioxy group in a context where two adjacent atoms of a structure are substituted therewith.

The term "amine" as used herein refers to primary, secondary, and tertiary amines having, e.g., the formula N(group)$_3$ wherein each group can independently be H or non-H, such as alkyl, aryl, and the like. Amines include but are not limited to R—NH$_2$, for example, alkylamines, arylamines, alkylarylamines; R$_2$NH wherein each R is independently selected, such as dialkylamines, diarylamines, aralkylamines, heterocyclylamines and the like; and R$_3$N wherein each R is independently selected, such as trialkylamines, dialkylarylamines, alkyldiarylamines, triarylamines, and the like. The term "amine" also includes ammonium ions as used herein.

The term "amino group" as used herein refers to a substituent of the form —NH$_2$, —NHR, —NR$_2$, —NR$_3^+$, wherein each R is independently selected, and protonated forms of each, except for —NR$_3^+$, which cannot be protonated. Accordingly, any compound substituted with an amino group can be viewed as an amine. An "amino group" within the meaning herein can be a primary, secondary, tertiary, or quaternary amino group. An "alkylamino" group includes a monoalkylamino, dialkylamino, and trialkylamino group.

The terms "halo," "halogen," or "halide" group, as used herein, by themselves or as part of another substituent, mean, unless otherwise stated, a fluorine, chlorine, bromine, or iodine atom.

The term "haloalkyl" group, as used herein, includes mono-halo alkyl groups, poly-halo alkyl groups wherein all halo atoms can be the same or different, and per-halo alkyl groups, wherein all hydrogen atoms are replaced by halogen atoms, such as fluoro. Examples of haloalkyl include trifluoromethyl, 1,1-dichloroethyl, 1,2-dichloroethyl, 1,3-dibromo-3,3-difluoropropyl, perfluorobutyl, and the like.

The term "hydrocarbon" as used herein refers to a functional group or molecule that includes carbon and hydrogen atoms. The term can also refer to a functional group or molecule that normally includes both carbon and hydrogen atoms but wherein all the hydrogen atoms are substituted with other functional groups.

The term "number-average molecular weight" as used herein refers to the ordinary arithmetic mean of the molecular weight of individual molecules in a sample. It is defined as the total weight of all molecules in a sample divided by the total number of molecules in the sample. Experimentally, the number-average molecular weight ($M_n$) is determined by analyzing a sample divided into molecular weight fractions of species i having $n_i$ molecules of molecular weight $M_i$ through the formula $M_n = \Sigma M_i n_i / \Sigma n_i$. The number-average molecular weight can be measured by a variety of well-known methods including gel permeation chromatography, spectroscopic end group analysis, and osmometry. If unspecified, molecular weights of polymers given herein are number-average molecular weights.

As used herein, the term "hydrocarbyl" refers to a functional group derived from a straight chain, branched, or cyclic hydrocarbon, and can be alkyl, alkenyl, alkenyl, aryl, cycloalkyl, acyl, or any combination thereof.

The term "solvent" as used herein refers to a liquid that can dissolve a solid, liquid, or gas. Nonlimiting examples of solvents are silicones, organic compounds, water, alcohols, ionic liquids, and supercritical fluids.

The term "room temperature" as used herein refers to a temperature of about 15° C. to 28° C.

Method of Antimicrobial Treatment.

In various embodiments, the present invention provides a method of antimicrobial treatment. The method includes a) exposing at least one microbe to a magnetic field, b) contacting the at least one microbe with at least one nanoparticle including iron, or c) both a) and b). The method can include the exposing of the microbe to the magnetic field, wherein the method is free of the contacting of the microbe with the at least one nanoparticle. The method can include the contacting of the microbe with the nanoparticle, wherein the method is free of the exposing of the microbe to the magnetic field. The method can include the exposing of the microbe to the magnetic field and the contacting of the microbe with the nanoparticle. The method of antimicrobial treatment can be sufficient to kill the microbe.

The method can be performed in any suitable location. The method can be performed in vitro. The method can be performed in vivo. The method can be a method of biofilm treatment, wherein the at least one microbe is incorporated in a biofilm.

The exposing of the microbe to the magnetic field and the contacting of the microbe with the nanoparticle can occur at any time with respect to one another. The exposing of the microbe to the magnetic field and the contacting of the microbe with the nanoparticle can occur at least partially simultaneously. The exposing of the microbe to the magnetic field and the contacting of the microbe with the nanoparticle occur substantially simultaneously. The duration of the exposure of the microbe to the magnetic field or the contacting of the microbe with the nanoparticle can independently occur for any suitable time period, such as for a period of about 0.01 second to about 4 weeks, about 1 minute to about 1 day, about 0.01 seconds or less, or less than, equal to, or greater than about 0.1 s, 1, 2, 3, 4, 5, 6, 8, 10, 12, 14, 16, 18, 20, 25, 30, 35, 40, 45, 50, 55 s, 1 min, 2, 3, 4, 5, 6, 8, 10, 12, 14, 16, 18, 20, 25, 30, 35, 40, 45, 50, 55 min, 1 h, 2, 3, 4, 5, 6, 8, 10, 12, 14, 16, 18, 20, 22 h, 1 d, 2, 3, 4, 5, 6, 8, 10, 12 d, 2 weeks, 3, or about 4 weeks or more. The exposing of the microbe to the magnetic field can include exposing the nanoparticle to the magnetic field.

The contacting of the microbe with the nanoparticle can be performed in any suitable way. In some embodiments, the method can include spraying the nanoparticle on the microbe (e.g., onto a surface that includes the microbe, such as a biofilm surface).

The at least one microbe can be any suitable microbe, such that the method can be carried out as described herein. The at least one microbe can be at least one of grain positive and grain negative. The at least one microbe can be at least one of a bacteria and a fungus. The at least one microbe can be at least one of *Staphylococcus epidermidis, Staphylococcus aureus, Streptococcus* spp, *Pseudomonas aeruginosa, Burkholderia cepacia, Candida* spp, *Escherichia coli, Streptococcus mutans, Rubus fruticosus, Shewanella oneidensis, Saccharomyces cerevisiae, Bacillus anthracis, Bacillus circulans, Micrococcus luteus, Pseudomonas fluorescens, Salmonella enteritidis, Serratia marcescens, Hordeum vulgare, Mycobacterium tuberculosis, Ervinia carotovora, Streptomyces scabies, Haemophilus* spp., *Bordetella pertussis, Coxiella burnetii, Klebsiella pneumonia, Mycoplasma pneumonia, Chlamydophila pneumonia, Legionella pneumophila, Moraxella catarrhalis, Yersinia pestis, Heliobacterium pylori*, and *Alternaria solani*. The at least one microbe can be *Pseudomonas aeruginosa*.

The exposing of the microbe to the magnetic field and the contacting of the microbe with the nanoparticle can independently occur at any suitable temperature, such as about −100° C. to about 100° C., or about −100° C. or less, or less than, equal to, or greater than about −90° C., −80, −70, −60, −50, −40, −30, −20, −10, 0, 10, 20, 30, 40, 50, 60, 70, 80, 90° C., or about 100° C. or more.

The magnetic field can be any suitable magnetic field. The magnetic field can include at least one of a static magnetic field, a time-varying magnetic field, and a magnetic field that oscillates in polarity. The oscillating magnetic field can have an oscillation of about 0.01 kHz/100 Oe to about 10,000,000 kHz/100 Oe, or about 0.01 kHz/100 Oe or less, or less than, equal to, or greater than about 0.1 kHz/100 Oe, 1, 2, 3, 4, 5, 10, 20, 25, 50, 75, 100, 125, 150, 200, 250, 500, 750, 1,000, 1,500, 2,000, 2,500, 5,000, 10,000, 20,000, 50,000, 100,000, 250,000, 500,000, 1,000,000, 5,000,000, or about 10,000,000 kHz/100 Oe or more.

The oscillating magnetic field can be an alternating magnetic field. The oscillating magnetic field can be a switched magnetic field. The magnetic field can be switched every about 0.01 to about 20 h, or about 1 minute to about 120 minutes, or about 0.01 h or less, or less than, equal to, or greater than about 0.1 s, 1, 2, 3, 4, 5, 6, 8, 10, 12, 14, 16, 18, 20, 25, 30, 35, 40, 45, 50, 55 s, 1 min, 2, 3, 4, 5, 6, 8, 10, 12, 14, 16, 18, 20, 25, 30, 35, 40, 45, 50, 55 min, 1 h, 2, 3, 4, 5, 6, 8, 10, 12, 14, 16, 18 h, or about 20 h or more.

The magnetic field can have any suitable strength, such as a strength of 0.001 kGs to about 10,000,000 kGs, about 0.01 kGs to about 10 kGs, about 0.001 kGs or less, or less than, equal to, or greater than about 0.01 kGs, 0.1, 1, 2, 3, 4, 5, 10, 20, 25, 50, 75, 100, 125, 150, 200, 250, 500, 750, 1,000, 1,500, 2,000, 2,500, 5,000, 10,000, 20,000, 50,000, 100,000, 250,000, 500,000, 1,000,000, 5,000,000, or about 10,000,000 kGs or more.

The nanoparticle can be any suitable nanoparticle. The nanoparticle can be a magnetic nanoparticle. The iron in the nanoparticle can be at least one of iron oxide and zero-valent iron. The iron in the nanoparticle can be part of an iron compound that is at least one of FeO, $Fe_3O_4$, $Fe_4O_5$, $Fe_2O_3$. The iron in the nanoparticle can be part of an iron compound that is $Fe_3O_4$. The nanoparticle can be a superparamagnetic iron oxide nanoparticle. A ferrofluid can include the nanoparticle.

The nanoparticles can have any suitable concentration during the contacting with the microbe. The concentration of the nanoparticles can be about 0.0001 µg/mL to about 1 g/mL, or about 0.0001 µg/mL or less, or less than, equal to, or greater than about 0.001 µg/mL, 0.01, 0.1, 1 µg/mL, 0.01 mg/mL, 0.1, 1 mg/mL, 0.01 g/mL, 0.1 g/mL, or about 1 g/mL or more.

The nanoparticle can have any suitable size, such as having a largest dimension of about 1 nm to about 999 nm, about 10 nm to about 400 nm, about 1 nm to about 100 nm, or about 1 nm or less, or less than, equal to, or greater than about 2 nm, 3, 4, 5, 6, 8, 10, 12, 14, 16, 18, 20, 25, 30, 35, 40, 45, 50, 60, 70, 80, 90, 100, 125, 150, 175, 200, 250, 300, 400, 500, 600, 700, 800, 900, or about 999 nm or more.

The nanoparticle can include at least one organic substituent thereon. The organic substituent can be any suitable organic substituent. For example, the organic substituent can be or can include a saccharide, a polysaccharide, a poly(oxy (substituted or unsubstituted (C2-C3)alkyl)), or a substituted or unsubstituted ($C_1$-$C_{200}$)hydrocarbyl group interrupted by 0, 1, 2, or 3 groups independently chosen from —O—, —S—, —(O($C_2$-$C_3$)alkylene)$_n$- wherein n is 1 to 1,000, and substituted or unsubstituted —NH—. The organic substituent can be or can include at least one of alginate, chitosan, curdlan, dextran, derivatized dextran, emulsan, a galactoglucopolysaccharide, gellan, glucuronan, N-acetyl-glucosamine, N-acetyl-heparosan, hyaluronic acid, kefiran, lentinan, levan, mauran, pullulan, scleroglucan, schizophyllan, stewartan, succinoglycan, xanthan, diutan, welan, starch, derivatized starch, tamarind, tragacanth, guar gum, derivatized guar gum, gum ghatti, gum arabic, locust bean gum, cellulose, and derivatized cellulose. The organic substituent can be or can include at least one of alginate, polyethyleneglycol, and polyethyleneglycol-COOH. The organic substituent can be or can include a drug. The organic substituent can be or can include an antibiotic.

The nanoparticle can include any suitable number of organic substituents, such as about 1 to about 10,000,000 of the organic substituents, or about 1, or less than, equal to, or greater than about 2, 3, 4, 5, 6, 7, 8, 9, 10, 12, 14, 16, 18, 20, 25, 50, 75, 100, 125, 150, 200, 250, 500, 750, 1,000, 1,500, 2,000, 2,500, 5,000, 10,000, 20,000, 50,000, 100,000, 250,000, 500,000, 1,000,000, 5,000,000, or about 10,000,000 or more.

The nanoparticle can include more than one organic substituent, and at least some of the organic substituents can be crosslinked. The crosslinking can be any suitable crosslinking. The crosslinking can include direct crosslinking between organic substituents or crosslinking between organic substituents via one or more linkers.

In some embodiments, a drug is at least one of crosslinked and conjugated to the organic substituent. Crosslinking between the organic substituent and the drug can be EDC/sulfo-NHS cross-linking.

The method can further include exposing the at least one microbe to at least one antibiotic. The antibiotic can be any suitable antibiotic. The antibiotic can be at least one of ciprofloxacin hydrochloride and tobramycin. The exposing the microbe to the antibiotic can occur at any suitable time with respect to treatment with a magnetic field or treatment with nanoparticles. The exposing of the microbe to the antibiotic can occur at least partially simultaneously with at least one of the exposing of the microbe to the magnetic field and the contacting of the microbe with the nanoparticle. The exposing the microbe to the antibiotic can occur substantially simultaneously with at least one of the exposing of the microbe to the magnetic field and the contacting of the microbe with the nanoparticle.

In various embodiments, the present invention provides a method of antimicrobial treatment. The method can include both a) exposing at least one microbe to an oscillating magnetic field, and b) contacting the at least one microbe with at least one nanoparticle including $Fe_3O_4$.

Composition.

In various embodiments, the present invention provides a composition for antimicrobial treatment. The composition can include at least one of the nanoparticles described herein. The nanoparticle can include iron. The composition can further include a drug, such as an antibiotic.

Coating.

In various embodiments, the present invention provides a coating. The coating can be any suitable coating that includes an embodiment of the composition described herein.

Medical Device.

In various embodiments, the present invention provides a medical device. The medical device can be any suitable medical device that includes an embodiment of the composition or coating described herein.

EXAMPLES

Various embodiments of the present invention can be better understood by reference to the following Examples which are offered by way of illustration. The present invention is not limited to the Examples given herein.

Part I. Static Switched Magnetic Fields Suppress *Pseudoinonas aeruginosa* Biofilms and Enhance the Antipseudomonal Activity of Ciprofloxacin.

Methods. Individual and combination approaches to eliminate *P. aeruginosa* biofilms were assessed in vitro using a standard biofilm assay. 24 h biofilms were exposed to various magnetic fields (Static one sided, Static switched, Oscillating, Static+oscillating). Aerosolized MNPs, Cipro or combination were also assessed in the presence or absence of magnetic fields. The effect of various treatment combinations were quantitatively assessed using changes in bacterial metabolism, biofilm biomass, and qualitatively using confocal laser scanning microscopy (CLSM).

Results. The biofilms exposed to magnetic fields alone, without any MNP or drug treatment, exhibited significant reductions in metabolism and biomass ($P<0.05$). CLSM confirmed the severe destruction of the biofilm structure when exposed to magnetic fields compared to unexposed controls. MNP treatments alone did not yield significant reduction in biofilm metabolism but when biofilms were treated with MNP or Cipro or combination, the most significant reductions of metabolic activity and biomass were observed when exposed to static switched magnetic fields ($P<0.05$).

Conclusion. The exposure of *P. aeruginosa* biofilms to static switched magnetic field alone or co-administration with MNP or Cipro or MNP+Cipro appears to be a promising approach to eradicate *P. aeruginosa* biofilms.

Introduction. Microbial biofilms cause severe infections resulting significant mortality and morbidity. Due to the refractory nature of pathogenic biofilms, innovative biofilm eradication strategies and new therapeutic agents are important for the effective treatment of infectious diseases. The effects of distinct types of magnetic field treatments were investigated in this study in combination with magnetic nanoparticles (MNP), and a model antibiotic agent (ciprofloxacin, Cipro).

Some studies have shown that magnetic nanoparticles (MNP) can be used as a promising treatment modality in cancer therapy, drug carrier or MRI contrasting agent. Due to greater biocompatibility, low systemic toxicity, and the ability to release thermal energy in the presence of oscillating magnetic fields, MNPs such as iron oxides has been receiving ample attention in antitumor therapeutic strategies. Superparamagnetic iron oxide nanoparticles (SPION) can be successfully used in enhancing drug transport in CF mucus and alginate gels. When exposed to magnetic fields, SPIONs demonstrated enhanced penetration in model alginate biofilms.

An emerging treatment strategy, usage of polymeric or inorganic nanoparticles, appears to be a promising approach to eradicate biofilms from tissues and surrounding surfaces. However, there are no reports on co-application of magnetic fields (oscillating, static, and combinations), MNPs, and antibiotics as a biofilm elimination strategy. Thus, the aim of this study was to investigate the efficacy of various magnetic fields in eliminating in vitro *P. aeruginosa* biofilms treated with an aerosolized formulation containing magnetic nanoparticles (MNP), ciprofloxacin (Cipro) and spray dried lactose (SDL).

Materials. Ciprofloxacin (Cipro). Ciprofloxacin hydrochloride USP was purchased from Letco Medical (Alabama, USA, Catalog No. 690953). Magnetic Nanoparticles (MNP). FluidMAG-CMX Superparamagentic iron oxide nanoparticles (SPIONs, 150 nm 40 mg/mL) in distilled water were purchased from Chemicell® (Chemical GmBH, Berlin, Germany). Spray dried lactose (SDL). Spray dried lactose (Super Tab 11SD, Monohydrate lactose USP) was provided by DFE Pharma (Princeton, USA). Microorganisms. *Pseudomonas aeruginosa* PAO1 was used throughout the study. The identity of the bacteria was confirmed with commercially available API 20 E kit (Biomérieux, Mercy I'Etoile, France). All isolates were stored in multiple aliquots at −20° C., after confirming their purity. Growth media. Blood Agar (Sigma Aldrich, USA) and Brain Heart Infusion (BHI, Sigma Aldrich, USA) solution were used for culturing *P. aeruginosa*.

Methods. Microbial inocula. Prior to each experiment, *P. aeruginosa* was subcultured on blood agar for 18 h at 37° C. A loopful of the overnight bacterial growth was inoculated into BHI medium, and incubated for 18 h in an orbital shaker (80 rpm) at 37° C. The resultant bacteria were harvested, washed twice in phosphate buffered saline (PBS, pH 7.2) and resuspended. The concentration of *P. aeruginosa* was adjusted $1 \times 10^7$ cells/ml by spectrophotometry and confirmed by hemocytometric counting.

Biofilm Formation. *P. aeruginosa* biofilms were developed as described by Bandara et al with the following modifications. Commercially available pre-sterilized, polystyrene, flat bottom 96-well microtiter plates (BD Biosciences, Calif., USA) were used. At first, 100 µl of a standard cell suspension of bacteria ($10^7$ organisms/ml) was prepared and transferred into the wells of a microtiter plate, and the plate was incubated for 1.5 h (37° C., 75 rpm) to promote microbial adherence to surface of the wells. After the initial adhesion phase, the cell suspensions were aspirated and each well was washed twice with PBS to remove loosely adherent cells. A total of 200 µl of BHI was transferred to each well and the plate reincubated for 24 h (37° C., 75 rpm), and wells washed twice with PBS to eliminate traces of the medium. The effects of various treatments were studied on such preformed biofilms in a period of 24 h.

Determination of minimum inhibitory concentration (MIC). Planktonic phase. MIC was determined by a broth microdilution assay in accordance with the CLSI guidelines. Briefly, bacterial cell suspensions ($5 \times 10^5$ Cells/ml) were treated with the antibiotic in a concentration gradient (two fold) and incubated in a 96 well microtiter plate for 24 h at 35° C. At the end of the incubation, the optical density of the bacterial growth was measured by a spectrophotometer at 595 nm. The lowest concentration of the antibiotic at which the bacteria demonstrate 80% of visible growth inhibition compared to the solvent control is considered as the MIC of the antibiotic against *P. aeruginosa*. The assay was performed quadruplicates at three times.

Biofilm phase. *P. aeruginosa* biofilms were developed in sterile 96 well plates (BD biosciences, USA) as described above. Biofilms were washed twice with PBS and ciprofloxacin was administered in a concentration gradient (two fold). The plates were incubated for 24 h at 37° C. and 80 rpm. At the end of incubation period, XTT reduction assay was performed to quantify the viability of biofilms. The lowest concentration of the antibiotic at which the bacteria demonstrate 80% of viability compared to the solvent control is considered as the MIC of the antibiotic against *P. aeruginosa*. The assay was performed quadruplicates at three times.

Spray-Drying of formulations. The spray-dried lactose particles loaded with Cipro, MNP, or both were prepared using a Buchi® B-290 mini spray drier (Buchi, Switzerland). Formulations were prepared in 1 g batch for ones with MNPs (SDL+MNP, SDL+MNP+Cipro) and 2.5 g for ones without MNP (SDL, SDL+Cipro).

Cipro and MNP were mixed in 5% and 1% (w/w) in lactose respectively to prepare dry formulations. SDL, SDL+Cipro, SDL+MNP, and SDL+MNP+Cipro formulations were prepared by spray drying. Following parameters were used in the spray drying process; Feed solutions consisted of 2.5% (w/v) lactose in distilled water, inlet temperature 150° C., feed rate 1.8 mL/min, airflow rate ($N_2$/qFlow) 357 L/h, $N_2$ Pressure 80 psi, and aspiration rate 35 m³/h. Sixty one percent, 67% and 77% of SDL+Cipro, SDL+MNP, and SDL+MNP+Cipro were recovered respectively after spray drying.

Figure 2A:
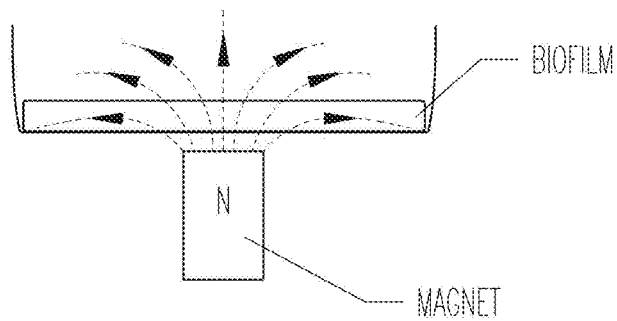
Figure 2B:
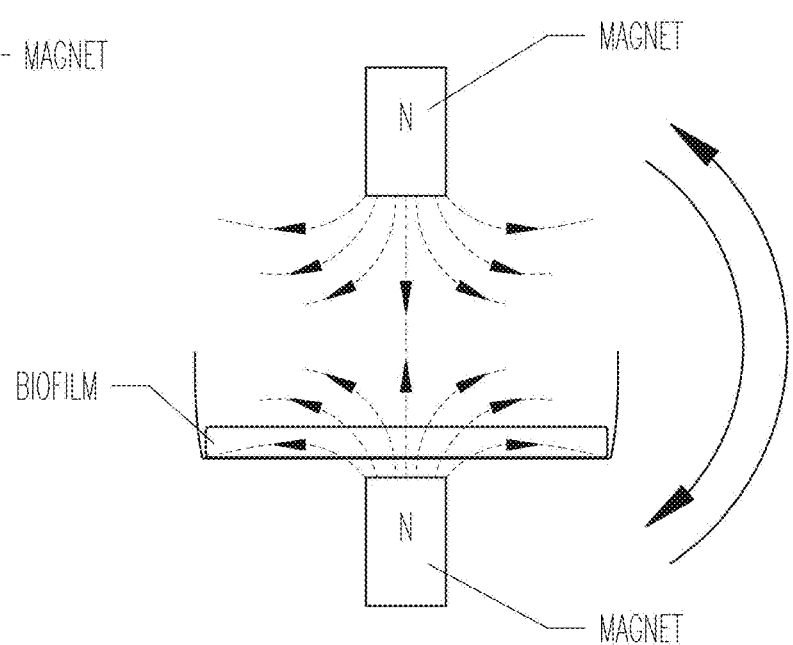
Figure 2C:
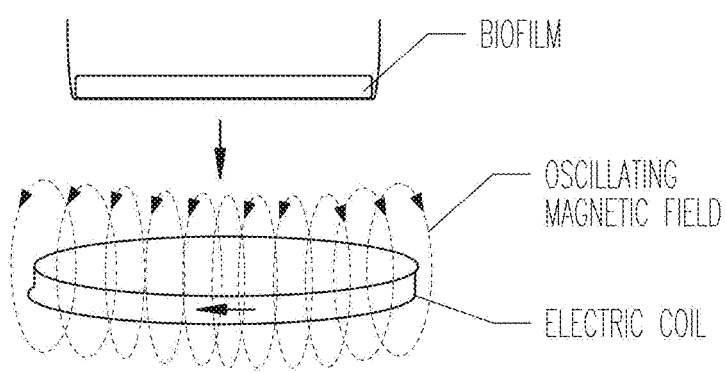

Exposure of biofilms to magnetic fields. Biofilm formation and treatment. *P. aeruginosa* biofilms were developed for 24 h in sterile 6 well plates and tissue culture treated petri dishes (for subsequent Magnatherm treatment) as described above. Twenty-four-hour Biofilms were washed twice with sterile PBS and the physical mixtures of SDL, SDL+Cipro, SDL+MNP, SDL+MNP+Cipro were applied on to biofilm using an aerosol dosing method (FIG. 1). A dry powder insufflator (Model DP-4M, Penn-Century Inc, USA) was used and final Cipro deposition was estimated to be 1 µg/ml (=MIC80 of *P. aeruginosa* biofilms). Subsequently, the plates were exposed to one of 4 different magnetic field treatments. Static magnetic field treatments involved in exposing the 24 h-biofilm, with or without spray dried particles, to magnetic fields from the bottom of the 6-well plate for 6 h using molybdenum magnets (magnetic field strength at the biofilm=4.44 kG, FIG. 2A). Switched static magnetic field treatment involved exposing the 24 h-biofilm, with or without spray dried particles, to magnetic fields from the bottom of the 6 well plates for 30 min (magnetic field strength=4.44 kG) followed by exposing from the top of the 6-well plate for 30 min (magnetic field strength was 0.12 kG) for 6 h of total exposure (FIG. 2B). The oscillating magnetic field treatment involved in exposing the 24 h-biofilm, with or without spray dried particles, to magnetic fields generated by Magnatherm (Biofilms in petri dishes, 17 turn coil of 474 kHz nominal frequency, current supply: 20V, 4.3 A, Nanotherics Magnetherm, UK) for 30 min (FIG. 2C). The Static plus oscillating (Static+oscillating) magnetic field treatment involved in exposing the 24 h-biofilm, with or without spray dried particles, to static magnetic fields as mentioned above for 1 h followed by 30 min exposure to oscillating magnetic fields (FIG. 2D). After magnetic field treatment, biofilms were incubated in 80% humidified incubator for 24 h at 37° C. (FIG. 2D). At the end of incubation period, the biofilms were washed twice with PBS; XTT reduction assay was performed to quantify the viability of biofilms by means of measuring metabolic activity and crystal violet assay to quantify biofilm biomass.

XTT reduction assay. At the end of incubation of both test and control biofilms, a standard XTT (sodium 2,3,-bis(2-methoxy-4-nitro-5-sulfophenyl)-5-[(phenylamino)-carbonyl]-2H-tetrazolium inner salt) reduction assay was performed thereafter as described by Bandara et al to measure the viability of biofilms by means of bacterial cell metabolic activity. In brief, commercially available XTT powder (Sigma, Mo., USA) was dissolved in PBS to a final concentration of 1 mg/ml. Then the solution was filter-sterilized (0.22 µm pore size filter) and stored at −70° C. Freshly prepared 0.4 mM menadione solution was used for XTT reduction assay. XTT solution was thawed and mixed with menadione solution at 20:1 (v/v) immediately before the assay. Thereafter, PBS:XTT:Menadione in 79:20:1 proportion were added into each culture dish containing biofilms and incubated in the dark for 5 h at 37° C. The color changes were measured with a microliter plate reader (Infinite M200 microplate reader, TECAN US Inc, N.C., USA) at 492 nm. All assays were carried out in triplicate on three different occasions.

Crystal violet assay. At the end of incubation of both test and control biofilms, crystal violet assay was performed to quantify biofilm biomass. Biofilms were carefully washed twice with PBS and stained with 1% crystal violet solution for 15 min at 25° C. without shaking. Wells were carefully washed three times with PBS to remove excess stain and air dried in room temperature. Thirty percent acetic acid was added to the wells containing stained biofilms and incubated for 20 min at 25° C. The solution was transferred to a new well plate and optical density was measured at 570 nm.

Confocal Laser Scanning Microscopy. Biofilms were prepared on Sterile cover slips placed in commercially available sterile flat bottom six well plates (Nunclon, Nunc, thermo Fisher scientific, USA) as described above. Pre-formed 24 h biofilms were exposed to magnetic fields and incubated for another 24 h at 37° C. in a humidified incubator. At the end of incubation, the prewashed coverslips were stained with Live and Dead stain (Live/Dead BacLight Bacterial Viability kit, Invitrogen, Eugene, USA). The biofilm was then analyzed by fluorescent microscopy (using confocal laser scanning microscope).

Statistical analysis. Statistical analysis was performed using SPSS software (version 16.0), Mann Whitney U-test was performed to compare the significant differences between corresponding control and test sample of the *P. aeruginosa* biofilms and to compare the significant differences between test samples of the *P. aeruginosa* biofilms under different treatment conditions. A P-value of less than 0.05 was considered statistically significant.

Example 1.1

The Effects of Magnetic Fields on *P. aeruginosa* Biofilms Treated with Control Particles Biofilm metabolism (XTT reduction assay). When the biofilms treated with SDL control particles and treated with various magnetic fields as mentioned above, all test samples exposed to magnetic fields exhibited significant reduction in the metabolic activity compared to untreated (i.e. magnetic field free) biofilm controls (p<0.05, Table 1, FIG. 3A). Comparing the different magnetic field treatments to each other, no significant differences in the mean XTT readings were found.

TABLE 1

Mean XTT ± SD values of *P. aeruginosa* biofilm treated with various particle formulations and exposed to different magnetic fields.

|  | SDL (Mean XTT ± SD) | SDL + MNP (Mean XTT ± SD) | SDL + Cipro (Mean XTT ± SD) | SDL + MNP + Cipro (Mean XTT ± SD) |
|---|---|---|---|---|
| No magnetic exposure | 0.408 ± 0.13 | 0.284 ± 0.08 | 0.268 ± 0.08 | 0.227 ± 0.08 |
| Static one sided | 0.222 ± 0.05 | 0.261 ± 0.03 | 0.201 ± 0.04 | 0.198 ± 0.04 |
| Static switching | 0.206 ± 0.06 | 0.163 ± 0.03 | 0.153 ± 0.04 | 0.160 ± 0.03 |
| Oscillating | 0.214 ± 0.08 | 0.247 ± 0.11 | 0.175 ± 0.03 | 0.227 ± 0.10 |
| Static + oscillating | 0.256 ± 0.09 | 0.218 ± 0.04 | 0.274 ± 0.12 | 0.235 ± 0.07 |

Figure 3A:
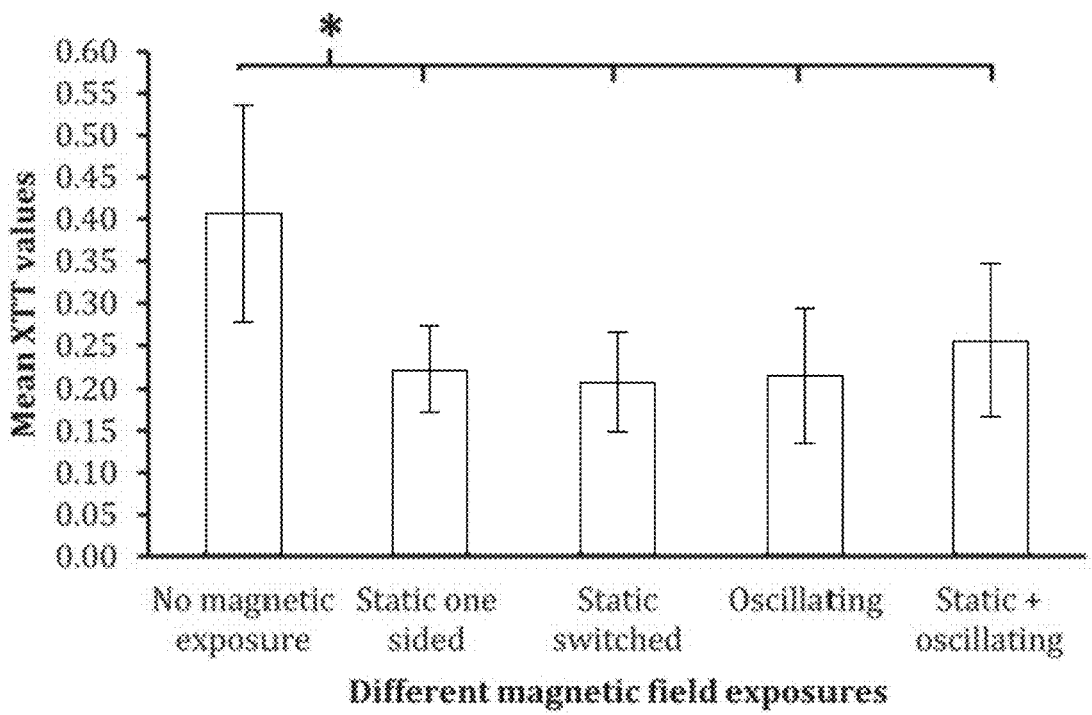
FIG. 3A illustrates the effect of various magnetic fields on mean XTT values of SDL-treated biofilms, in accordance with various embodiments.
Figure 3B:
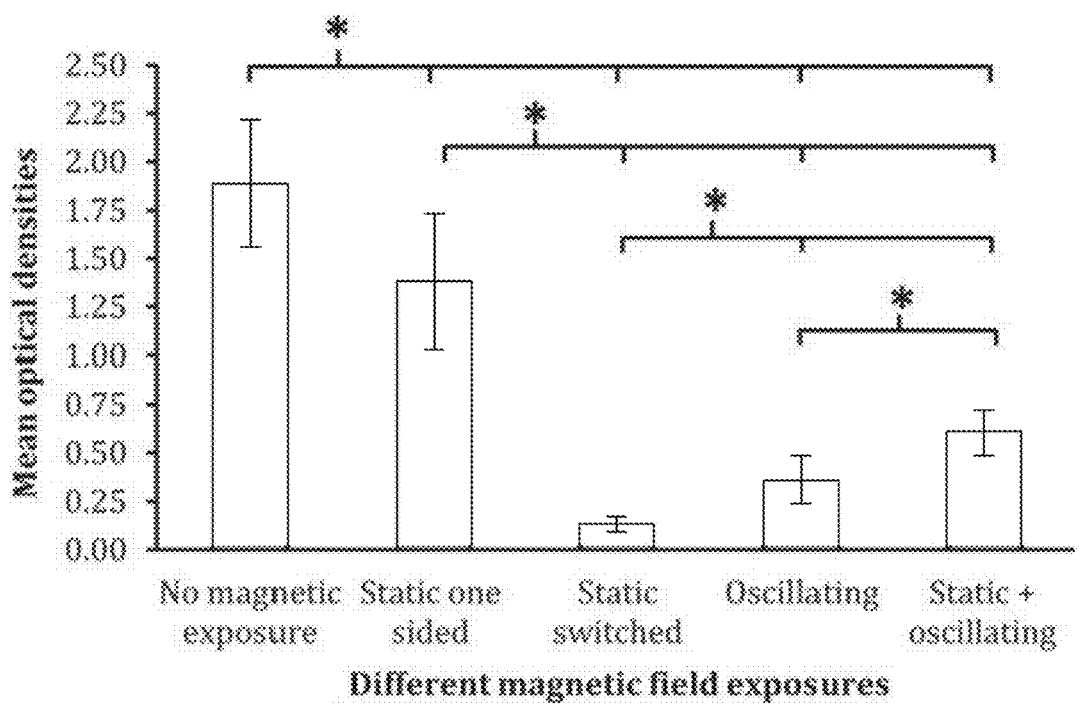
FIG. 3B illustrates the effect of various magnetic fields on mean optical densities of SDL-treated biofilms, in accordance with various embodiments.

FIGS. 3A-G illustrate the effects of various magnetic fields on *P. aeruginosa* biofilms. FIG. 3A illustrates the effect of various magnetic fields on SDL treated biofilms—XTT reduction assay findings; note the significant reduction of biofilm metabolism (Mean XTT values) when exposed to any of the magnetic fields compared to unexposed control. FIG. 3B illustrates the effect of various magnetic fields on SDL treated biofilms—Crystal violet assay findings; note that the most significant reduction of the biomass (mean optical density) was when exposed to static switched magnetic fields. * indicates significant changes and P<0.05 is considered statistically significant.

Biofilm biomass (Crystal Violet assay). When the biofilms were treated with SDL and exposed to one of the four different magnetic fields, all treatments showed a significant reduction of biomass compared to no magnetic field control (p<0.05, Table 2, FIG. 3B). Biofilms exposed to static switched, oscillating and static+oscillating magnetic fields showed a significantly lower biomass compared to the biofilm exposed to static magnetic field (p<0.05, Table 2, FIG. 3B). Biofilms exposed to static switched magnetic field had significantly lower biomass compared to oscillating and static+oscillating magnetic fields (p<0.05, Table 2, FIG. 3B).

TABLE 2

Mean optical density ± SD values of *P. aeruginosa* biofilm treated with various particle formulations and exposed to different magnetic fields.

|  | SDL (Mean OD ± SD) | SDL + MNP (Mean OD ± SD) | SDL + Cipro (Mean OD ± SD) | SDL + MNP + Cipro (Mean OD ± SD) |
|---|---|---|---|---|
| No magnetic exposure | 1.892 ± 0.33 | 0.864 ± 0.28 | 0.952 ± 0.26 | 1.075 ± .27 |
| Static one sided | 1.386 ± 0.35 | 1.382 ± 0.25 | 1.075 ± 0.37 | 0.837 ± 22 |
| Static switching | 0.129 ± 0.04 | 0.230 ± 0.13 | 0.206 ± 0.06 | 0.381 ± 0.06 |
| Oscillating | 0.360 ± 0.12 | 0.264 ± 0.07 | 0.322 ± 0.14 | 0.500 ± 0.26 |
| Static + oscillating | 0.601 ± 0.12 | 0.705 ± 0.13 | 0.452 ± 0.15 | 0.389 ± 0.19 |

Figure 3C:
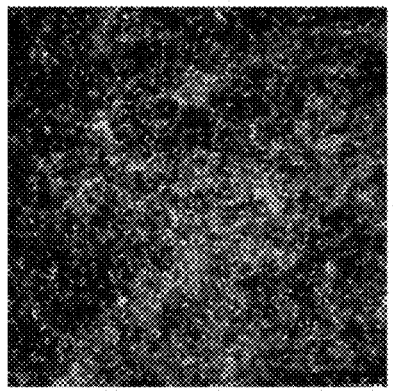
FIGS. 3C-3G illustrate CLSM images of biofilms exposed to different magnetic fields, in accordance with various embodiments.
Figure 3D:
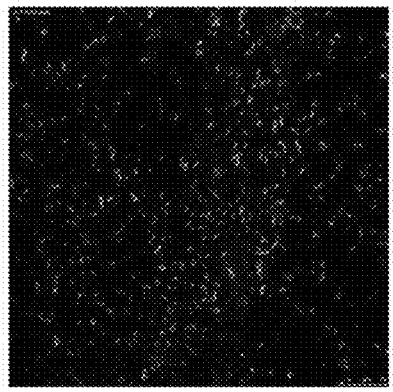
Figure 3E:
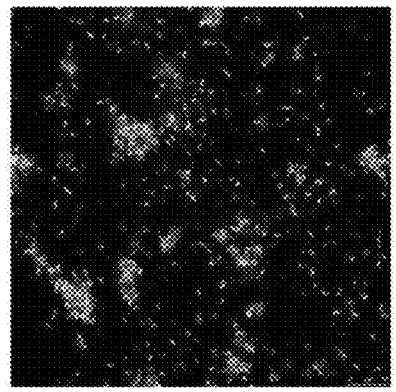
Figure 3F:
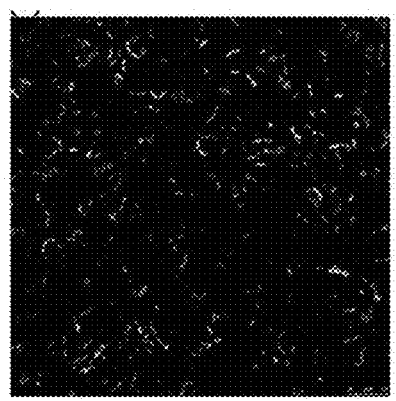
Figure 3G:
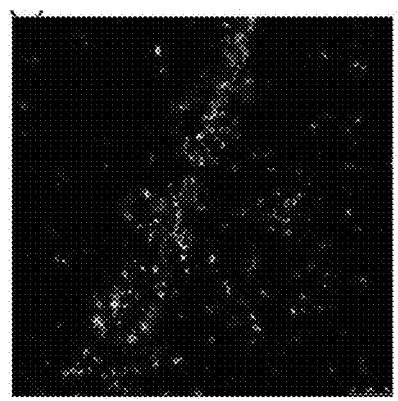

Confocal laser scanning microscopy. FIGS. 3C-G illustrate CLSM images of *P. aeruginosa* biofilms exposed to different magnetic fields (magnification ×40) (stained using a LIVE/DEAD BacLight bacterial viability kit; Invitrogen); live cells are stained in green and dead cells in red. FIG. 3C illustrates an undisturbed control biofilm; FIG. 3D illustrates a biofilm after exposure to static one sided magnetic fields; FIG. 3E illustrates a biofilm after exposure to static alternating magnetic fields; FIG. 3F illustrates a biofilm after exposure to oscillating magnetic fields; FIG. 3G illustrates a biofilm after exposure to static and oscillating magnetic fields. Note the significant reduction of the cellular content, stratified architecture and lower live: dead cell ratio and lack of extracellular components in the test biofilms (FIGS. 3D, 3E, 3F and 3G) compared to three dimensionally arranged and dense biofilm controls with substantial extracellular materials. The control biofilm (FIG. 3C) that was not exposed to magnetic fields demonstrated a dense, spatially oriented and confluent biofilm with substantial amount of extracellular substances and typical live and dead ratio for 24 hour biofilms. The biofilms exposed to static magnetic fields exhibited significantly lower quantity of bacterial cells and there was no organized structure or extracellular substances (FIG. 3D). However, the apparent ratio of live and dead cells did not show significant differences compared to control (FIG. 3D). Similar reduction in bacterial counts was observed in the biofilms exposed to static switched magnetic fields (FIG. 3E). However, the remnants of the biofilm structure were preserved and isolated islands with minimal extracellular materials were observed. The live/dead cell ratio remained similar to the control (FIG. 3E).

Exposure to oscillating magnetic field caused a complete disruption of the biofilm (FIG. 3F). There was no structured biofilm observed in CLSM images. Instead, scattered bacterial cells were visible in the microscopic field with higher proportions of dead cells compared to the control biofilm (FIG. 3F). The biofilm treated with static+oscillating magnetic field also exhibited significantly disrupted biofilm architecture and haphazardly distributed bacterial cells. There were minimal amounts of extracellular matrix compared to the control biofilm (FIG. 3G).

Example 1.2

The Effects of Various Magnetic Fields on P. aeruginosa Biofilms Co-Treated With Magnetic Nanoparticles Biofilm metabolism (XTT reduction assay). When SDL+MNP treated biofilms were exposed to aforementioned different magnetic fields, all test treatments (except those exposed to oscillating magnetic fields) showed significant suppression of biofilm metabolism (p<0.05) compared to untreated biofilm control (Table 1, FIG. 4A). Biofilms that were exposed to static switched magnetic fields demonstrated the lowest metabolic activity and had a significantly lowered metabolic activity compared to biofilms exposed to other magnetic field treatments (p<0.05, Table 1, FIG. 4A).

Figure 4A:
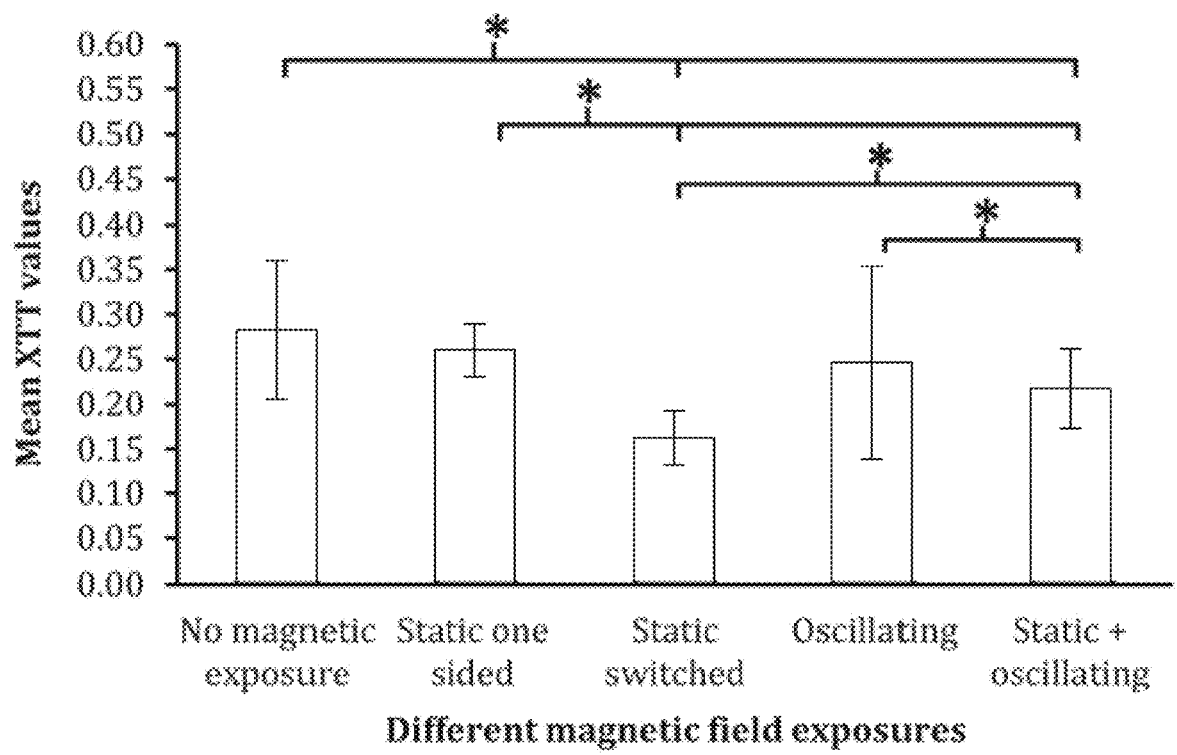
FIG. 4A illustrates mean XTT values for SDL+MNP-treated biofilms exposed to various magnetic fields, in accordance with various embodiments.
Figure 4B:
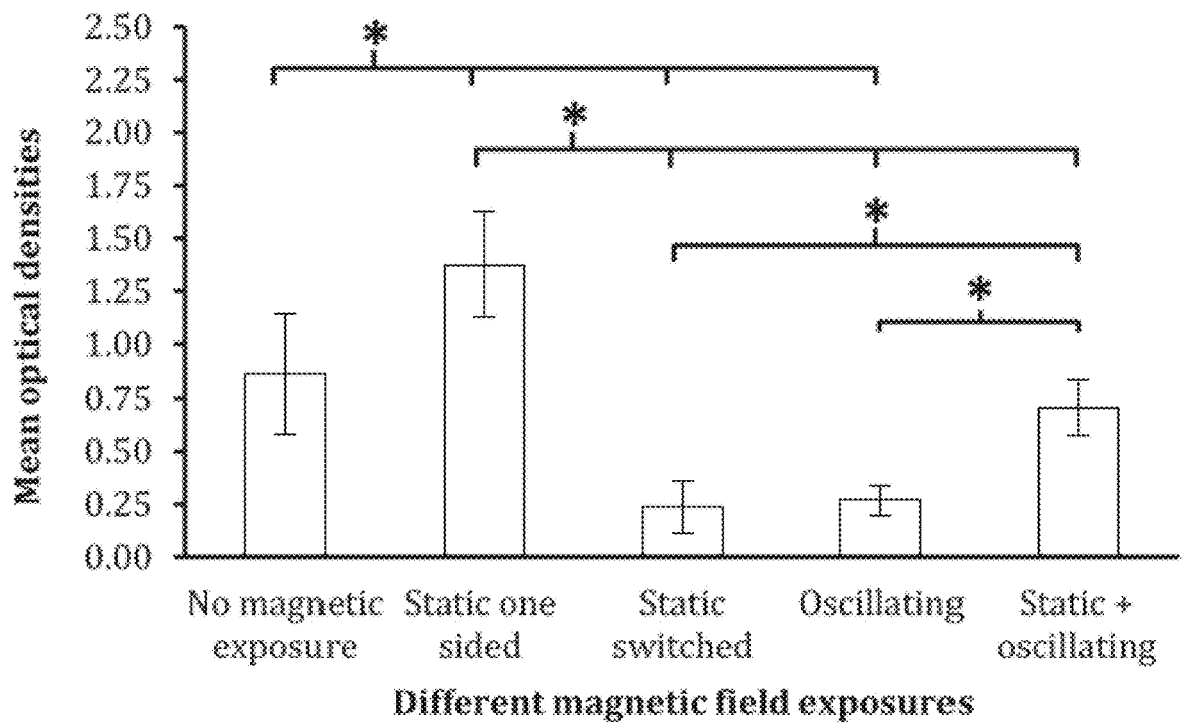
FIG. 4B illustrates mean optical densities for SDL+MNP-treated biofilms exposed to various magnetic fields, in accordance with various embodiments.

FIGS. 4A-B illustrate the effects of various magnetic fields on P. aeruginosa biofilms treated with magnetic nanoparticles. FIG. 4A illustrates the effect of various magnetic fields on SDL+MNP treated biofilms XTT reduction assay findings; note the most significant reduction of biofilm metabolism (Mean XTT values) when exposed to static switched the magnetic fields compared to unexposed control and other exposed biofilms. FIG. 4B illustrates the effect of various magnetic fields on SDL+MNP treated biofilms—Crystal violet assay findings; note that the most significant reduction of the biomass (mean optical density) was when exposed to static switched magnetic fields. * indicates significant changes and P<0.05 is considered statistically significant.

Biofilm biomass (Crystal Violet assay). Biofilms treated with SDL+MNP and exposed to static switched magnetic fields and oscillating magnetic fields showed a significant reduction of their biomass compared to controls and other magnetic field treatments (p<0.05, Table 2, FIG. 4B). Conversely, biofilm exposed to static magnetic fields showed a significantly increased biomass compared to SDL+MNP treated controls (p<0.05, Table 2, FIG. 4B).

Example 1.3

The Effects of Various Magnetic Fields on P. aeruginosa Biofilms Co-Treated with Ciprofloxacin Biofilm metabolism (XTT reduction assay). When P. aeruginosa biofilms were treated with SDL+Cipro and exposed to aforementioned different magnetic fields, all test biofilms except the one exposed to static+oscillating magnetic fields exhibited significant reduction of the metabolism compared to untreated biofilm controls (p<0.05, Table 1, FIG. 5A).

Figure 5A:
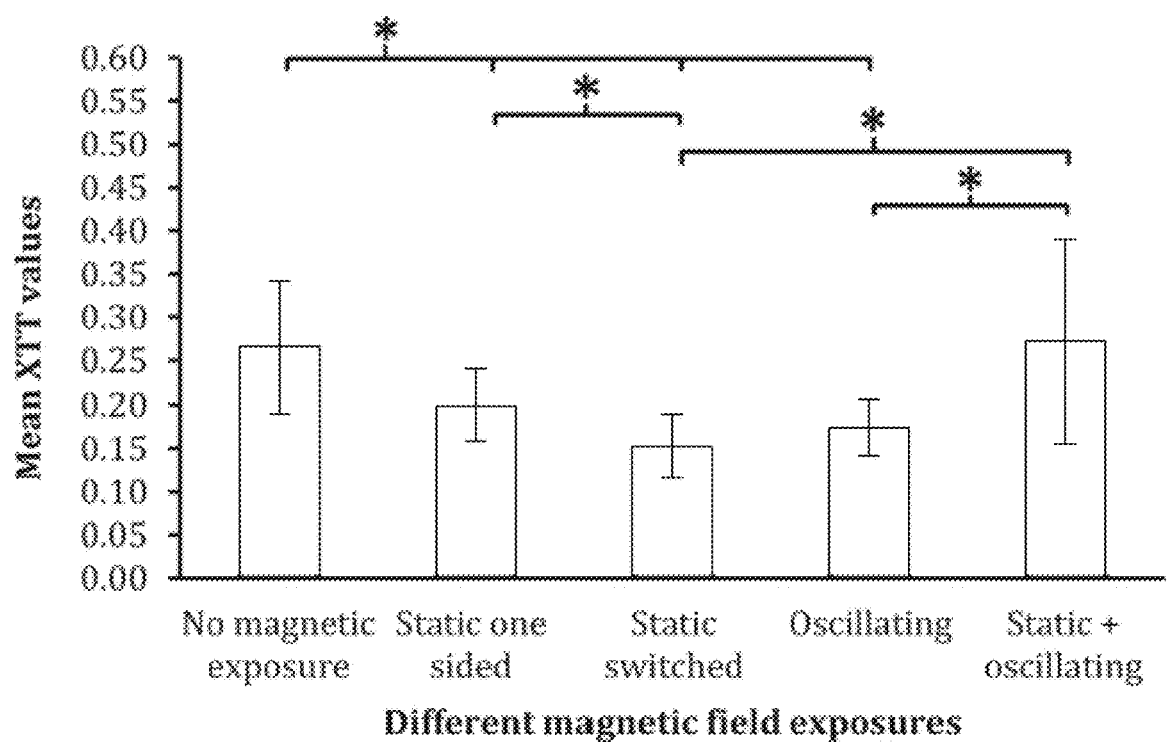
FIG. 5A illustrates mean XTT values for SDL+Cipro-treated biofilms exposed to various magnetic fields, in accordance with various embodiments.
Figure 5B:
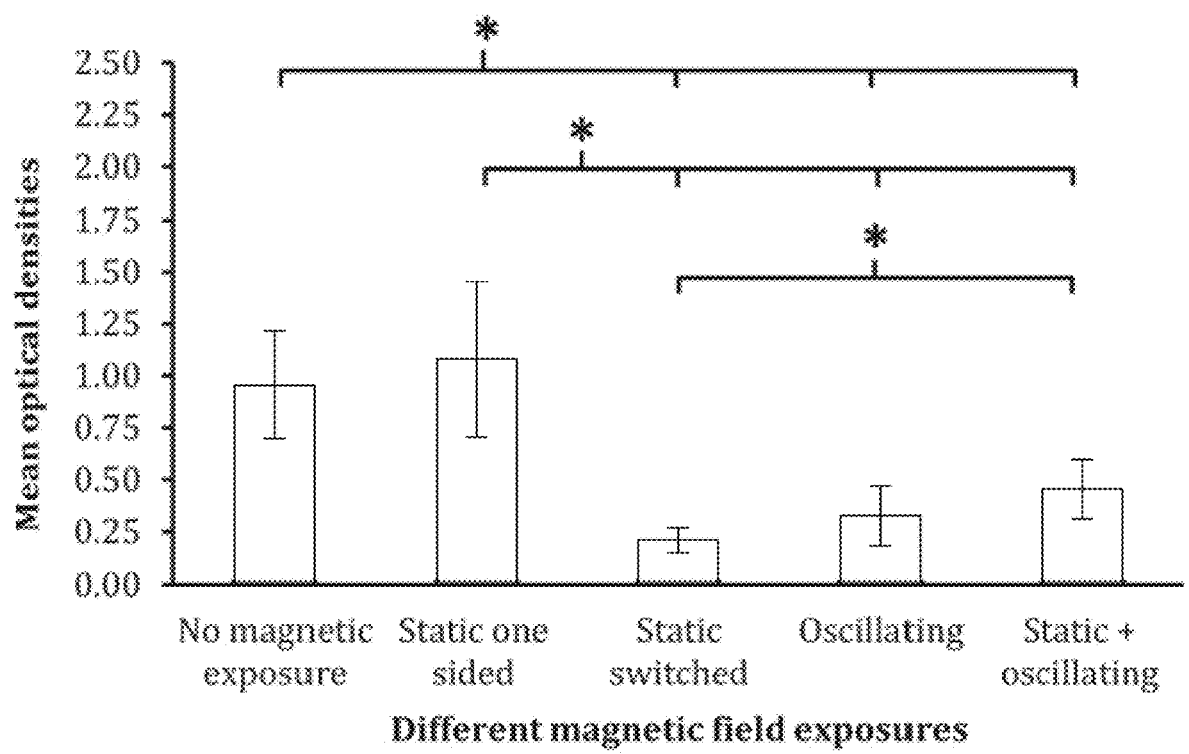
FIG. 5B illustrates mean optical densities for SDL+Cipro-treated biofilms exposed to various magnetic fields, in accordance with various embodiments.

FIGS. 5A-B illustrate the effects of various magnetic fields on P. aeruginosa biofilms treated with ciprofloxacin. FIG. 5A illustrates the effect of various magnetic fields on SDL+Cipro treated biofilms XTT reduction assay findings; note the most significant reduction of biofilm metabolism (Mean XTT values) when exposed to static switched the magnetic fields compared to unexposed control and other exposed biofilms. FIG. 5B illustrates the effect of various magnetic fields on SDL+Cipro treated biofilms—Crystal violet assay findings; note that the most significant reduction of the biomass (mean optical density) was when exposed to static switched magnetic fields. * indicates significant changes and P<0.05 is considered statistically significant.

Biofilm biomass (Crystal Violet assay). Biofilms, co-treated with Cipro and exposed to static switched, oscillating, and static+oscillating magnetic fields exhibited significantly lower biomass compared to controls and the static field treatment (p<0.05, Table 2, FIG. 5B).

Example 1.4

The Effects of Various Magnetic Fields on P. aeruginosa Biofilms Co-Treated With Both Magnetic Nanoparticles and Ciprofloxacin Biofilm metabolism (XTT reduction assay). When P. aeruginosa biofilms were treated with SDL+MNP+Cipro and exposed static switched magnetic fields demonstrated a significant decrease in its metabolism compared to untreated biofilm controls and other magnetic field treatments (p<0.05, Table 1, FIG. 6A). In contrast biofilms were treated with SDL+MNP+Cipro and exposed to other magnetic fields were not significantly different from controls.

Figure 6A:
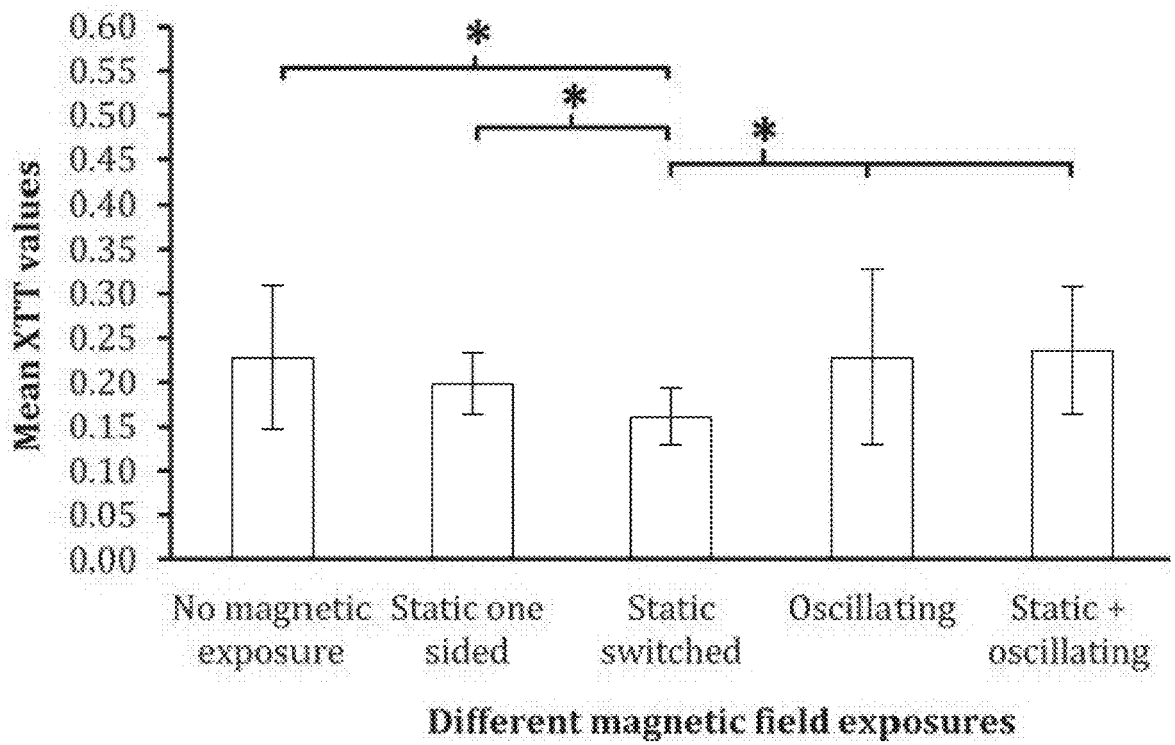
FIG. 6A illustrates mean XTT values for SDL+MNP+Cipro-treated biofilms exposed to various magnetic fields, in accordance with various embodiments.
Figure 6B:
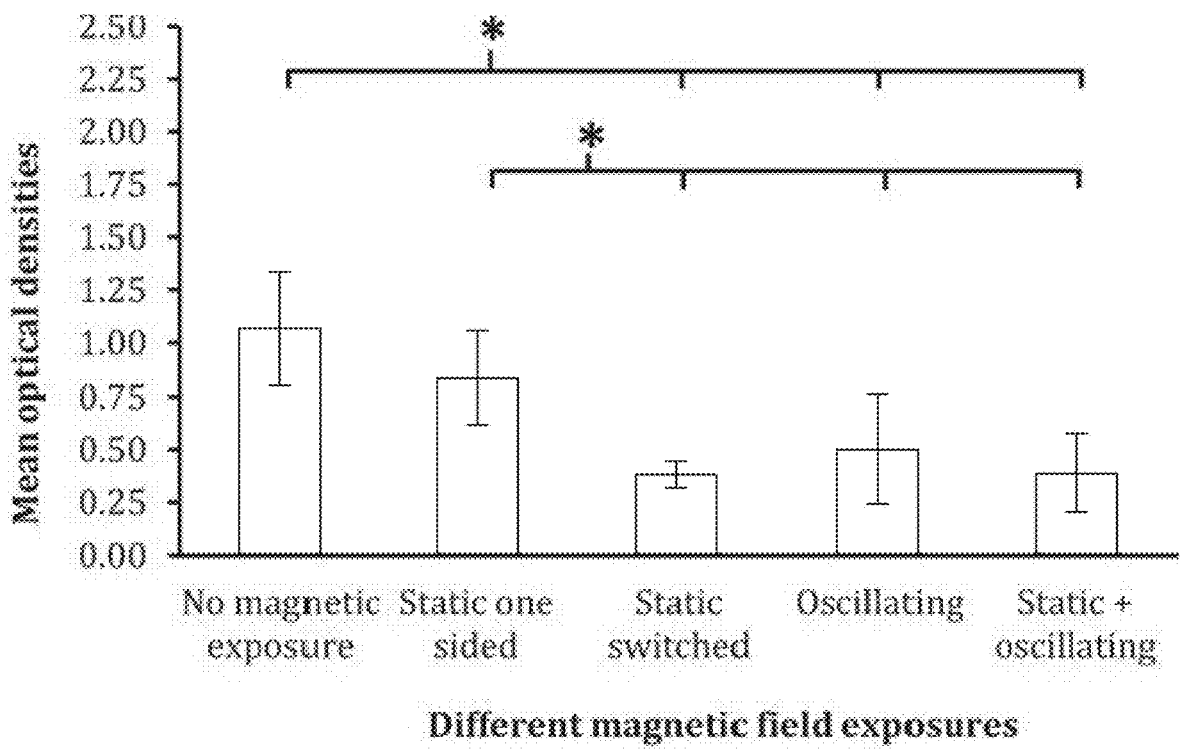
FIG. 6B illustrates mean optical densities for SDL+MNP+Cipro-treated biofilms exposed to various magnetic fields, in accordance with various embodiments.

FIGS. 6A-B illustrate the effects of various magnetic fields on P. aeruginosa biofilms treated with magnetic nanoparticles and ciprofloxacin. FIG. 6A illustrates the effect of various magnetic fields on SDL+MNP+Cipro treated biofilms—XTT reduction assay findings; note the most significant reduction of biofilm metabolism (Mean XTT values) when exposed to static switched the magnetic fields compared to unexposed control and other exposed biofilms FIG. 6B illustrates the effect of various magnetic fields on SDL+MNP+Cipro treated biofilms—Crystal violet assay findings; note that the most significant reduction of the biomass (mean optical density) was when exposed to static switched magnetic fields. * indicates significant changes and P<0.05 is considered statistically significant.

Biofilm biomass (Crystal Violet assay). The outcome of the exposure of SDL+MNP+Cipro treated biofilms to different magnetic fields was compared. All the biofilms exposed to magnetic fields showed a significantly reduced biomass compared to the unexposed sample (p<0.05, Table 2, FIG. 6B). When compared with the biofilm exposed to static magnetic field, the remaining three biofilms exposed to different magnetic fields showed a significant reduction in the biomass (p<0.05, Table 2, FIG. 6B). There were no significant changes among other comparisons.

Example 1.5

The Effects of Various Particle Treatments on *P. aeruginosa*

Biofilm metabolism (XTT reduction assay). When considering the different particle treatments alone (without Magnetic exposure), only SDL+MNP+Cipro treated biofilms showed significantly lower metabolic activity compared to SDL treated control (p<0.05, Table 1, FIG. 7A).

Figure 7A:
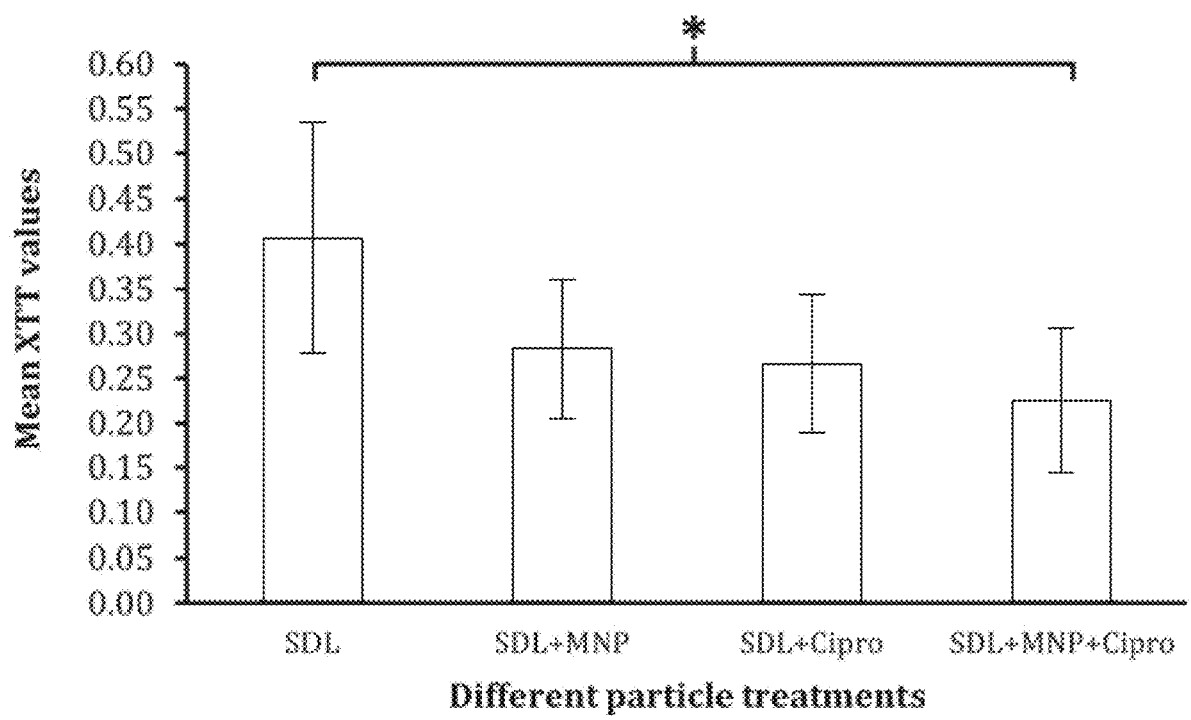
FIG. 7A illustrates mean XTT values for biofilms with various particle treatments, free of magnetic exposure, in accordance with various embodiments.
Figure 7B:
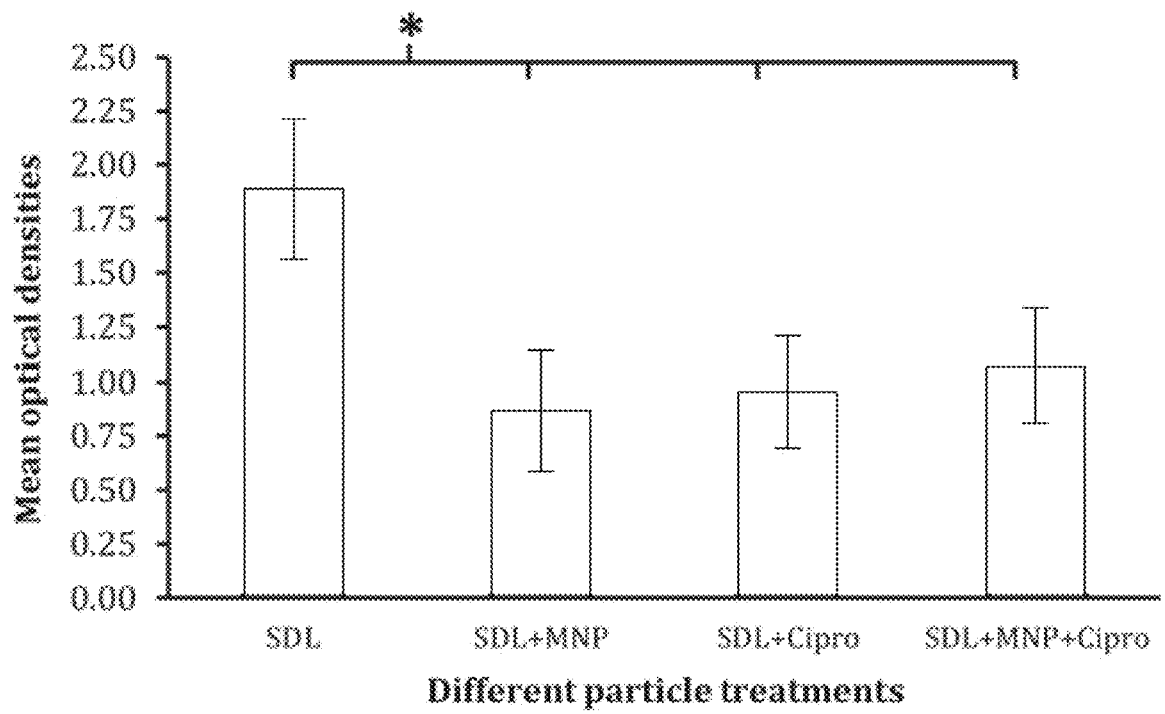
FIG. 7B illustrates mean optical densities for biofilms with various particle treatments, free of magnetic exposure, in accordance with various embodiments.

FIG. 7A-B illustrate the effects of various particle treatments on *P. aeruginosa* biofilms. FIG. 7A illustrates particle treatment of biofilms with no magnetic exposure biofilms XTT reduction assay findings; note the significantly low metabolic activity of the biofilm treated with SDL+MNP+Cipro compared to SDL treated biofilm. FIG. 7B illustrates particle treatment of biofilms with no magnetic exposure—Crystal Violet assay findings; note the significantly low biomass of the biofilm treated with all particle combinations compared to SDL treated biofilm. *indicates significant changes and P<0.05 is considered statistically significant.

In contrast, when different particle treatments exposed to one of the magnetic fields, there were no significant changes observed in any tested biofilms compared to their respective controls (Table 1).

Biofilm biomass (Crystal Violet assay). A significant reduction of the biomass of all three test *P. aeruginosa* biofilms (treated with SDL+MNP, SDL+Cipro and SDL+MNP+Cipro) that were not exposed to test magnetic fields was observed compared to biofilm treated with SDL (P<0.05, Table 2, FIG. 7B).

Example 1.6

Discussion

Due to the refractory nature of pathogenic biofilms, many different biofilm eradication strategies and new therapeutic agents have been investigated. Some strategies have used chemical approaches such as anti-adhesins/polymeric coatings, quorum sensing inhibitors, and biosynthesis inhibitors, biofilm dispersal agents, and natural products, among others. Physical methods have also been investigated including ultrasound waves, low frequency vibrations and others.

Different from previous reports, the current study sought to evaluate the biofilm eradication potential of the combination of chemical and physical approaches. Nanoparticles, a model antibacterial, and magnetic fields were systematically evaluated to assess the relative anti-biofilm contributions of each approach and combinations thereof. The following discussion is organized in increasing order of complexity with initial focus on the separate treatments followed by discussion of the combinations of the treatments. Interestingly, the most effective treatment conditions observed in the present study was obtained using magnetic fields alone.

The Magnetic Fields Alone Disrupt *P. aeruginosa*

Significant reductions in biofilm metabolic activity and biomass were observed when different magnetic fields were applied in the absence of nanoparticle treatments. The highest reduction of the viability and biomass were observed in the biofilm exposed to static switched fields followed by oscillating magnetic fields. The other two magnetic field treatments also exhibited significant results, though those were inferior to static switched and oscillating magnetic fields. The reduction of cell viability must be due to bacterial cell death and reduction in the biomass could possibly be due to both cell death and reduction in the extracellular matrix of the biofilms. Ultrastructural views of biofilms also confirmed the suppressive effects of magnetic fields on *P. aeruginosa* established biofilms. Compared to spatially oriented, confluent, dense control biofilms, the test biofilms exposed to magnetic fields exhibited a severe destruction of the biofilm architecture and showed lower live: dead cell ratio compared to controls. Thus, the magnetic fields appear to disrupt the three dimensional structure of the biofilms as well as negatively affect cell viability. Also, there was a significant reduction in the extracellular matrix in test biofilms compared to control. These findings further suggest that magnetic fields may have an effect on extracellular materials, either on their synthesis or disruption.

There several early reports on the effects of magnetic fields on bacterial growth. Most previous studies have been conducted using static magnetic fields ranging from 30 mT to 14.1 T exposing from 30 min to 6 days using a variety of microbes and growth conditions. After the exposure to static magnetic fields, *E. coli, S. aureus, Streptococcus mutans, rubus fruticosus, Shewanella oneidensis, Saccharomyces cerevisiae, Bacillus circulans, Micrococcus luteus, Pseudomonas fluorescens, Salmonella enteritidis, Serratia marcescens* did not exhibit any significant changes in their growth. The present results, in comparison, demonstrated that static magnetic fields did have a significant inhibitory effect on *P. aeruginosa* biofilm viability and biomass.

As yet few mechanisms have been identified by which magnetic fields may influence microorganism viability and growth. It is suggested that magnetic field effects are likely species, strain, exposure time, strength of magnetic field and growth environment dependent. For instance, the growth inhibition caused by static magnetic fields in *Staphylococcus aureus, Streptococcus mutans* and *E. coli* grown under anaerobic conditions stressed the environment dependent effect of magnetic fields. The effects of magnetic field strength or time of field application was not studied. Thus, the discrepancies between the present study and previous reports may be due to differences in any of the aforementioned conditions.

Magnetic fields may also interact with iron related cellular processes. The growth of mutant *E. coli* K-12 (iron mutant) was significantly reduced by static magnetic field exposure. In contrast, wild type *Mycobacterium tuberculosis* was completely inhibited by blocking enzymatic iron reduction using static magnetic fields. *P. aeruginosa* is also well-known to use iron for their virulence, alginate production, mucoid phenotype change and biofilm formation. Though the exact mechanism is yet to be elucidated, the reduction of the biofilm biomass and the viability of *P. aeruginosa* in the current study may also be related to blockage of iron acquisition enzymes as shown previously in *E. coli* K-12 and M. tuberculosis.

In another study conducted on pathogenic microorganisms of the potato, exposure to oscillating magnetic fields for 250-350 seconds caused three fold reduction of *Ervinia carotovora* and *Streptomyces scabies* and less than two folds reduction in *Alternaria solani*. Thus, the authors suggested that oscillating magnetic fields can be used as a disinfection method for agricultural products and food. The current study also confirmed that the biofilms of the pathogen *P. aeruginosa* can be significantly disrupted by exposing to oscillating magnetic fields as well as combination of static and oscillating magnetic fields. However, it appears that the previously reported studies were not conducted in biofilm environments.

Though there are reports on various other pathogens, and the planktonic phases, there are no data pertaining to describe the potential mechanism by which magnetic fields control *P. aeruginosa* biofilms. According to the investigations of global gene expression conducted by Sandvik et al in 2013, extremely-low frequency magnetic fields up-regulated transposase activity, membrane transport processes, and signal transduction systems in a frequency-dependent manner, suggesting possible magnetic fields induced changes in ion transport in the bacterium.

MNPs Alone Do Not Affect the Viability of *P. aeruginosa*

The major advantage of using nanoparticles is that the target area can be precisely located and the release of the drug can be pre-planned, e.g., MNPs can be precisely controlled by a magnetic field and driven to the specific location of the body for desired action. MNPs have been successfully used in targeting cancer cells, imaging and drug delivery previously.

The antimicrobial properties of MNPs are likely dependent on nanoparticle type, dose and are pathogen dependent. For instance, iron oxide with silver nanoparticles demonstrated good antimicrobial properties against *E. coli, Staphylococcus epidermidis* and *Bacillus subtilis* and MRSA However, iron oxide alone have negligible toxicity/antibacterial activity on genetically engineered *P. aeruginosa* PTSOX4. Consistent with these previous reports, it is also reported here that MNP alone had no significant effects on the metabolism of *P. aeruginosa* biofilms. However, a significant reduction of the biomass of the biofilm was observed (FIGS. 4A-B). The differential effect of MNP on biofilm viability and biomass suggests that the dose of MNP needed to induce bacterial lysis may be higher than that needed for disruption of extra cellular matrix. In contrast, exposure of *P. aeruginosa* biofilms to SPIONs at concentrations up to 200 µg/ml resulted in an increase in biofilm biomass and a corresponding increase in cell density during 16 h period of incubation. Hence, the authors suggested reconsidering the usage of MNP in biofilm elimination. However, the MNP concentrations used in the present study was estimated to be several folds lower than 200 µg/ml. Nevertheless, as described in current literature, the usage of MNPs was mainly investigated in preventing biofilm formation rather than eliminating established biofilms. Thus, more studies are necessary to explore the properties of MNPs in eradication of existing biofilms.

Despite the negative findings noted with MNP alone treatment in the current study, the antimicrobial activity of nanoparticles in previous studies was suggested to be due their high surface-area-to-volume ratio which may be accompanied by the enhanced synthesis of reactive oxygen species (ROS) and free radicals. Thus, nanoparticles may interact with microbial membranes and kill them by damaging the microbial structure. The disruption of cell membrane and cytoplasmic leakage in response to chitosan nanoparticles has been previously observed in atomic force microscopy.

MNPs significantly disrupt *P. aeruginosa* biofilms in the presence of static switched magnetic fields.

Nanoparticles uptake by biofilms is usually low due to their poor diffusion and penetration properties into the biofilm Though SPIONs were also used throughout the present study, exposure of MNP treated *P. aeruginosa* biofilms to static magnetic fields did not yield any significant changes in biofilm metabolism but gave rise to a significantly increased biomass. Interestingly, under similar treatment conditions, exposure to static switched magnetic fields caused a significant reduction in biofilm metabolism and the biomass suggesting static switched magnetic fields may be more effective in directing MNPs to target site and in destroying established biofilms compared to static magnetic fields.

*Pseudomonas flourescens* exposed to iron oxide magnetic nanoparticles and an oscillating magnetic field of 873 kHz/100 Oe (Oersteds) resulted in a significant 3 log reduction (3 min exposure, 40° C.) of viable planktonic cells. Complete eradication of planktonic bacteria and a significant reduction of biofilm viability were achieved at 8 min exposure, at 55° C. However, complete eradication of biofilm was not seen even after 17 min exposure at 60° C. In contrast, when *P. aeruginosa* biofilms were treated with MNP and exposed to oscillating magnetic fields, no significant changes in biofilm viability was observed, however, biomass was significantly reduced. The difference in the resultant effect could be due to lower dose of MNP and/or magnetic field and/or temperature used. Nevertheless, the present finding once again suggests that the dose of MNP needed for bacterial cell lysis may be higher than that needed for matrix disruption.

Ciprofloxacin Significantly Eliminates *P. aeruginosa* Biofilms in the Presence of Static Switched Magnetic Fields.

In the present study, ciprofloxacin treated *P. aeruginosa* biofilms exposed to static one sided magnetic fields showed significant reduction in the biofilm viability. Most importantly it was the switched magnetic fields that exhibited the strongest significant inhibitory effects on biofilm metabolism and biomass despite oscillating magnetic field treatment regimens also exhibited lesser significant findings. It can be speculated that static switched magnetic fields disrupt biofilm matrix more efficiently than static one sided magnetic fields providing ciprofloxacin a better access to reach deeper layers of the biofilm. Thus, current study indicates that the exposure to static switched magnetic fields increases the efficiency of bacterial killing exerted by ciprofloxacin. Further investigations are necessary to explain the mechanism of bacterial killing and biofilm reduction mediated by ciprofloxacin in assistance with static switched magnetic fields.

Magnetic Nanoparticles Assist Ciprofloxacin in Biofilm

In the latter part of the study *P. aeruginosa* biofilms were treated with MNP, ciprofloxacin and exposed to magnetic fields. There are no reports in the literature with regards to simultaneous application of all three treatment modalities to bacterial biofilms. The present results show superior inhibitory effects of MNP and antibiotics on *P. aeruginosa* biofilms. SDL+MNP+Cipro treated *P. aeruginosa* biofilms without exposing to magnetic fields showed significantly lower metabolism and biomass compared to SDL treated control biofilms. However, when biofilms were treated with MNP and ciprofloxacin individually (SDL+MNP and SDL+Cipro), no significant results were observed (despite significant reduction in their biomass). This indicates that combined treatment of MNP and ciprofloxacin is more effective in eradication of *P. aeruginosa* biofilms than their individual effects.

Interestingly, when combined treatment of SDL+MNP+Cipro was exposed to magnetic fields, static switched magnetic field was the only magnetic exposure that could exert significant reduction of the biofilm metabolism compared to unexposed controls despite the significant reduction of biomass of all biofilms except the one exposed to static magnetic fields. Hence, when all different treatment situations considered, the best biofilm suppression was observed with static switched exposure.

Summary

In summary, mere exposure of biofilms to magnetic fields resulted in significant destruction and killing of *P. aeruginosa* biofilms. Thus, upon further optimization, combined therapy of antibiotics with MNPs and exposure to magnetic fields can be used as a promising novel therapeutic approach/treatment strategy for biofilm associated infections in soft tissues as well as in medical devices.

Our results also indicate that combination therapy of MNP and ciprofloxacin demonstrate superior properties in eliminating biofilms compared to their individual effects. In the spectrum of the dosage used, MNP itself did not elicit significant effects of bacterial killing, however, it reduced the biofilm mass. Exposure to magnetic fields did not show any added advantage when treated with MNP. Hence, longer exposure period with stronger magnetic fields may be required to trigger a significant effect.

Part II. Inhibition of Bacterial Growth by Iron Oxide Nanoparticles With and Without Attached Drug.

*Pseudomonas aeruginosa* is among the top three leading causative opportunistic human pathogens, possessing one of the largest bacterial genomes and an exceptionally large proportion of regulatory genes therein. It has been known for more than a decade that the size and complexity of the *P. aeruginosa* genome is responsible for the adaptability and resilience of the bacteria to include its ability to resist many disinfectants and antibiotics. The susceptibility of *P. aeruginosa* bacterial biofilms to iron oxide (magnetite) nanoparticles (NPs) with and without attached drug (tobramycin) have been investigated. The susceptibility of zero-valent iron NPs was also characterized, which are known to inactivate microbes. The particles, having an average diameter of 16 nm were capped with natural alginate, thus doubling the hydrodynamic size. Nanoparticle-drug conjugates were produced via cross-linking drug and alginate functional groups. Drug conjugates were investigated in the interest of determining dosage, during these dosage-curve experiments, NPs unbound to drug were tested in cultures as a negative control. Surprisingly, it was found that the iron oxide NPs inhibited bacterial growth, and thus, biofilm formation without the addition of antibiotic drug. The inhibitory dosages of iron oxide NPs were investigated and the minimum inhibitory concentrations are presented. These findings suggest that NP-drug conjugates may overcome the antibiotic drug resistance common in *P. aeruginosa* infections.

Unfortunately, in the case of CF patients, there is another complication to the treatment of biofilm infections resulting from this particular bacterial species. Since CF sputum is highly viscous, diffusion of oxygen is inhibited and hypoxic conditions exist. As previously mentioned, low oxygen or hypoxic environmental conditions promote biofilm formation by *P. aeruginosa*. The presence of this thick, sticky mucus characteristic of CF disease also complicates the infection by adding an additional barrier to drug diffusion. In this case, drug delivery must penetrate both the viscous mucus layer and the biofilm polymer matrix in order to reach the bacterial colonies below as illustrated in FIG. 8. Previous studies have shown that microparticles (560 nm) using free diffusion to deliver drug, are often entrapped in mucus, despite this, nanoparticles (120 nm) exceeded the rate of diffusion through mucus when compared to larger particles (560 nm). Since the maximum pore size in CF sputum is 400 nm, this enhancement in transport can be attributed to diffusion through the pores. Therefore, the ideal drug carrier should be significantly smaller than 400 nm if the goal is to enhance the rate of free diffusion of the particles through mucus pores.

According to another report, there are no clinically effective inhibitors of biofilm formation presently available. The inhibitors must be delivered through biofilm and mucus barriers. In order to address the drug delivery problem, iron oxide (magnetite) nanoparticles were capped with biodegradable short-chain carboxylic acid derivatives conjugated to the most common antibiotic arsenal for the treatment of gram negative bacteria; tobramycin. The functionalized nanoparticles may carry the drug past the mucus and biofilm layers to target the bacterial colonies via magnetic gradient-guided transport. Additionally, the magnetic ferrofluid may be used under application of an oscillating magnetic field to raise the local temperature, causing biofilm disruption, slowed growth, and mechanical disruption. *P. aeruginosa* can sustain growth at temperatures up to 42° C., therefore, an increase in the local temperature may increase the bacterial susceptibility to the antibiotic drugs if not completely destroying them. This engineered ferrofluid is a viable treatment option for multi-drug resistant strains, which appear to be increasing in many nosocomial as well as acquired opportunistic infections.

Our group has previously demonstrated that superparamagnetic iron oxide nanocrystals exhibit enhanced diffusion through alginate biofilms using magnetic field gradient guiding in vitro, see, S. L. McGill, C. L. Cuylear, N. L. Adolphi, M. Osinski, and H. D. Smyth, "Magnetically responsive nanoparticles for drug delivery applications using low magnetic field strengths," *NanoBioscience, IEEE Transactions on*, vol. 8, pp. 33-42, (2009). In addition to the benefit of magnetic field guided transport, magnetic nanoparticles are capable of releasing heat upon placement in an external oscillating magnetic field, see, S. L. McGill, C. Cuylear, N. L. Adolphi, M. Osinski, and H. Smyth, "Enhanced drug transport through alginate biofilms using magnetic nanoparticles," in SPIE BiOS: *Biomedical Optics*, pp. 718918-718918-8, (2009), although more work is needed to tune this property in vivo. Three mechanisms are implicated in NP heating in the frequency range suitable for human patient treatment: Neel relaxation, Brownian motion, and/or hysteresis losses (in the ferromagnetic size range). This phenomenon is exploited in the application of hyperthermic tumor destruction, or thermotherapy. Heat released from magnetic nanoparticle hyperthermia may further enhance the magnetic field guided particle movement through the mucus and EPS matrix in the lower respiratory tract by reducing their viscosity. In addition, thermal energy could be used to trigger drug release, if necessary, from the nanoparticles once the magnetic nanoparticles have reached the area of interest.

The synthesis and characterization of iron oxide and zero-valent iron NPs capped with either polyethylene glycol or alginate compared to tobramycin conjugated iron oxide NPs in the inhibition of bacterial growth and biofilm formation is presently reported. The polymer cap is engineered to enhance solubility of nanoparticless in water and reduce their oxidation, aggregation, and allow for further functionalization when desired. Spherical magnetic NPs having a mean radius of 16 nm were synthesized and characterized by transmission electron microscopy (TEM), X-ray diffraction (XRD), and energy dispersive X-ray spectroscopy (EDS), and tested for magnetic hyperthermia using the NanoTherics, Ltd. Magnetherm. NPs were further functionalized and conjugated to tobramycin using EDC/sulfo-NHS cross-linking. The drug loaded NPs, as well as NP samples alone, and drug alone (tobramycin) were used to test the sensitivities of established mucoidal colonies of *P. aeruginosa* after 48 hours of growth. Tobramycin antibiotic was chosen for these studies because it has been shown to be the most active drug tested on clinical isolates of *P. aeruginosa* and exhibited excellent activity against multidrug resistant (MDR) strains [Shawar 1999].

Figure 9:
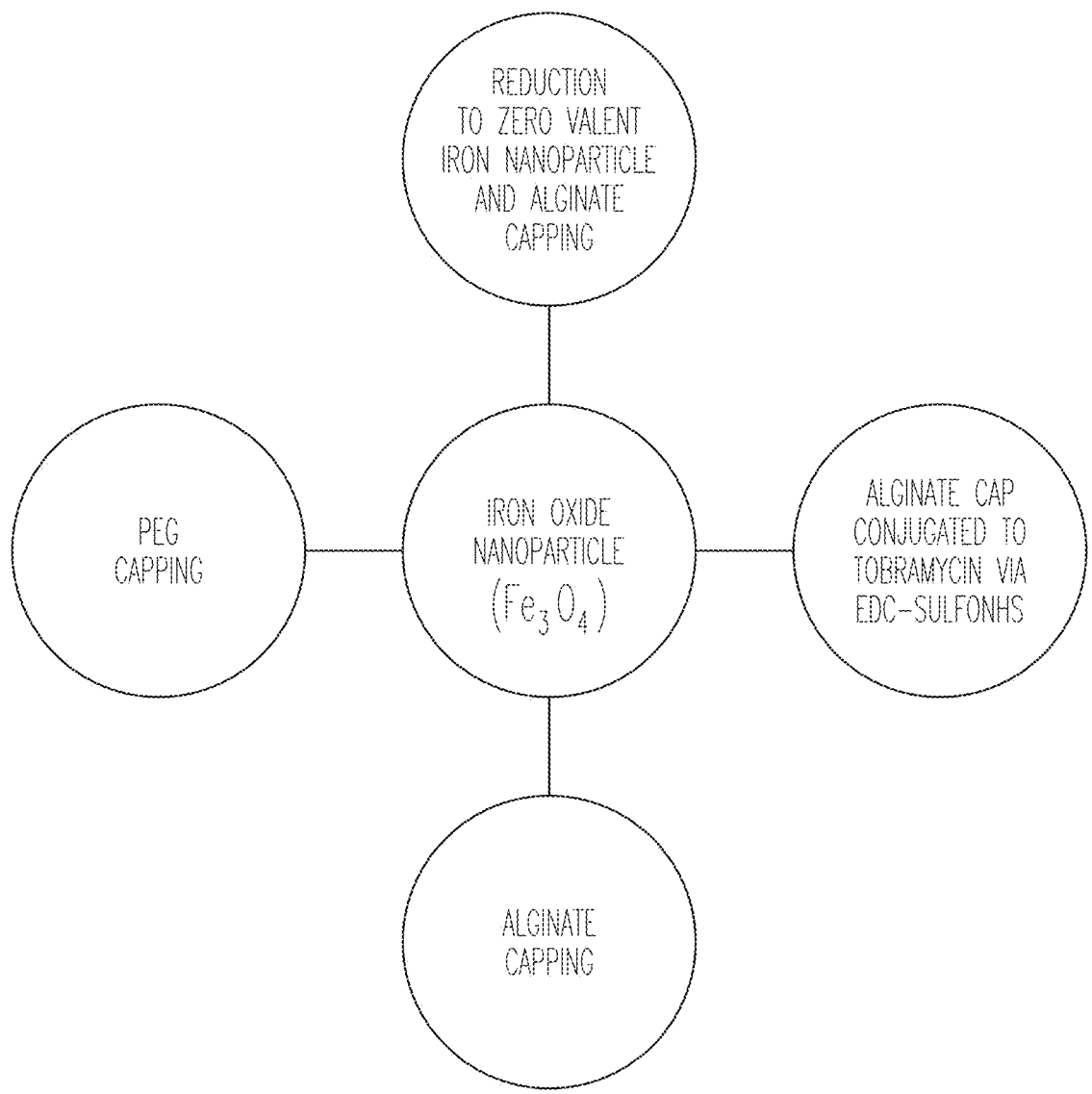
FIG. 9 illustrates different modifications made to the starting material (magnetite NPs) before sensitivity testing, in accordance with various embodiments, in accordance with various embodiments.

Four different batches of NPs were produced for sensitivity testing; magnetite capped with alginate, magnetite capped with polyethylene glycol (PEG), zero-valent iron NPs capped with alginate, and NPs capped with alginate and conjugated to tobramycin. FIG. 9 shows the pathways leading to functionalization of each batch. Iron oxide was investigated in the uncapped form as well as with a biodegradable (alginate) and a non-biodegradable polymer (PEG). A more thorough negative control would include a non-drug conjugated sample having the same polymer cap used for drug conjugation.

Example 2.1

Synthesis of Magnetic NPs and NP-Drug Conjugates

Magnetite ($Fe_3O_4$) NPs were synthesized in high boiling point inert organic solvent, using a solvothermal method for high crystallinity. The procedure is a green-chemistry modification of a procedure published in J. Park, K. Ahn, Y. Hwang, J.-G. Park, J.-H. Noh, J.-Y. Kim, et al., "Ultra large scale synthesis of monodisperse nanocrystals," Nature Materials, vol. 3, pp. 891-895, (2004). The organic carrier molecule, iron oleate, was produced in-house using a modified procedure published in L. M. Bronstein, X. Huang, J. Retrum, A. Schmucker, M. Pink, B. D. Stein, et al., "Influence of iron oleate complex structure on iron oxide nanoparticle formation," Chemistry of materials, vol. 19, pp. 3624-3632, (2007).

In this method, the time separation between nucleation and growth can be maximized to achieve monodispersity as well as morphology control. Zero-valent iron NPs were produced by reducing the iron oxide NPs with sodium borohydride under argon flow.

Materials. $FeCl_3 \cdot 6H_2O$ (97%), and alginic acid sodium salt were purchased from Sigma-Aldrich, n-docosane (99%) and n-eicosane (99%) were purchased from Alfa Aesar, sodium oleate (>97%) was purchased from Tokyo Chemical Industry Co., polyethylene glycol 5000 powder was purchased from Fisher Chemical. All chemicals were used as received without purification.

Synthesis of iron oleate; precursor complex. In a 1000 mL three-neck flask with a condenser, using standard air-free conditions, 25.92 g iron(III) chloride hexahydrate ($FeCl_3 \cdot 6H_2O$) and 87.60 g sodium oleate were solvated by 96 mL deionized (DI) water, 192 mL ethanol, and 336 ml, hexane (to dissolve the organics). Under argon flow, the flask was heated to 70° C. while stirring at 3000 rpm. The flask was kept refluxing at this temperature for 4 hours. Then, the product was washed 3 times with 96 mL DI water (in 32 mL aliquots) using a separatory funnel. The mixture was then placed in the rotary evaporator (RotoVap) to evaporate away any remaining hexane. The flask was then vacuum sealed, and placed in the oven for 24 hours at 70° C. The final product was a dark brown solid.

Synthesis of iron oxide (magnetite) NPs. In a 500 mL three-neck flask with a condenser, 16.20 g of the iron oleate complex produced above was combined with 2.57 g of oleic acid. 30 mL of paraffin wax was added to the flask, along with 5-10 boiling stones, since a characteristic nucleation event occurs at 200° C. and may cause the pressure to increase significantly. Under argon flow, the mixture was heated to 370° C. at a rate of 5° C. per minute and held at temperature for 15 minutes.

Synthesis of zero valent iron NPs. In the same 500 mL three-neck flask, the iron oxide NPs were dissolved in docosane and reduced with a molar equivalent of $NaBH_4$. The reaction was carried out at 250° C. and kept at temperature for 2 hours. After which, the NPs were washed using air free conditions, and capped with alginate.

Removal of oleic acid cap. The NPs come out of synthesis with oleic acid coating them. The oleic acid cap is removed using a hydrochloride solution wash at a pH of 1. Since the carboxyl group of the oleic acid becomes protonated around a pH of 5; the pKa of the carboxyl group is ~5.4. Once protonated, the carboxylic acid detaches from the delta negative nanoparticle surface. Oleic acid is soluble in methanol, so a standard methanol/hexanes extraction removes the oleic acid from the bare iron oxide nanoparticles.

Alginate capping. The NPs come out of synthesis capped in the metal carrier molecule (oleic acid) via a carboxyl group bound to the delta negative metal. The cap is removed with hydrochloric acid wash. Since the pKa of the terminal carboxyl group of oleic acid is around 5.5, any concentration of HCl that results in a pH<5.5 is sufficient to protonate the terminal carboxyl group. An HCl solution having a pH of 1 was used in order to ensure protonation and thus, detachment from the metal NP. The NPs were separated in a hexane/methanol mixture in which the methanol solvated the oleic acid. Once uncapped, sodium alginate was added to the NP in a 3 to 1 alginate to NP ratio (by mass) in chloroform solvent. The mixture was sonicated at 40 Hz for 4 hours to ensure complete coverage. The alginate-capped NPs were washed three times in chloroform using centrifugation, and dried in air.

Polyethylene glycol capping. Instead of alginate, a batch of magnetite NPs were capped with a non-biodegradeable polymer, succinylated polyethylene glycol (PEG). Succinylated PEG was synthesized in house from PEG-OH 5000, see, e.g., G. T. Hermanson, *Bioconjugate techniques*: Academic press, (1996).

Conjugation to Tobramycin. EDC crosslinking was done following a procedure from G. T. Hermanson, *Bioconjugate techniques*: Academic press, (2008). The procedure was slightly modified in that 5 mM of Sulfo-NHS was added to the reaction vessel to increase loading efficiency.

Structural Characterization. For structural characterization, samples for transmission electron microscopy (TEM) were prepared by placing a drop of the colloidal solution onto a 200-mesh carbon-coated copper grid. The solvent was allowed to evaporate away, thus fixing the sample on the grid.

Figure 10:
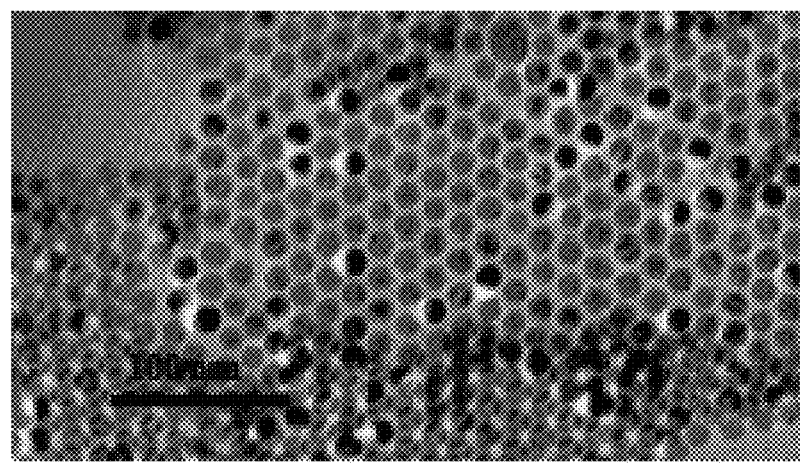
FIG. 10 illustrates a TEM image of magnetite NPs, in accordance with various embodiments.
Figure 11:
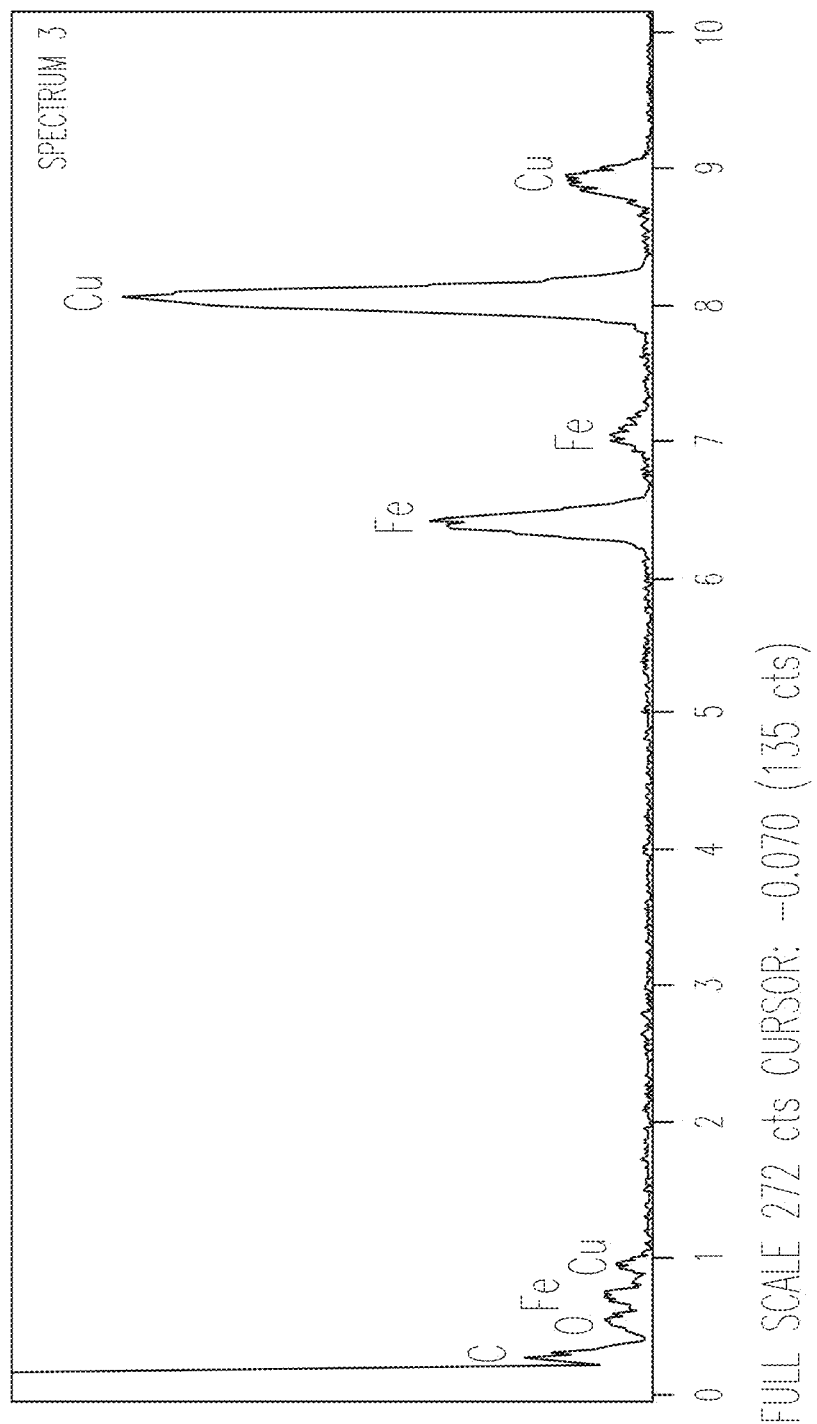
FIG. 11 illustrates an EDS spectrum of iron oxide nanocrystals, in accordance with various embodiments.

FIG. 10 illustrates an image of magnetite NPs taken by a JEOL-2010F high-resolution transmission electron microscope (HRTEM). The scale bar is 100 nm. The JEOL-2010F HRTEM was equipped with an OXFORD Link ISIS/Inca energy dispersive spectroscopy (EDS) apparatus, used to determine the elemental composition of the sample. The electron beam was focused on a single nanoparticle and the characteristic x-ray peaks specific to each element were identified using the OXFORD Link ISIS software. As shown in FIG. 11, the EDS spectrum confirms the presence of iron and oxygen. The copper lines are from the carbon-coated copper grid.

The XRD data for the iron oxide MNPs suggests the composition of the MNPs to be 70% $Fe_3O_4$ (magnetite) with space group {F41/d 3 2/}. There are peaks distinctive of $\alpha\text{-}Fe_2O_3$, which are likely the result of surface oxidation during the analysis. The remaining portions of the crystal appear to be composed of $Fe_2O_3$ and surprisingly the Wüstite (FeO) polymorph which commonly composes meteorites produced under low oxygen conditions. Because the phases have similar space groups and a values, the oxidation state is difficult to determine with absolute certainty.

Magnetic Characterization. A typical feature in magnetic nanoparticles is their irreversible ferromagnetic behavior below the blocking temperature $T_B$ and reversible magnetization above it caused by superparamagnetic behavior of the nanoparticles. The blocking temperature can be found experimentally by measuring magnetization under field-cooling (FC) and zero-field cooling (ZFC) conditions. Below $T_B$, the Neel relaxation time TN is larger than the measurement time (typically 100 s), and magnetization depends strongly on the field history. Above $T_B$, magnetization is strongly affected by thermal fluctuations ($\tau_m > \tau_N$), making FC and ZFC curves coincide. In other words, for a given measurement time $\tau_m$, hysteretic behavior observed below $T_B$ would not be observed above $T_B$.

We measured temperature dependence of magnetization for the $Fe_3O_4$ nanoparticle samples under ZFC and FC conditions. The dc ($\tau_m = 100$ s) magnetization of the ferrofluid samples was measured with a dc field of 100 Oe in the temperature range between 9 K and 350 K using a Quantum Design magnetic property measurement system (MPMS) superconducting quantum interference device (SQUID) magnetometer.

Example 2.2

Bacterial Biofilm Investigations

Establishment of biofilm communities. Biofilm communities were grown in sterile boiling stones in liquid media for 60 days until firmly established. Established colonies produced a thick polymer matrix and green proteins characteristic of *P. aeruginosa*. The long term growth should more accurately represent a chronic infection.

Materials. Luria-Bertani (LB) liquid growth media and LB agar were purchased from IPM scientific.

Method. Liquid cultures were grown in LB broth at 37° C. for 60 days. Biofilm cultures were grown in the LB broth on sterile boiling stones. Periodically, the liquid media was decanted, thus, leaving only attached cells in the culture. The cells were then replenished with fresh broth. This method is a low cost alternative to a flow chamber. After the 60 day period, the cultures were sonicated for the removal of attached cells, and diluted to an optical density at a 600 nm wavelength ($O.D._{600}$) between 0.5 and 0.6. $OD_{600}$ was determined using Cary 5000 UV-VIS-IR spectrophotometer against a "blank" cuvette; which contained only un-inoculated broth. Once diluted, the cultures were tested in liquid media or applied to agar plates for susceptibility testing.

Disk diffusion method. The disk diffusion method is one of the most popular approaches to bacterial sensitivity testing due to its low cost and efficiency. The disk, impregnated with a candidate antibiotic drug or compound of interest, is placed on the inoculated agar; which contains a uniform layer of bacteria taken from liquid culture. The disks are commercially available, containing the proper concentrations of antibiotic drugs based on moles per gram. As a low-cost alternative, disks may be prepared using filter paper soaked in the appropriate aqueous concentrations of the antibiotic drugs of interest. The underside of the plate is numbered for each sample to be tested. The cultures are distributed evenly onto a sterile agar plate using a sterile cotton swab to form a uniform layer on the agar. The disks, impregnated with NPs, drug, or NP-drug conjugates are then placed on top of the agar. The cultures are allowed to grow in the previous conditions overnight (16-18 hours).

Determination of minimum inhibitory concentration of tobramycin. For the measurement of the minimum inhibitory concentration (MIC), tobramycin sulfate was diluted to 1 mg/mL (stock solution) with sterile DI $H_2O$. Afterwards, tobramycin was serially diluted into 1 mL of DI $H_2O$ and added to the 1 mL aliquots of overnight bacterial culture to the final concentrations of tobramycin ranging from 25 to 250 µg/mL, with 25 µg/mL increments. For the control, 1 mL of sterile DI $H_2O$ was added to the aliquot of the culture. The cultures were then grown overnight on a rotary shaker at 37° C. and 150 rpm. The next day, 50 µL aliquots of the overnight cultures were diluted 1:2 with TSB, plated on the TS nutrient agar plates, and grown for 24 hours at 37° C. The next-day plates were checked for the presence of bacterial colonies. The MIC was narrowed down by using the dilution series with 5 µg/mL increments of tobramycin concentration, ranging between its highest concentration that still allowed the growth of *P. aeruginosa* colonies on the plate and the next lowest concentration that completely inhibited their growth.

Figure 12:
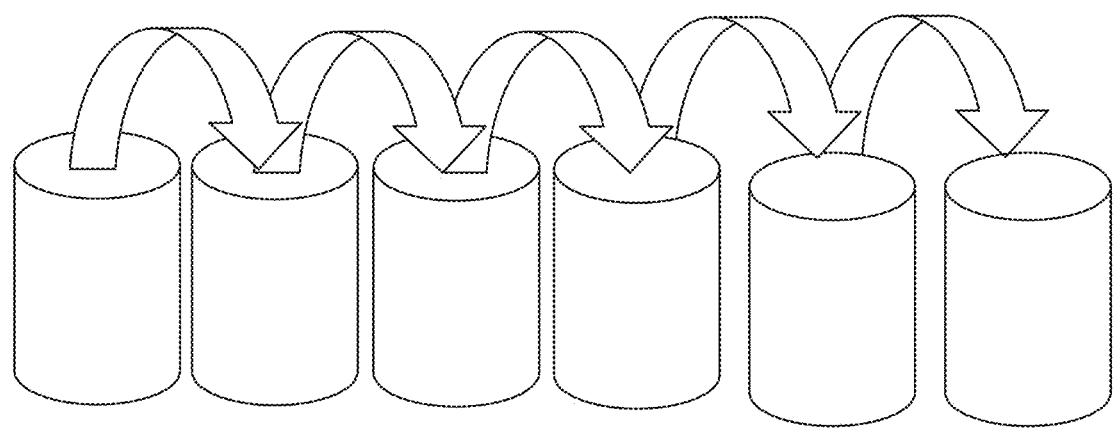
FIG. 12 illustrates a serial dilution procedure, in accordance with various embodiments.

Determination of minimum inhibitory treatment concentration. The diluted samples were treated with various concentrations (µg/mL); achieved by serial dilution starting at 17.35 mg/mL and serially diluted by taking 0.5 mL from the stock tube and moving it to the next tube and so on as shown below (12 times). Serial dilutions of tobramycin, NP bound to tobramycin, or NPs alone were investigated. FIG. 12 illustrates the serial dilution procedure.

Example 2.3

Results

Determination of minimum inhibitory concentration of tobramycin.

Using the procedure described in Section 3.2 and the dilution series of tobramycin, determined the MIC of this particular strain of *P. aeruginosa* was determined to be 15 µg/mL for planktonic cells and 50 µg/mL for biofilm cells. These findings introduce a starting point for inhibition of established biofilms. This is the MIC for tobramycin alone, without attachment to NPs. As discussed below, the MIC of tobramycin may vary significantly between different strains and planktonic vs biofilm cells.

Effectiveness of Tobramycin Conjugated NPs.

Table 3 illustrates results of agar sensitivity studies at 25, 50, and 100 mg/mL concentrations. Sensitivity is described with S for sensitive, I for intermediate, and R for resistant.

TABLE 1

Results of agar sensitivity studies.

| Chemical Applied | Concentration (mg/mL) | Zone of Inhibition (mm) | Sensitivity |
|---|---|---|---|
| Magnetite NP (uncapped) | 100 | 22 | S |
| Magnetite NP (uncapped) | 50 | 17.5 | S |
| Magnetite NP (uncapped) | 25 | 11 | I |
| Magnetite NP PEG-COOH 5 kDa cap | 100 | 0 | R |

TABLE 1-continued

Results of agar sensitivity studies.

| Chemical Applied | Concentration (mg/mL) | Zone of Inhibition (mm) | Sensitivity |
|---|---|---|---|
| Magnetite NP PEG-COOH 5 kDa cap | 50 | 0 | R |
| Magnetite NP PEG-COOH 5 kDa cap | 25 | 0 | R |
| Magnetite NP alginate cap | 100 | 22 | S |
| Magnetite NP alginate cap | 50 | 16 | I |
| Magnetite NP alginate cap | 25 | 10 | I |
| Magnetite NP alginate cap + tobramycin | 100 | 23 | S |
| Magnetite NP alginate cap + tobramycin | 50 | 11 | I |
| Magnetite NP alginate cap + tobramycin | 25 | 7 | R |
| Zero-valent iron NP alginate cap | 100 | 25 | S |
| Zero-valent iron NP alginate cap | 50 | 21 | S |
| Zero-valent iron NP alginate cap | 25 | 20 | S |
| Deionized water | 100% | 0 | R |

For the iron oxide NP's alone, it was found that inhibition of established biofilms on agar plates was observed for concentrations as below 25 mg/mL when the NPs are uncapped. When capped with alginate, the inhibition was also observed at 25 mg/mL despite the fact that part of the mass of this core-shell type NP consists of non-bioactive alginate. In the case of iron oxide capped with PEG, no inhibition was observed because of the non-biodegradeable nature of the capping agent. The iron was not available to the colonies, and therefore, did not inhibit bacterial growth. These findings suggest that a complete PEG cap may allow for the use of more toxic materials in vivo since the metal had no interaction with the cells. Even at high concentrations, some inhibition due to incomplete coverage seemed likely; however, that is not the case. In the case of iron oxide NPs conjugated to tobramycin, the bacterial inhibition at these concentrations was found mirrors the inhibition trend of iron oxide NPs alone.

TABLE 4

Biofilm-inhibition results. The nanoparticles were capped with alginate at 50 mg/mL after magnetic treatment at 24 hours. Tobramycin concentration was 2 mg/mL.

| Disk Number | Mucin Barrier | Alginate barrier | Both |
|---|---|---|---|
| 1. Fe$_3$O$_4$ | 30/S | 0/R | 20/S |
| 2. Zero-valent iron | 5/R | 20/S | 20/S |
| 3. Fe$_{16}$N$_2$ | 30/S | 32/S | 15/I |
| 4. Fe$_3$O$_4$-Tobra | 25/S | 19/S | 14/I |
| 5. Tobramycin | 32/S | 30/S | 20/S |

TABLE 5

Biofilm-inhibition results. The nanoparticles were capped with alginate at 50 mg/mL with no magnetic treatment. Tobramycin concentration was 2 mg/mL.

| Disk Number | Mucin barrier | Alginate barrier | Both |
|---|---|---|---|
| 1. Fe$_3$O$_4$ | 14/I | 0/R | 22/S |
| 2. Zero-valent iron | 0/R | 0/R | 14/I |
| 3. Fe$_{16}$N$_2$ | 0/R | 0/R | 0/R |

TABLE 5-continued

Biofilm-inhibition results. The nanoparticles were capped with alginate at 50 mg/mL with no magnetic treatment. Tobramycin concentration was 2 mg/mL.

| Disk Number | Mucin barrier | Alginate barrier | Both |
|---|---|---|---|
| 4. Fe$_3$O$_4$-Tobra | 0/R | 0/R | 0/R |
| 5. Tobramycin | 30/S | 40/S | 40/S |

For these experiments, an vitro biofilm model was that would mimic the infection in CF in which there is an alginate and mucin barrier to drug diffusion.

The antibiotic had no trouble penetrating. As you can see, the NPs had trouble and the activity was increased 2 to 3-fold when a magnet was applied.

Comparison of Biofilm Inhibition in Liquid Cultures.

Figure 13:
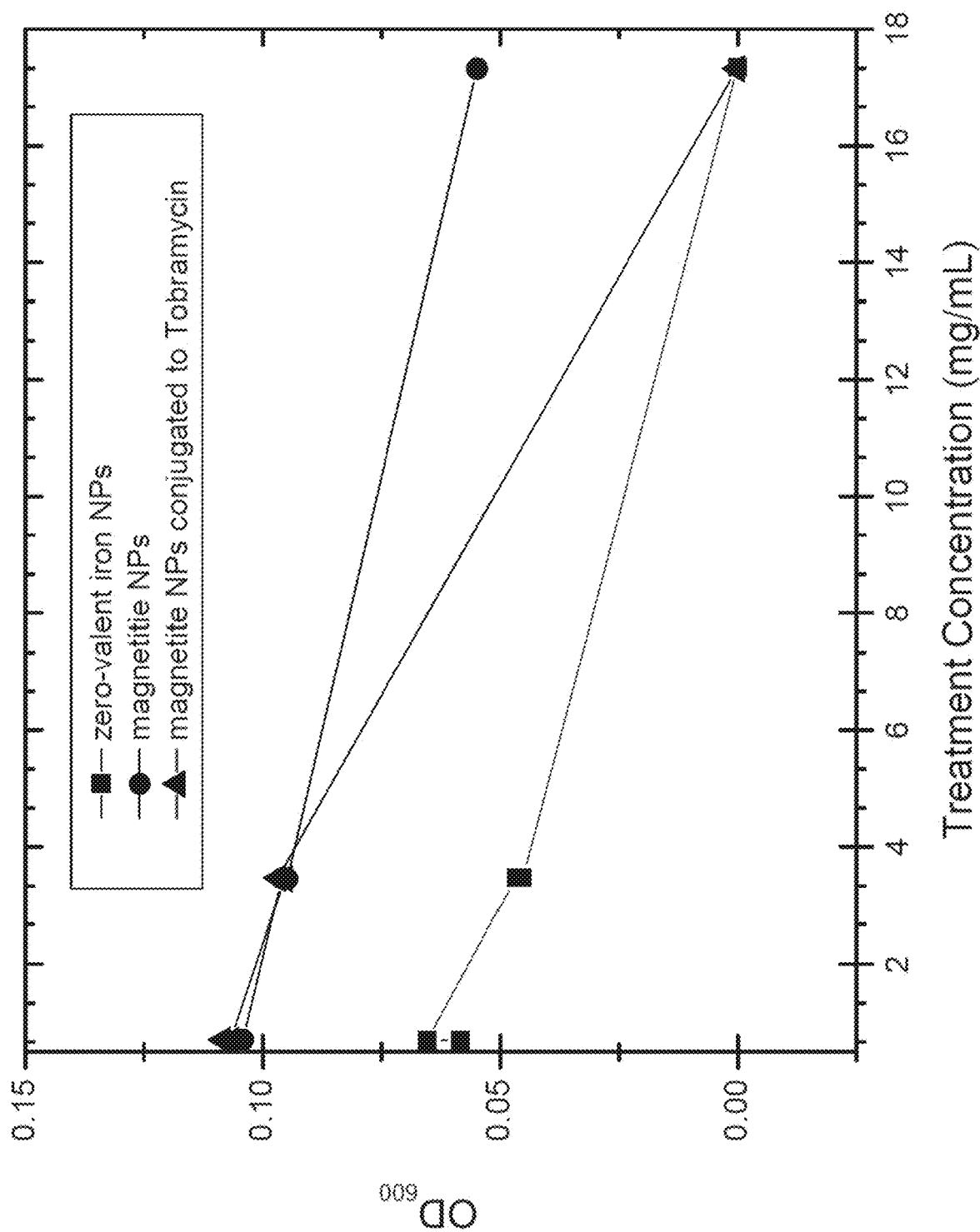
FIG. 13 illustrates optical density versus treatment concentration for various materials, in accordance with various embodiments.

Optical density was used to measure the number of cells in each liquid culture. Because such a large range of concentrations were tested (17 mg/mL to $8 \times 10^{-6}$ mg/mL) it was necessary to split the data into two graphs; high concentration in FIG. 13 and low concentration in FIG. 14. FIG. 13 shows higher dosages, at this range the NP-drug conjugates had the greatest slope. The inhibition by zero-valent iron was, not surprisingly, higher than iron oxide and NP-drug conjugates. This can be attributed to the high reactivity of zero-valent iron; its uncanny ability to increase reactive oxygen species (ROS) in the local region.

Figure 14:
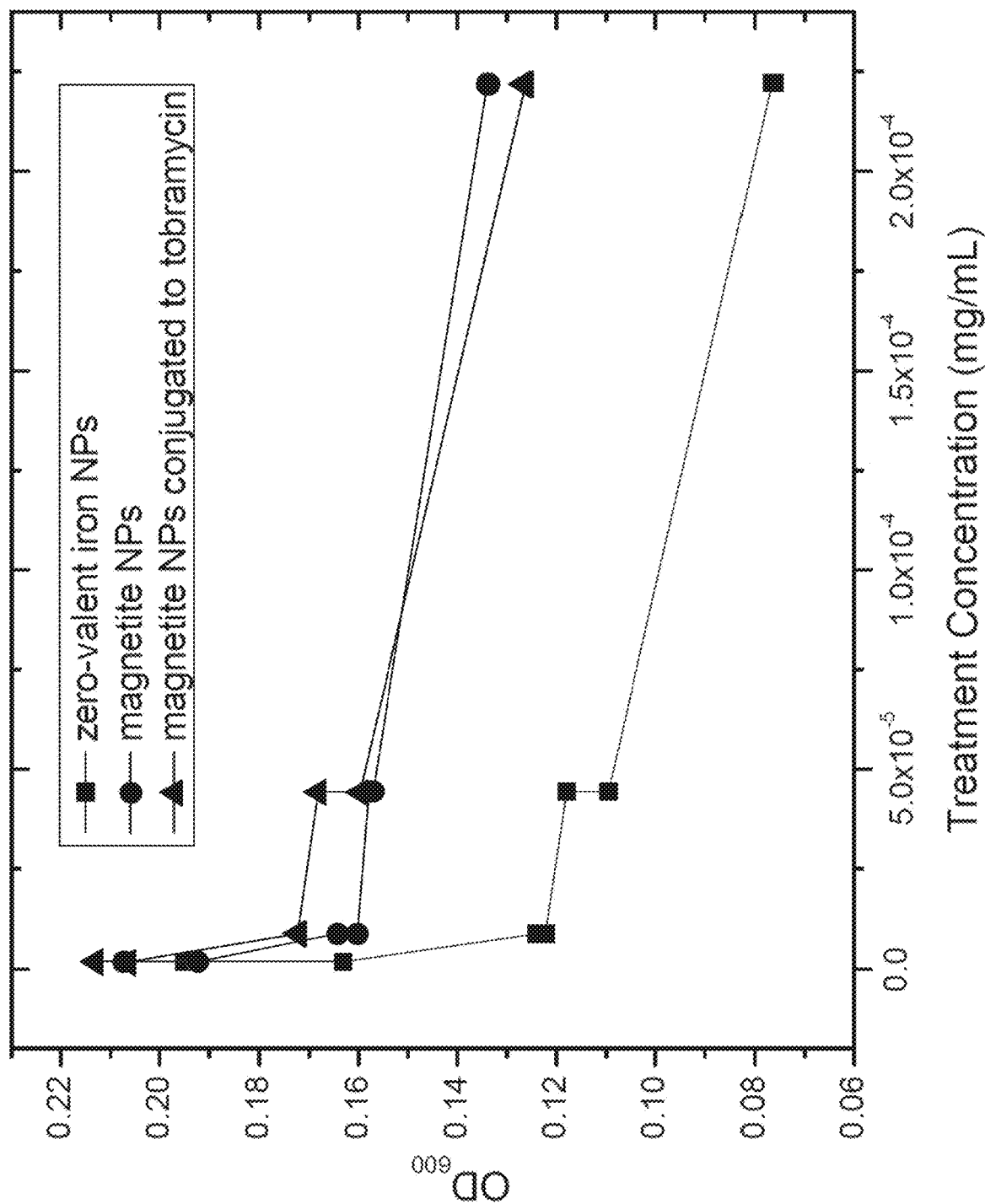
FIG. 14 illustrates optical density versus treatment concentration for various materials, in accordance with various embodiments.

FIG. 13 illustrates optical density (OD) at a 600 nm wavelength for liquid cultures exposed to treatment: iron oxide NPs, zero-valent iron, or tobramycin conjugated iron oxide. All materials were alginate capped. Increasing OD signifies more bacterial colonies. This graph shows high concentrations. FIG. 14 illustrates $OD_{600}$ for treatments at low concentrations. The iron oxide, zero valent iron, and tobramycin conjugates inhibited growth at exceptionally low ($8 \times 10^{-6}$ mg/mL or 0.008 μg) concentrations. These figures demonstrate the inhibition of bacterial cells even at surprisingly low (0.008 μg/mL) concentrations, although the minimum therapeutic dose would probably be closer to 0.005 μg/mL where significant inhibition was observed. Higher doses would likely be necessary to treat established infections involving biofilms. This data speaks to the feasibility of these materials as low cost treatment options.

Example 2.4

Discussion

Figure 15:
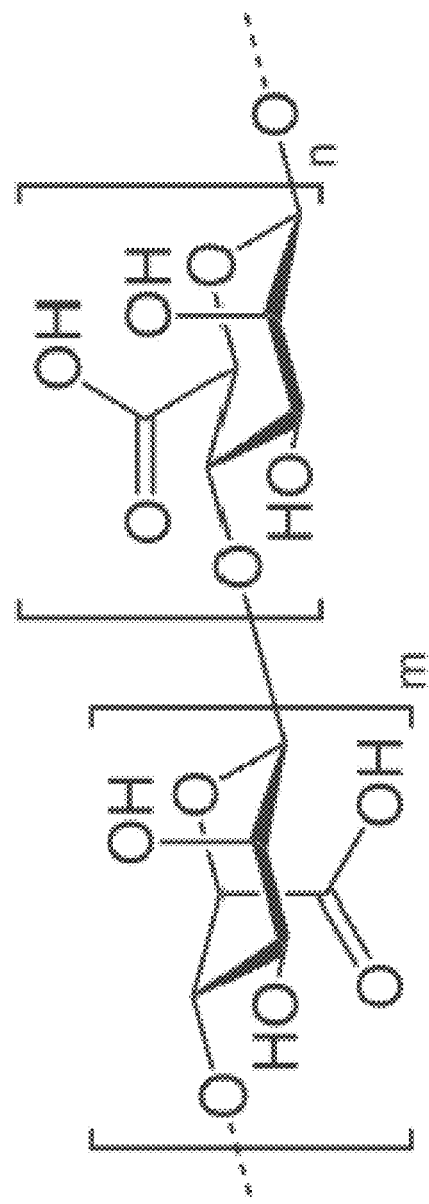
FIG. 15 illustrates an alginate monomer, in accordance with various embodiments.

It appears that the iron oxide NPs inhibited growth as well as the drug-conjugated iron oxide. A conjugation procedure was done involving the bonding of functional groups. The capping agent, alginate, has a total of 12 functional groups on each monomeric unit including three hydroxyl groups and one carboxyl group providing several options for attachment to a primary amine. An alginate monomer is illustrated in FIG. 15.

Figure 16:
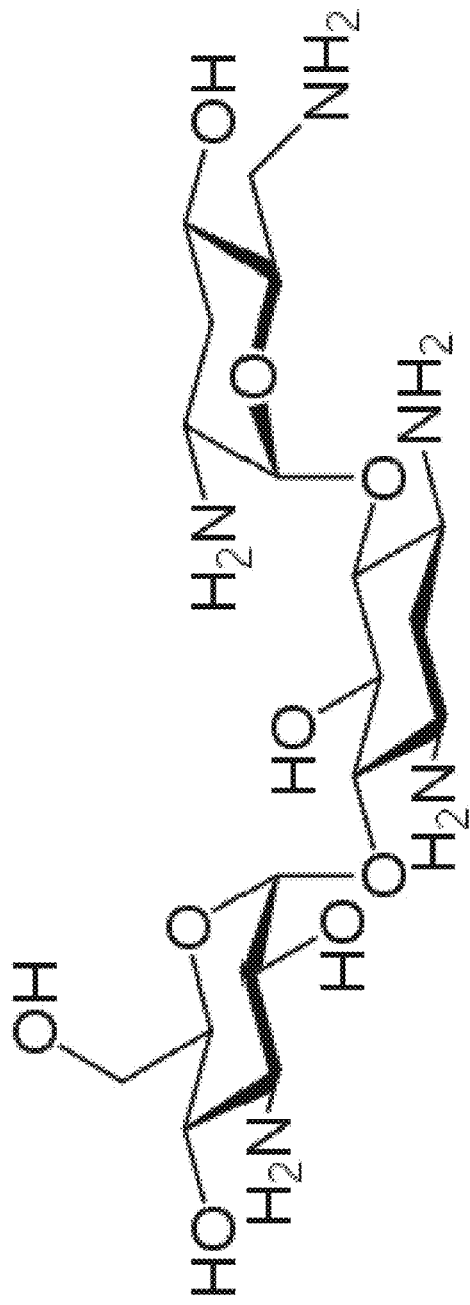
FIG. 16 illustrates a tobramycin molecule, in accordance with various embodiments.

The tobramycin molecule, illustrated in FIG. 16, has a total of 14 functional groups per molecule consisting of five primary amines, five hydroxyl groups, and four electronegative ethers in the hydrocarbon. If one takes these numbers alone accounting only for the activity of carboxyl groups with amines, there are ten different possibilities for conjugation conformations.

These molecules do not necessarily attach drug in a patterned linear fashion, but by crosslinking polymer to polymer or making drug-polymer, "tangles," thus increasing the mass of the non-bioactive ingredients. Further characterization is necessary to calculate the % by mass of iron oxide, tobramycin, and inert material. This would allow us to measure the dosage of the active material only.

It is apparent from the present findings that the iron oxide did inhibit bacterial growth via an unknown mechanism. Zero-valent iron, as predicted, had a dramatic antibacterial effect. Although zero-valent iron is too reactive for in vivo use at present, it may be a candidate for incorporation into antibacterial coatings. Similarly, iron oxide NPs having high biocompatibility, may be a candidate material for incorporation into antibacterial coatings on medical devices such as stents, catheters, and surgical sutures as a low cost alternative to silver NPs.

Numerous potential applications exist for these materials in addition to treating biofilm colonies in the respiratory tract of CF patients. The combination of tobramycin or other drugs with iron oxide NPs incorporated into biodegradeable polymers may hold promise for the long-term control of multidrug resistant bacterial strains, analogous to the way triple therapy controls retroviral infections. Specifically, tobramycin seemed to exhibit the greatest activity against MDR strains of *P. aeruginosa*, the combination of drug with the antibacterial properties of iron-containing nanomaterials as well as the option to use their magnetic properties for gradient-guided delivery, just might conquer the antibiotic resistance problem.

Part III. Inhibition of Bacterial Growth by Iron Oxide Nanoparticles With and Without Attached Drug.

Example 3.1

Multi-functional superparamagnetic iron oxide nanoparticles (SPIONs) can facilitate increased drug transport rates across extracellular barriers in lung diseases. SPIONs can utilize static magnetic force for penetration of extracellular barriers. SPIONs can increase diffusive transport through microenvironment heating/mechanical disruption (hyperthermia). SPIONs can act as nanopullies (with conjugated drug) or nanoknives (opening the pathway for drug delivery).

Iron oxide Nanoparticle synthesis. The iron oxide nanoparticles were formed using a pure/dry iron oleate complex, which was stored in a vacuum sealed container in oven for 24 hours. The iron oleate to oleic acid mole ratio was 2:7. The nanoparticles were formed in docosane solvent (hp 368.6° C.), using a three-necked flask having a stopper in the right neck, a thermometer in the second neck and a reflux condenser in the third neck. The reflux time was 3 minutes. The NPs were allowed to cool and kept in solid solvent to prevent oxidation.

Zero-valent iron Nanoparticle synthesis. Iron oxide NPs were dissolved in docosane and reduced with a molar equivalent of $NaBH_4$. The reaction was carried out at 250° C. and kept at temperature for 2 hours. After which, the NPs were washed using air free conditions. NPs were redispersed in chloroform and capped with alginate Biofilm communities were grown in sterile boiling stones in liquid media for 60 days until firmly established. Established colonies produced a thick polymer matrix and green proteins characteristic of *P. aeruginosa*. The long term growth should more accurately represent a chronic infection.

Liquid cultures were grown in Luria-Bertani (LB) broth at 37° C. for 60 days. Biofilm cultures were grown in the LB broth on sterile boiling stones. Periodically, the liquid media was decanted, thus, leaving only attached cells in the culture. The cells were then replenished with fresh broth. This method is a low cost alternative to a flow chamber. After the 60 day period, the cultures were sonicated for the removal of attached cells, and diluted to an optical density at a 600 nm wavelength ($O.D._{600}$) between 0.5 and 0.6. $OD_{600}$ was determined using Cary 5000 UV-VIS-IR spectrophotometer against a "blank" cuvette; which contained only un-inoculated broth. Once diluted, the cultures were tested in liquid media or applied to agar plates for susceptibility testing.

Findings in Liquid cultures. It appears that the iron oxide NPs inhibited growth better than drug-conjugated iron oxide, however, conjugation which may have increased the mass of the non-active ingredients. Iron oxide did inhibit bacterial growth. Zero-valent iron had a dramatic antibacterial effect. Iron oxide alone, may be a candidate material for incorporation into antibacterial coatings on medical devices. The combination of tobramycin or other drugs with iron oxide NPs incorporated into biodegradable polymers may hold promise for the long term control of multidrug resistant bacterial strains.

Part IV. Effect of Magnetic Nanoparticles and Static Magnetic Fields on Mixed Species Oral Biofilms.

Microbial inocula. Unstimulated whole saliva was collected from a healthy adult male and stored at −80° C. until further use. Microbial growth media was prepared in Brain heart infusion media supplemented with 6% (V/V) sheep blood. Immediately prior to each experiment whole saliva from the stock was added to growth media to prepare mixed species oral microbial suspension (10% (V/V) saliva in the final suspension).

Biofilm Formation. Mixed species oral biofilms were formed using the following procedure. Commercially available pre-sterilized, polystyrene, flat bottom 6-well microtiter plates (BD Biosciences, Calif., USA) were used. At first, 3 mL of microbial suspension was transferred into the wells of a microtiter plate, and the plate was incubated for 24 h (37° C., 75 rpm) under aerobic growth conditions. At the end of the incubation, wells washed twice with PBS to eliminate traces of the medium and free floating microbial cells. The effects of various treatments were studied on such preformed biofilms in a period of 24 h.

Example 4.1

Determination of Concentration Dependent Effect of MNPs

Biofilm phase. Mixed species oral biofilms were developed in sterile 96 well plates (BD biosciences, USA) as described above. Biofilms were washed twice with PBS and magnetic nanoparticles (MNP) were administered in a concentration gradient (two fold). The plates were incubated for 24 h at 37° C.

At the end of incubation period, XTT reduction assay (2,3-Bis-(2-Methoxy-4-Nitro-5-Sulfophenyl)-2H-Tetrazolium-5-Carboxanilide) was performed to quantify the viability of biofilms. The assay was performed quadruplicates at two times.

Example 4.2

Biofilm Formation and Treatment

Mixed species oral biofilms were developed for 24 h in sterile 6 well plates as described above. Twenty-four-hour biofilms were washed twice with sterile PBS and the MNP suspended in PBS (200 μg/ml) was administered on to mixed species oral biofilms. Biofilms that unreated with MNP were used as the controls. Subsequently, the plates were exposed to one of 2 different magnetic field treatments. Static magnetic field treatments involved in exposing the 24 h-biofilm, with or without MNPs, to magnetic fields from the bottom of the 6-well plate for 6 h using molybdenum magnets (magnetic field strength at the biofilm=4.44 kG, using the configuration shown in FIG. 1A). Switched static magnetic field treatment involved exposing the 24 h-biofilm, with or without MNPs, to magnetic fields from the bottom of the 6 well plates for 30 min (magnetic field strength=4.44 kG) followed by exposing from the top of the 6-well plate for 30 min (magnetic field strength was 0.12 kG) for 6 h of total exposure using the configuration shown in FIG. 1B). After magnetic field treatment, biofilms were incubated in incubator for 24 h at 37° C. At the end of incubation period, the biofilms were washed twice with PBS; XTT reduction assay was performed to quantify the viability of biofilms by means of measuring metabolic activity.

Example 4.3

XTT Reduction Assay

At the end of incubation of both test and control biofilms, a standard XTT (sodium 2,3,-bis(2-methoxy-4-nitro-5-sulfophenyl)-5-[(phenylamino)-carbonyl]-2H-tetrazolium inner salt) reduction assay was performed thereafter to measure the viability of biofilms by means of bacterial cell metabolic activity. In brief, commercially available XTT powder (Sigma, Mo., USA) was dissolved in PBS to a final concentration of 1 mg/ml. Then the solution was filter-sterilized (0.22 µm pore size filter) and stored at −70° C. Freshly prepared 0.4 mM menadione solution was used for XTT reduction assay. XTT solution was thawed and mixed with menadione solution at 20:1 (v/v) immediately before the assay. Thereafter, PBS:XTT:Menadione in 79:20:1 proportion were added into each culture dish containing biofilms and incubated in the dark for 5 h at 37° C. The color changes were measured with a microtiter plate reader (Infinite M200 microplate reader, TECAN US Inc, N.C., USA) at 492 nm. All assays were carried out in triplicate on two different occasions.

Example 4.4

Confocal Laser Scanning Microscopy

Biofilms were prepared on Sterile cover slips placed in commercially available sterile flat bottom six well plates (Nunclon, Nunc, thermo Fisher scientific, USA) as described above. Pre-formed 24 h biofilms were exposed to magnetic fields with or without MNPs and incubated for another 24 h at 37° C. At the end of incubation, the prewashed coverslips were stained with Live and Dead stain (Live/Dead BacLight Bacterial Viability kit, Invitrogen, Eugene, USA). The biofilm was then analyzed by fluorescent microscopy (using confocal laser scanning microscope, Nikon C2 Inverted confocal microscope, Nikon, Japan).

Example 4.5

Statistical Analysis

Statistical analysis was performed using SPSS software (version 16.0). Mann Whitney U-test was performed to compare the significant differences between corresponding control and test sample of the mixed species oral biofilms and to compare the significant differences between test samples of the Mixed species oral biofilms under different treatment conditions. A P-value of less than 0.05 was considered statistically significant.

Example 4.2

The Effects of Magnetic Fields on Mixed Species Oral Biofilms Treated with Control Particles Biofilm metabolism (XTT reduction assay). When the biofilms were treated with various magnetic fields as mentioned above, all test samples exposed to magnetic fields exhibited significant reduction in the metabolic activity compared to untreated (i.e. magnetic field free) biofilm controls (p<0.05, FIG. 17A, Table 1). Comparing the different magnetic field treatments to each other, no significant differences in the mean XTT readings were found.

Figure 17A:
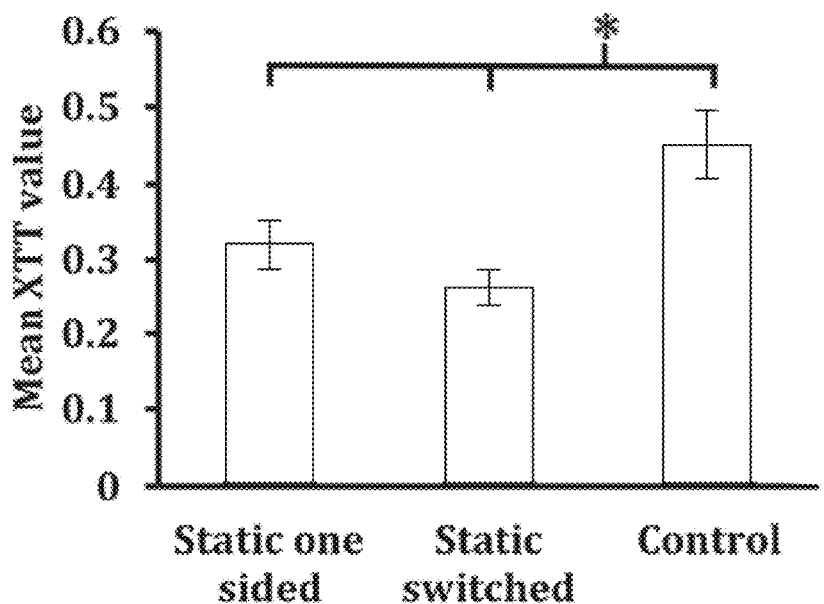
FIG. 17A illustrates mean XTT values for mixed species biofilm exposed to various magnetic fields along with a control sample exposed to no magnetic fields, in accordance with various embodiments.
Figure 17B:
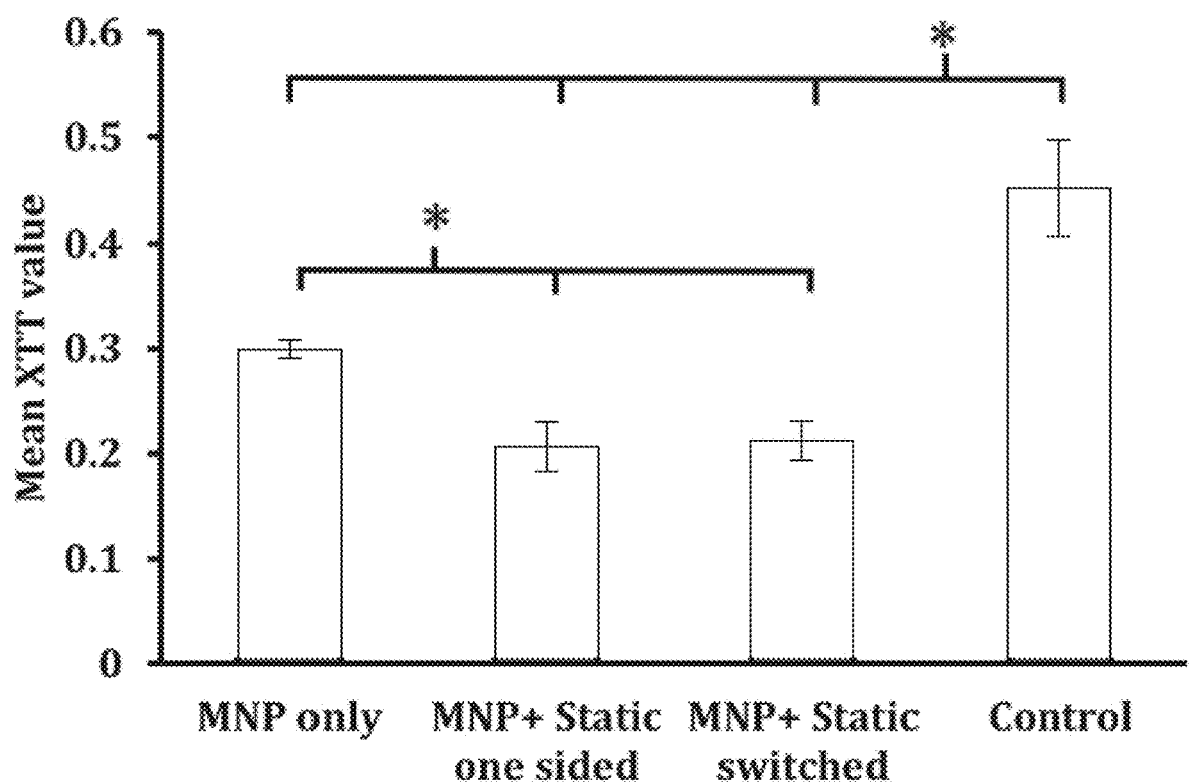
FIG. 17B illustrates mean XTT values for mixed species biofilm treated with MNPs and exposed to various magnetic fields along with a control sample that had no MNP treatment and no magnetic field exposure, in accordance with various embodiments.
Figure 17C:
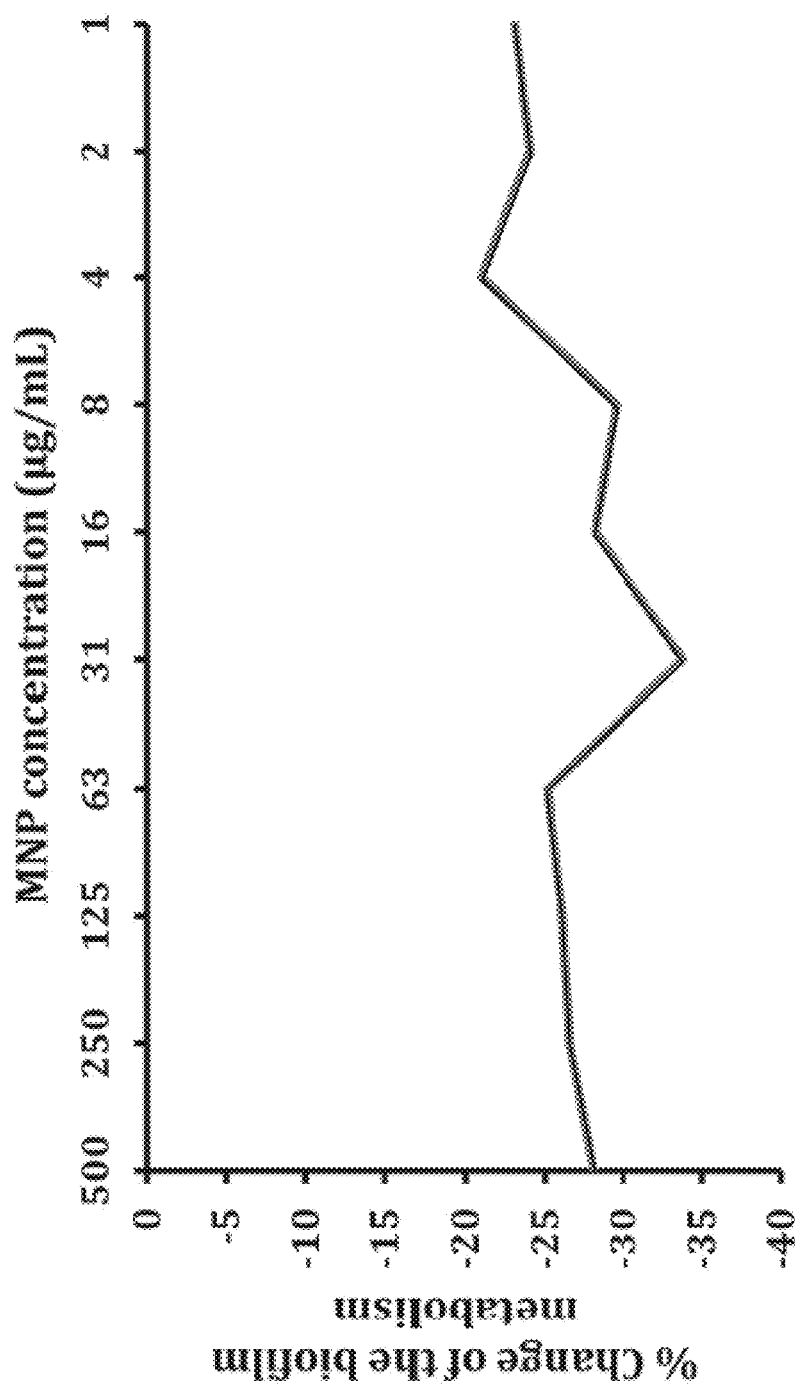
FIG. 17C illustrates % change in biofilm metabolism versus the MNP concentration used during treatment, in accordance with various embodiments.

FIG. 17A illustrates biofilms only with magnetic exposure; note the significantly low metabolic activity of the biofilm exposed to both static one sided and static switched magnetic fields compared to unexposed controls. FIG. 17B illustrates biofilms treated with MNPs (200 µg/ml) and exposed to static magnetic fields; note the significantly low metabolic activities of the biofilms treated with MNPs compared to controls and MNPs and exposed to magnetic fields compared to both controls and biofilms treaded only with MNPs. FIG. 17C illustrates the concentration dependent effect of MNPs on preformed 24 h mixed species oral biofilms; The biofilm metabolic activity was suppressed between 26-34% when treated over 4 µg/ml of MNPs. In FIGS. 17A and 17B, * indicates significant changes and P<0.05 is considered statistically significant.

TABLE 1

The metabolic activities (XTT) of mixed species oral biofilms exposed to MNP treatment and magnetic fields.
P < 0.05 is considered statistically significant.

| Treatment group | Mean XTT ± SD | % Reduction compared to control | P value (compared to control) |
| --- | --- | --- | --- |
| Control | 0.452 ± 0.046 | | |
| Static one sided only | 0.320 ± 0.031 | 29 | <0.05 |
| Static switched only | 0.263 ± 0.024 | 42 | <0.05 |
| MNP only | 0.300 ± 0.009 | 34 | <0.05 |
| MNP + Static one sided | 0207 ± 0.024 | 54 | <0.05 |
| MNP + Static switched | 0.213 ± 0.018 | 53 | <0.05 |

Figure 18A:
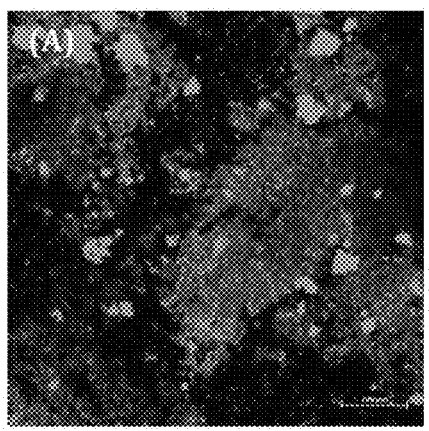
FIGS. 18A-F illustrate CLSM images of mixed species oral biofilms exposed to different magnetic fields with or without MNP treatment, in accordance with various embodiments.
Figure 18B:
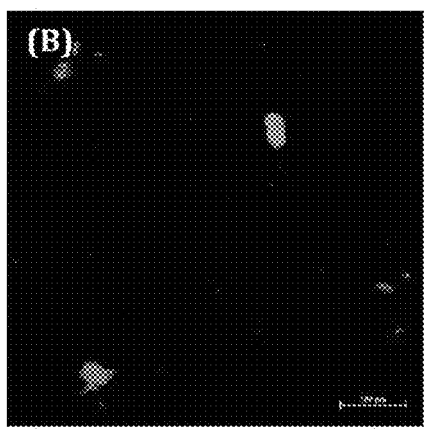
Figure 18C:
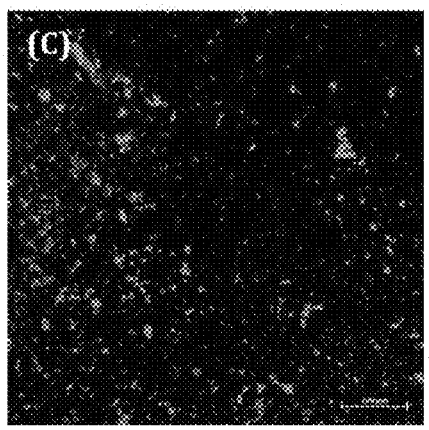
Figure 18D:
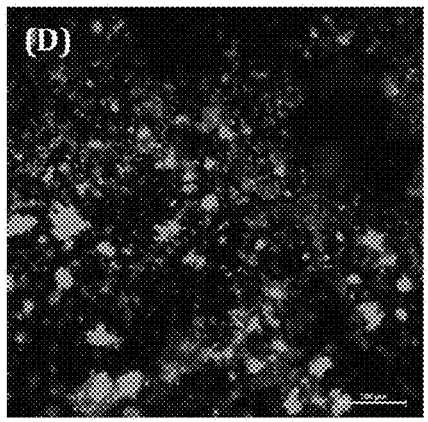
Figure 18E:
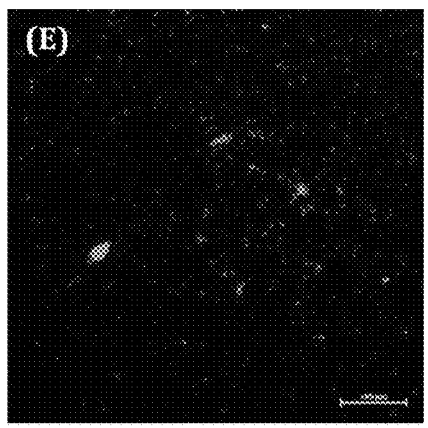
Figure 18F:
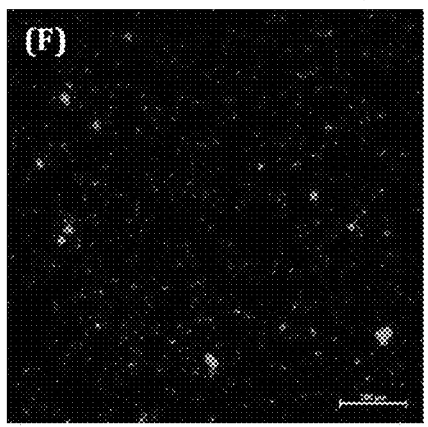

Confocal laser scanning microscopy. FIGS. 18A-F illustrate CLSM images of mixed species oral biofilms exposed to different magnetic fields with or without MNP treatment (magnification×20) (stained using a LIVE/DEAD BacLight bacterial viability kit; Invitrogen). Live cells were stained in green and dead cells in red. FIG. 18A illustrates an undisturbed control; FIG. 18B illustrates a biofilm exposed to static one sided magnetic fields; FIG. 18C illustrates a biofilm exposed to static switched magnetic fields; FIG. 18D illustrates a biofilm exposed to MNPs (200 µg/ml) alone; FIG. 18E illustrates a biofilm exposed to MNPs and static one sided magnetic fields; FIG. 18F illustrates a biofilm exposed to MNPs and static switched magnetic fields; note the significant reduction of the cellular content, stratified architecture and lack of extracellular components in the test biofilms (B, C, D, E and F) compared to three dimensionally arranged and dense biofilm controls with substantial extracellular materials (A). The control biofilm (FIG. 18A) that was not exposed to magnetic fields demonstrated a dense, spatially oriented and confluent biofilm with substantial amount of extracellular substances for 24 hour biofilms. The biofilms exposed to both one sided and switched static magnetic fields exhibited significantly lower quantity of microbial cells and lack of organized structure or extracellular substances (FIGS. 18B and C). Few isolated microbial colonies were seen in the biofilm after static one sided exposure whereas scattered smaller microbial colonies were observed when treated with static switched magnetic fields.

Example 4.3

The Effects of Various Magnetic Fields on Mixed Species Oral Biofilms Co-Treated With Magnetic Nanoparticles Concentration dependent effect of MNP on mixed species oral biofilms. When treated with MNPs above 8 µg/mL, mixed oral biofilms showed 26-34% of reduction in the metabolism as indicated by XTT readings (FIG. 18C).

Biofilm metabolism (XTT reduction assay). When MNP treated biofilms were exposed to aforementioned different magnetic fields, all test treatments showed significant suppression of biofilm metabolism ($p<0.05$) compared to untreated biofilm control as well as MNP treated biofilms (FIG. 2B, Table 1). Biofilms that were exposed to MNPs alone had a significantly lowered metabolic activity compared to control biofilms ($p<0.05$, FIG. 2B, Table 1). Comparing the different magnetic field treatments to each other, no significant differences in the mean XTT readings were found (Table 1).

Confocal laser scanning microscopy. When treated with MNPs, oral biofilm showed a significantly lower biofilm mass compared to control (FIG. 18D). More importantly, there was a notable reduction in the extracellular matrix in the MNP treated biofilm (FIG. 18D vs 18A). However, the remnants of the biofilm structure were preserved. When MNP treated Moans were exposed to both static one sided and static switched magnetic fields, complete destruction of the biofilms were noted (FIGS. 18E and 18F). There was no structured biofilm or extracellular matrix observed in CLSM images. Instead, scattered bacterial cells were visible in the microscopic field compared to the control biofilm (FIGS. 18E and 18F).

The terms and expressions that have been employed are used as terms of description and not of limitation, and there is no intention in the use of such terms and expressions of excluding any equivalents of the features shown and described or portions thereof, but it is recognized that various modifications are possible within the scope of the embodiments of the present invention. Thus, it should be understood that although the present invention has been specifically disclosed by specific embodiments and optional features, modification and variation of the concepts herein disclosed may be resorted to by those of ordinary skill in the art, and that such modifications and variations are considered to be within the scope of embodiments of the present invention.

Additional Embodiments.

The following exemplary embodiments are provided, the numbering of which is not to be construed as designating levels of importance:

Embodiment 1 provides a method of antimicrobial treatment, the method comprising:
at least one of
exposing at least one microbe to a magnetic field, and
contacting the at least one microbe with at least one nanoparticle comprising iron.

Embodiment 2 provides the method of Embodiment 1, wherein the method is performed in vitro.

Embodiment 3 provides the method of any one of Embodiments 1-2, wherein the method is performed in vivo.

Embodiment 4 provides the method of any one of Embodiments 1-3, wherein the method is a method of biofilm treatment, wherein the at least one microbe is incorporated in a biofilm.

Embodiment 5 provides the method of any one of Embodiments 1-4, wherein the method comprises the exposing of the microbe to the magnetic field, wherein the method is free of the contacting of the microbe with the at least one nanoparticle.

Embodiment 6 provides the method of any one of Embodiments 1-5, wherein the method comprises the contacting of the microbe with the nanoparticle, wherein the method is free of the exposing of the microbe to the magnetic field.

Embodiment 7 provides the method of any one of Embodiments 1-6, wherein the method comprises the exposing of the microbe to the magnetic field and the contacting of the microbe with the nanoparticle.

Embodiment 8 provides the method of any one of Embodiments 1-7, wherein the exposing of the microbe to the magnetic field and the contacting of the microbe with the nanoparticle occur at least partially simultaneously.

Embodiment 9 provides the method of any one of Embodiments 1-8, wherein the exposing of the microbe to the magnetic field and the contacting of the microbe with the nanoparticle occur substantially simultaneously.

Embodiment 10 provides the method of any one of Embodiments 1-9, comprising spraying the nanoparticle on the microbe.

Embodiment 11 provides the method of any one of Embodiments 1-10, wherein the exposing of the microbe to the magnetic field or the contacting of the microbe with the nanoparticle occur for a period of about 0.01 second to about 4 weeks.

Embodiment 12 provides the method of any one of Embodiments 1-11, wherein the exposing of the microbe to the magnetic field or the contacting of the microbe with the nanoparticle occur for a period of about 1 minute to about 1 day.

Embodiment 13 provides the method of any one of Embodiments 1-12, wherein the method of antimicrobial treatment is sufficient to kill the microbe.

Embodiment 14 provides the method of any one of Embodiments 1-13, wherein the at least one microbe is at least one of gram positive and gram negative.

Embodiment 15 provides the method of any one of Embodiments 1-14, wherein the at least one microbe is at least one of a bacteria and a fungus.

Embodiment 16 provides the method of any one of Embodiments 1-15, wherein the at least one microbe is at least one of *Staphylococcus epidermidis, Staphylococcus aureus, Streptococcus* spp, *Pseudomonas aeruginosa, Burkholderia cepacia, Candida* spp, *Escherichia coli, Streptococcus mutans, Rubus fruticosus, Shewanella oneidensis, Saccharomyces cerevisiae, Bacillus anthracis, Bacillus circulars, Micrococcus luteus, Pseudomonas fluorescens, Salmonella enteritidis, Serratia marcescens, Hordeum vulgare, Mycobacterium tuberculosis, Ervinia carotovora, Streptomyces scabies, Haemophilus* spp., *Bordetella pertussis, Coxiella burnetii, Klebsiella pneumonia, Mycoplasma pneumonia, Chlamydophila pneumonia, Legionella pneumophila, Moraxella catarrhalis, Yersinia pestis, Heliobacterium pylori*, and *Alternaria solani*.

Embodiment 17 provides the method of any one of Embodiments 1-16, wherein the at least one microbe is *Pseudomonas aeruginosa*.

Embodiment 18 provides the method of any one of Embodiments 1-17, wherein the exposing of the microbe to the magnetic field and the contacting of the microbe with the nanoparticle occurs at a temperature of about −100° C. to about 100° C.

Embodiment 19 provides the method of any one of Embodiments 1-18, wherein the magnetic field comprises at least one of a static magnetic field, a time-varying magnetic field, and a magnetic field that oscillates in polarity.

Embodiment 20 provides the method of Embodiment 19, wherein the oscillating magnetic field has an oscillation of about 0.01 kHz/100 Oe to about 10,000,000 kHz/100 Oe.

Embodiment 21 provides the method of any one of Embodiments 19-20, wherein the oscillating magnetic field is an alternating magnetic field.

Embodiment 22 provides the method of any one of Embodiments 19-21, wherein the oscillating magnetic field is a switched magnetic field.

Embodiment 23 provides the method of Embodiment 22, wherein the magnetic field is switched every about 0.01 to about 20 h.

Embodiment 24 provides the method of any one of Embodiments 22-23, wherein the magnetic field is switched every about 1 minute to about 120 minutes.

Embodiment 25 provides the method of any one of Embodiments 1-24, wherein the magnetic field has a strength of about 0.001 kGs to about 10,000,000 kGs.

Embodiment 26 provides the method of any one of Embodiments 1-25, wherein the magnetic field has a strength of about 0.01 kGs to about 10 kG.

Embodiment 27 provides the method of any one of Embodiments 1-26, wherein the exposing of the microbe to the magnetic field comprises exposing the nanoparticle to the magnetic field.

Embodiment 28 provides the method of any one of Embodiments 1-27, wherein the nanoparticle is a magnetic nanoparticle.

Embodiment 29 provides the method of any one of Embodiments 1-28, wherein the iron in the nanoparticle is at least one of iron oxide and zero-valent iron.

Embodiment 30 provides the method of any one of Embodiments 1-29, wherein the iron in the nanoparticle is an iron compound that is at least one of FeO, $Fe_3O_4$, $Fe_4O_5$, $Fe_2O_3$.

Embodiment 31 provides the method of any one of Embodiments 1-30, wherein the iron in the nanoparticle is an iron compound that is $Fe_3O_4$.

Embodiment 32 provides the method of any one of Embodiments 1-31, wherein the nanoparticle is a superparamagnetic iron oxide nanoparticle.

Embodiment 33 provides the method of any one of Embodiments 1-32, wherein a ferrofluid comprises the nanoparticle.

Embodiment 34 provides the method of any one of Embodiments 1-33, wherein the concentration of the nanoparticies is about 0.0001 μg/mL, to about 1 g/mL.

Embodiment 35 provides the method of any one of Embodiments 1-34, wherein the nanoparticle has a largest dimension of about 1 nm to about 999 nm.

Embodiment 36 provides the method of any one of Embodiments 1-35, wherein the nanoparticle has a largest dimension of about 10 nm to about 400 nm.

Embodiment 37 provides the method of any one of Embodiments 1-36, wherein the nanoparticle comprises at least one organic substituent thereon.

Embodiment 38 provides the method of Embodiment 37, wherein the organic substituent comprises a saccharide, a polysaccharide, a poly(oxy(substituted or unsubstituted ($C_2$-$C_3$)alkyl)), or a substituted or unsubstituted ($C_1$-$C_{200}$)hydrocarbyl group interrupted by 0, 1, 2, or 3 groups independently chosen from —O—, —S—, —(O($C_2$-$C_3$)alkylene)$_n$- wherein n is 1 to 1,000, and substituted or unsubstituted —NH—.

Embodiment 39 provides the method of any one of Embodiments 37-38, wherein the organic substituent comprises at least one of alginate, chitosan, curdlan, dextran, derivatized dextran, emulsan, a galactoglucopolysaccharide, gellan, glucuronan, N-acetyl-glucosamine, N-acetyl-heparosan, hyaluronic acid, kefiran, lentinan, levan, mauran, pullulan, scleroglucan, schizophyllan, stewartan, succinoglycan, xanthan, diutan, welan, starch, derivatized starch, tamarind, tragacanth, guar gum, derivatized guar gum, gum ghatti, gum arabic, locust bean gum, cellulose, and derivatized cellulose.

Embodiment 40 provides the method of any one of Embodiments 37-39, wherein the organic substituent comprises at least one of alginate, polyethyleneglycol, and polyethyleneglycol-COOH.

Embodiment 41 provides the method of any one of Embodiments 37-40, wherein the organic substituent comprises a drug.

Embodiment 42 provides the method of any one of Embodiments 37-41, wherein the organic substituent comprises an antibiotic.

Embodiment 43 provides the method of any one of Embodiments 37-42, wherein the nanoparticle comprises about 1 to about 10,000,000 of the organic substituents.

Embodiment 44 provides the method of any one of Embodiments 37-43, wherein the nanoparticle comprises more than one of the organic substituents, wherein at least some of the organic substituents are crosslinked.

Embodiment 45 provides the method of Embodiment 44, wherein the crosslinking comprises direct crosslinking between organic substituents or crosslinking between organic substituents via one or more linkers.

Embodiment 46 provides the method of any one of Embodiments 37-44, wherein a drug is at least one of crosslinked and conjugated to the organic substituent.

Embodiment 47 provides the method of Embodiment 46, wherein the crosslinking between the organic substituent and the drug is EDC/sulfo-NHS cross-linking.

Embodiment 48 provides the method of any one of Embodiments 1-47, wherein the method further comprises exposing the at least microbe to at least one antibiotic.

Embodiment 49 provides the method of Embodiment 48, wherein the antibiotic is at least one of ciprofloxacin hydrochloride and tobramycin.

Embodiment 50 provides the method of Embodiment 50, wherein the exposing the microbe to the antibiotic occurs at least partially simultaneously with at least one of the exposing of the microbe to the magnetic field and the contacting of the microbe with the nanoparticle.

Embodiment 51 provides the method of Embodiment 50, wherein the exposing the microbe to the antibiotic occurs substantially simultaneously with at least one of the exposing of the microbe to the magnetic field and the contacting of the microbe with the nanoparticle.

Embodiment 52 provides a method of antimicrobial treatment, the method comprising:

exposing at least one microbe to an oscillating magnetic field, and contacting the at least one microbe with at least one nanoparticle comprising $Fe_3O_4$.

Embodiment 53 provides a composition for antimicrobial treatment, comprising:

at least one nanoparticle of any one of Embodiments 1-51.

Embodiment 54 provides a composition for antimicrobial treatment, comprising:

at least one nanoparticle comprising iron.

Embodiment 55 provides a medical device or medical implant comprising the composition of any one of Embodiments 53-54.

Embodiment 56 provides a coating comprising the composition of any one of Embodiments 53-54.

Embodiment 57 provides the composition of any one of Embodiments 53-54, further comprising a drug.

Embodiment 58 provides the method or composition of any one or any combination of Embodiments 1-57 optionally configured such that all elements or options recited are available to use or select from.

What is claimed is:

1. A method of antimicrobial treatment, the method comprising:
    exposing at least one microbe in a biofilm to a static switched magnetic field, the exposing comprising alternating between applying a first static magnetic field to the microbe and applying a second static magnetic field having a different direction than the first static magnetic field to the microbe, wherein the alternating is performed in one or more periods of about 0.1 second to about 20 hours and a field strength of the first static magnetic field and the second static magnetic field is independently about 0.01 kG to about 10 kG; and
    contacting the biofilm with at least one nanoparticle comprising iron;
    wherein the contacting the biofilm with the nanoparticle and the exposing of the biofilm to the magnetic field is alone sufficient to kill the microbe without additional treatment steps, and
    wherein the exposing of the microbe to the static switched magnetic field and the contacting of the microbe with the nanoparticle occur at least partially simultaneously.

2. The method of claim 1, wherein the at least one microbe is at least one of a bacteria and a fungus.

3. The method of claim 1, wherein the nanoparticle is a magnetic nanoparticle.

4. The method of claim 1, wherein the iron in the nanoparticle is at least one of FeO, $Fe_3O_4$, $Fe_4O_5$, and $Fe_2O_3$.

5. The method of claim 1, wherein the nanoparticle comprises at least one organic substituent thereon.

6. The method of claim 5, wherein the organic substituent comprises a drug, a saccharide, a polysaccharide, a poly(oxy (substituted or unsubstituted ($C_2$-$C_3$)alkyl)), or a substituted or unsubstituted ($C_7$-$C_{200}$)hydrocarbyl group interrupted by 0, 1, 2, or 3 groups independently chosen from —O—, —S—, —(O($C_2$-$C_3$)alkylene), wherein n is 1 to 1,000, and substituted or unsubstituted —NH—.

7. The method of claim 5, wherein the organic substituent comprises at least one of alginate, polyethyleneglycol, and polyethyleneglycol-COOH.

8. The method of claim 5, wherein the nanoparticle comprises more than one of the organic substituents, wherein at least some of the organic substituents are crosslinked.

9. The method of claim 5, wherein a drug is at least one of crosslinked and conjugated to the organic substituent.

10. The method of claim 1, wherein the magnetic field is provided by a molybdenum magnet.

11. The method of claim 1, wherein the magnetic field is less than 5 kG and less than 0.1 kHz/100 Oe, and the direction of the magnetic field is periodically switched in one or more periods of about 1 minute to about 120 minutes.

12. The method of claim 1, wherein the biofilm is an oral biofilm.

13. The method of claim 1, wherein the exposing comprises alternating between applying the first static magnetic field to the microbe from a first direction and applying the second static magnetic field to the microbe from an opposite direction to the first direction.

14. A method of antimicrobial treatment; the method comprising:
    at least one of
        exposing at least one microbe in a biofilm to a static switched magnetic field, the exposing comprising alternating between applying a first static magnetic field to the microbe from a first direction and applying a second static magnetic field to the microbe from an opposite direction to the first direction wherein the alternating is performed in one or more periods of about 0.1 second to about 20 hours, and a field strength of the first static magnetic field and the second static magnetic field is independently about 0.01 kG to about 10 kG; and
    contacting the biofilm with at least one nanoparticie comprising iron;
    wherein the contacting the biofilm with the nanoparticle, and the exposing of the biofilm to the static switched magnetic field, or the combination thereof, is alone sufficient to kill the microbe without additional treatment steps.

* * * * *

UNITED STATES PATENT AND TRADEMARK OFFICE
CERTIFICATE OF CORRECTION

PATENT NO. : 11,135,325 B2
APPLICATION NO. : 15/549974
DATED : October 5, 2021
INVENTOR(S) : Osinski et al.

Page 1 of 2

It is certified that error appears in the above-identified patent and that said Letters Patent is hereby corrected as shown below:

On the Title Page

In Column 2, under "Other Publications", Line 8, delete "Coupied" and insert --Coupled-- therefor In Column 2, under "Other Publications", Line 21, delete ""Pseudomanas" and insert --"Pseudomonas-- therefor On page 2, in Column 2, under "Other Publications", Line 20, delete "biofilem" and insert --biofilm-- therefor On page 2, in Column 2, under "Other Publications", Line 36, delete "superpararnegnetic" and insert --superparamagnetic-- therefor On page 2, in Column 2, under "Other Publications", Line 61, delete "Pseudomon as" and insert --Pseudomonas-- therefor On page 2, in Column 2, under "Other Publications", Line 61, delete "Aeroginose," and insert --Aeroginosa,-- therefor On page 3, in Column 1, under "Other Publications", Line 1, delete "nanoparticie" and insert --nanoparticle-- therefor In the Claims In Column 39, Line 32, in Claim 1, after "hours", insert --,--

In Column 40, Line 4, in Claim 6, delete "$(C_7-C_{200})$hydrocarbyl" and insert --$(C_1-C_{200})$hydrocarbyl-- therefor Signed and Sealed this
Twenty-fourth Day of October, 2023

Katherine Kelly Vidal
*Director of the United States Patent and Trademark Office*

CERTIFICATE OF CORRECTION (continued)
U.S. Pat. No. 11,135,325 B2

In Column 40, Line 6, in Claim 6, delete "-(O($C_2$-$C_3$)alkylene),") and insert -- -(O($C_2$-$C_3$)alkylene)$_n$-- therefor In Column 40, Line 30, in Claim 14, delete "treatment;" and insert --treatment,-- therefor In Column 40, Line 38, in Claim 14, after "direction", insert --,--

In Column 40, Line 44, in Claim 14, delete "nanoparticie" and insert --nanoparticle-- therefor